(12) United States Patent
Anthony et al.

(10) Patent No.: US 8,557,973 B2
(45) Date of Patent: *Oct. 15, 2013

(54) DETECTION OF NUCLEIC ACIDS BY TARGET-SPECIFIC HYBRID CAPTURE METHOD

(75) Inventors: James Anthony, Fredrick, MD (US);
Attila Lorincz, North Potomac, MD (US); John Troy, Fairfax, VA (US);
Yanglin Tan, Rockville, MD (US)

(73) Assignee: Qiagen Gaithersburg, Inc.,
Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/904,459

(22) Filed: Oct. 14, 2010

(65) Prior Publication Data

US 2011/0059542 A1    Mar. 10, 2011

Related U.S. Application Data

(62) Division of application No. 12/253,976, filed on Oct. 19, 2008, now Pat. No. 7,829,691, which is a division of application No. 09/594,839, filed on Jun. 15, 2000, now Pat. No. 7,439,016.

(51) Int. Cl.
*C07H 21/04* (2006.01)
*C12Q 1/68* (2006.01)

(52) U.S. Cl.
USPC .................................. 536/24.3; 435/6.12

(58) Field of Classification Search
None
See application file for complete search history.

(56) References Cited

U.S. PATENT DOCUMENTS

| | | | |
|---|---|---|---|
| 4,486,539 A | 12/1984 | Ranki et al. |
| 4,563,417 A | 1/1986 | Alabrella et al. |
| 4,563,419 A | 1/1986 | Ranki et al. |
| 4,731,325 A | 3/1988 | Palva et al. |
| 4,732,847 A | 3/1988 | Stuart et al. |
| 4,743,535 A | 5/1988 | Carrico |
| 4,751,177 A | 6/1988 | Stabinsky |
| 4,775,619 A | 10/1988 | Urdea |
| 4,833,084 A | 5/1989 | Carrico |
| 4,851,330 A | 7/1989 | Kohne |
| 4,865,980 A | 9/1989 | Stuart et al. |
| 4,868,105 A | 9/1989 | Urdea et al. |
| 4,889,798 A | 12/1989 | Rabbani |
| 4,894,325 A | 1/1990 | Englehardt et al. |
| 5,082,830 A | 1/1992 | Brakel et al. |
| 5,106,727 A | 4/1992 | Hartley et al. |
| 5,116,734 A | 5/1992 | Higgs et al. |
| 5,200,313 A | 4/1993 | Carrico |
| 5,288,611 A | 2/1994 | Kohne |
| 5,374,524 A | 12/1994 | Miller |
| 5,424,413 A | 6/1995 | Hogan et al. |
| 5,437,977 A | 8/1995 | Segev |
| 5,474,895 A | 12/1995 | Ishii et al. |
| 5,484,699 A | 1/1996 | Bouma et al. |
| 5,556,748 A | 9/1996 | Douglas |
| 5,614,362 A | 3/1997 | Urdea et al. |
| 5,623,049 A | 4/1997 | Lobberding et al. |
| 5,627,030 A | 5/1997 | Pandian et al. |
| 5,629,153 A | 5/1997 | Urdea |
| 5,629,156 A | 5/1997 | Shah et al. |
| 5,641,630 A | 6/1997 | Snitman et al. |
| 5,656,731 A | 8/1997 | Urdea |
| 5,681,697 A | 10/1997 | Urdea et al. |
| 5,695,926 A | 12/1997 | Cros et al. |
| 5,702,893 A | 12/1997 | Urdea et al. |
| 5,728,531 A | 3/1998 | Yamada et al. |
| 5,731,153 A | 3/1998 | Lucas et al. |
| 5,736,316 A | 4/1998 | Irvine et al. |
| 5,747,244 A | 5/1998 | Sheridan et al. |
| 5,747,248 A | 5/1998 | Collins |
| 5,750,338 A | 5/1998 | Collins et al. |
| 5,759,773 A | 6/1998 | Tyagi et al. |
| 5,786,183 A | 7/1998 | Ryder et al. |
| 5,792,606 A | 8/1998 | Deger et al. |
| 5,800,994 A | 9/1998 | Martinelli et al. |
| 5,821,339 A | 10/1998 | Schaffer et al. |
| 5,827,661 A | 10/1998 | Blais |
| 5,853,993 A | 12/1998 | Dellinger et al. |
| 5,888,724 A | 3/1999 | Silverstein et al. |
| 5,981,179 A | 11/1999 | Lorinez et al. |
| 5,993,821 A * | 11/1999 | Frazer et al. ............... 424/204.1 |
| 5,994,079 A | 11/1999 | De La Rosa et al. |
| 6,027,897 A | 2/2000 | Lorincz et al. |
| 6,043,038 A | 3/2000 | Sivaraja et al. |

(Continued)

FOREIGN PATENT DOCUMENTS

| EP | 079139 | 5/1983 |
|---|---|---|
| EP | 144914 | 6/1985 |

(Continued)

OTHER PUBLICATIONS

Lowe et al., A computer program for selection of oligonucleotide primers for polymerase chain reactions. Nucleic Acids Research, vol. 18, No. 7, pp. 1757-1761, 1990.*

Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.

Partial European Search Report of EP10185824; mailed Feb. 16, 2011 (8 pages).

Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.

(Continued)

*Primary Examiner* — Prabha Chunduru
(74) *Attorney, Agent, or Firm* — Miles & Stockbridge, P.C.

(57) ABSTRACT

Target-specific hybrid capture (TSHC) provides a nucleic acid detection method that is not only rapid and sensitive, but is also highly specific and capable of discriminating highly homologous nucleic acid target sequences. The method produces DNA-RNA hybrids which can be detected by a variety of methods.

31 Claims, 9 Drawing Sheets

(56) References Cited

U.S. PATENT DOCUMENTS

| | | | |
|---|---|---|---|
| 6,057,099 A | 5/2000 | Nathan et al. | |
| 6,083,925 A | 7/2000 | Li et al. | |
| 6,110,676 A | 8/2000 | Coull et al. | |
| 6,110,682 A | 8/2000 | Dellinger et al. | |
| 6,221,581 B1 | 4/2001 | Engelhardt et al. | |
| 6,228,578 B1 | 5/2001 | Impraim et al. | |
| 6,232,462 B1 | 5/2001 | Collins et al. | |
| 6,268,128 B1 | 7/2001 | Collins et al. | |
| 6,277,579 B1 | 8/2001 | Lazar et al. | |
| 6,326,136 B1 | 12/2001 | Lazar et al. | |
| 6,355,424 B1 * | 3/2002 | Lorincz et al. | 435/6 |
| 6,436,662 B1 | 8/2002 | Mielzynska et al. | |
| 6,521,190 B1 | 2/2003 | Edens et al. | |
| 6,544,732 B1 | 4/2003 | Chee et al. | |
| 6,583,278 B1 | 6/2003 | Carter | |
| 6,686,151 B1 | 2/2004 | Lazar et al. | |
| 6,828,098 B2 | 12/2004 | Langmore et al. | |
| 6,890,729 B2 | 5/2005 | Mietzynska et al. | |
| 6,969,585 B2 | 11/2005 | Lorincz et al. | |
| 6,977,148 B2 | 12/2005 | Dean et al. | |
| 7,001,776 B2 | 2/2006 | Botacini das Dores et al. | |
| 7,371,518 B2 | 5/2008 | Lorincz et al. | |
| 7,812,144 B2 | 10/2010 | Karlsen | |
| 7,829,691 B2 * | 11/2010 | Anthony et al. | 536/24.32 |
| 2001/0055766 A1 | 12/2001 | Aristarkhov et al. | |
| 2002/0012936 A1 | 1/2002 | Lorincz et al. | |
| 2003/0096232 A1 | 5/2003 | Kris et al. | |
| 2003/0108897 A1 | 6/2003 | Drmanac | |
| 2003/0175765 A1 | 9/2003 | Kessler et al. | |
| 2003/0175789 A1 | 9/2003 | Weininger et al. | |
| 2004/0180362 A1 | 9/2004 | Lazar et al. | |
| 2004/0214302 A1 | 10/2004 | Anthony et al. | |
| 2005/0032038 A1 | 2/2005 | Fisher et al. | |
| 2005/0032105 A1 | 2/2005 | Bair et al. | |
| 2005/0147996 A1 | 7/2005 | Sorge | |
| 2006/0051809 A1 | 3/2006 | Nazarenko et al. | |
| 2006/0160188 A1 | 7/2006 | Kurnit et al. | |
| 2006/0240449 A1 | 10/2006 | McGlennen et al. | |
| 2007/0154884 A1 | 7/2007 | Lorincz | |
| 2008/0200344 A1 | 8/2008 | Cheng | |
| 2008/0247914 A1 | 10/2008 | Edens et al. | |
| 2009/0032445 A1 | 2/2009 | Doak et al. | |
| 2009/0263819 A1 | 10/2009 | Muraca | |
| 2009/0286687 A1 | 11/2009 | Dressman et al. | |
| 2009/0298187 A1 | 12/2009 | Nazarenko et al. | |
| 2010/0081124 A1 | 4/2010 | Abravaya et al. | |
| 2010/0311039 A1 | 12/2010 | Lowe et al. | |

FOREIGN PATENT DOCUMENTS

| | | |
|---|---|---|
| EP | 0163220 | 12/1985 |
| EP | 167366 | 1/1986 |
| EP | 184017 | 6/1986 |
| EP | 281927 | 9/1988 |
| EP | 0288737 | 11/1988 |
| EP | 0333465 | 9/1989 |
| EP | 336454 | 10/1989 |
| EP | 703296 | 3/1996 |
| EP | 1 806 410 A2 | 7/2007 |
| EP | 2 184 368 A1 | 5/2010 |
| JP | 2009 106220 | 5/2009 |
| WO | 84/02721 | 7/1984 |
| WO | 8607387 | 12/1986 |
| WO | 88/03957 | 6/1988 |
| WO | 89/11546 | 11/1989 |
| WO | 91/08312 A1 | 6/1991 |
| WO | 9310263 | 5/1993 |
| WO | 93/10263 | 6/1993 |
| WO | 94/16108 | 7/1994 |
| WO | 95/16055 | 6/1995 |
| WO | 95/17430 | 6/1995 |
| WO | 9640992 | 5/1996 |
| WO | 96/40992 | 12/1996 |
| WO | 97/05277 | 2/1997 |
| WO | 9705277 | 2/1997 |
| WO | 9710364 | 3/1997 |
| WO | 97/31256 | 8/1997 |
| WO | 98/18488 | 5/1998 |
| WO | 98/22620 | 5/1998 |
| WO | 9818488 | 5/1998 |
| WO | 9822620 | 5/1998 |
| WO | 9859044 | 12/1998 |
| WO | 99/02488 | 1/1999 |
| WO | 99/29909 | 6/1999 |
| WO | 99/32654 | 7/1999 |
| WO | 99/36571 | 7/1999 |
| WO | 99/39001 | 8/1999 |
| WO | 99/40224 | 8/1999 |
| WO | 9949224 | 9/1999 |
| WO | 99/50459 | 10/1999 |
| WO | 0060116 | 10/2000 |
| WO | 00/60116 | 11/2000 |
| WO | 0136681 | 5/2001 |
| WO | 0196608 | 12/2001 |
| WO | 2004/087950 | 10/2004 |
| WO | 2005080602 | 9/2005 |
| WO | 2007/056723 | 5/2007 |
| WO | 2007/130519 A2 | 11/2007 |
| WO | 2008/036061 | 3/2008 |
| WO | 2008/139938 A1 | 11/2008 |
| WO | 2009/057993 A1 | 5/2009 |
| WO | 2009/123996 | 10/2009 |
| WO | 2010/004251 A1 | 1/2010 |
| WO | 2010/028382 | 3/2010 |
| WO | 2010/127228 A1 | 11/2010 |

OTHER PUBLICATIONS

Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.

International Search Report and Written Opinion of PCT/US2010/048714, dated Dec. 10, 2010 (14 pages).

International Preliminary Report on Patentability and Written Opinion of PCT/US2009/041033, dated Oct. 19, 2010 (6 pages).

International Search Report and Written Opinion of PCT/US2010/047769, dated Nov. 9, 2010 (11 pages).

Pachowics, et al., "Sequence specific large vol. sample prep solution utilizing Hybrid Capture technology," 41st Annual Oak Ridge Conference; Baltimore, MD; Apr. 16, 2009; retrieved from the Internet: http://www.aacc.org/events/meeting_proceeding/2009/Documents/OakRidge09AllPosters.pdf.

Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.

Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.

Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.

Nazarenko et al., "A novel method of HPV genotyping using Hybrid Capture sample preparation method combined with GP5+/6+ PCR and multiplex detection on Luminex XMAP," Journal of Virological Methods, Dec. 1, 2008, pp. 76-81, vol. 154, No. 1-2, Elsevier BV, XP025680302.

Taha et al., "Universal Collection Medium (UCM) is as suitable as the Standard Transport Medium (STM) for Hybrid Capture II (HC-2) assay," Journal of Virological Methods, May 1, 2006, pp. 32-35, vol. 36, No. 1, Elsevier BV, XP025178639.

Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott—Raven Publishers, XP008011933.

(56) References Cited

OTHER PUBLICATIONS

Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.
Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.
Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.
Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.
International Search Report and Written Opinion of PCT/US2011/22887, dated Jun. 1, 2011.
International Preliminary Report on Patentability and Written Opinion of PCT/US2009/062061, dated May 12, 2011.
International Preliminary Report on Patentability and Written Opinion of PCT/US2009/062041, dated May 12, 2011.
GenBank Submission FJ429103. 2009 [Retrieved from the Internet May 20, 2011: <URL:http://www.ncbl_nlm.nih.gov/nuccore/FJ429103.1>]; in entirety.
Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.
International Search Report and Written Opinion based on PCT/US2001/037012 mailed Apr. 17, 2012.
Mittendorf T, et al., "HPV-DNA-Diagnostik zur Zervixkarzinomfruherkennung; Deutsche Agentur für HTA des Deutschen Instituts für Medizinische Dokumentation und Information," 1. Auflage 2007.
Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.
Davey DD, et al., "Introduction and Commentary, Strategic Science Symposium, Human Papillomavirus Testing—Are you ready for a new era in cervical cancer screening?," Arch Pathol Lab Med, 127: 927-929, Aug. 2003.
Malloy C, et al., "HPV DNA Testing: Technical and Programmatic Issues for Cervical Cancer Prevention in Low-Resource Settings," Path, Dec. 2000.
Stacey SN, et al., "Translation of the Human Papillomavirus Type 16 E7 Oncoprotein from Bicistronic mRNA is independent of Splicing Events within the E6 Open Reading Frame," Journal of Virology, 69(11):7023-7031. Nov. 1995.
Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).
Bohm S, et al., "The Predominant mRNA Class in HPV16-Infected Genital Neoplasias does not Encode the E6 or the E7 Protein," Int J. Cancer: 55, 791-798 (1993).
Middleton, K, et al., "Organization of Human Papillomavirus Productive Cycle during Neoplastic Progression Provides a Basis for Selection of Diagnostic markers," Journal of Virology, Oct. 2003, pp. 10186-10201.
Stoler, M, et al., "Human Papillomavirus Type 16 and 18 Gene Expression in Cervical Neoplasias," Human Pathol. 23 (1992), pp. 117-128.
Higgins, G, et al., "Transcription patterns of human papillomavirus type 16 in genital intraepithelial neoplasia: evidence for promoter usage within the E7 open reading frame during epithelial differentiation," J. Gen. Virol. 73(1992), pp. 2047-2057.
Karlsen, F, et al., "Use of Multiple PCR Primer Sets for Optimal Detection of Human Papillomavirus," J. Clin. Microbiol. 34 (1996), pp. 2095-2100.
Park, JS, et al., "Physical Status and Expression of HPV Genes in Cervical Cancers," Gynec. Oncol. 95 (1997), pp. 121-129.
Broker, TR, et al., "A Molecular Portrait of Human Papillomavirus Carcinogenesis," Cancer Cells 7 (1989), pp. 197-207.
Letter dated Jan. 6, 2010 to EPO re EP 1 038 022 (46 pages).
Letter to EPO dated Mar. 2, 2009 re EP 1 038 022 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
Lowe et al; "A Hybrid-Capture Assay to Detect HPV MRNA Ratios in Cervical Specimens"; Journal of Virological Methods; vol. 179; No. 1; January 2012; pp. 142-147.
International Search Report Based on Application No. PCT/US2012/026380 Mailed Oct. 15, 2012.
International Search Report Based on Application No. PCt/US2012/020684 mailed Oct. 25, 2012.
Clad et al.; "Performance of the Aptima High-Risk Human Papillomavirus MRNA Assay in a Referral Population in Comparison with Hybrid Capture 2 and Cytology"; Journal of Clinical Microbiology; Mar. 2011; LNKD-PUBMED:21191046; vol. 49; No. 3; Dec. 29, 2010; p. 1071-1076; Abstract
Li et al; Detection of Human Papillomavirus Genotypes With Liquid Bead Microarray in Cervical Lesions of Northern Chinese Patients; Cancer Genetics and Cytogenetics, Elsevier Science Publishing, New York, NY, US, vol. 182; No. 1; Mar. 6, 2008; pp, 12-17; Abstract.
Gheit et al.; "Development of a Sensitive and Specific Assay Combining Multiplex PCR and DNA Microarray Primer Extension to Detect High-Risk Mucosal Human Papillomavirus Types"; Journal of CLinical Microbiology, American Society for Microbiology, Washington, DC, US ; vol. 44; No. 6; Jun. 1, 2006; pp. 2025-2031; Abstract
Han et al.; "Simultaneous Amplification and Identification of 25 Human Papillomavirus Types with Templex Technology"; Journal of Clinical Microbiology 200611 US LNKD- DOI:10.1128/JCM.01762-06; vol. 44; No. 11; Nov. 2006; pp. 4157-4162; Abstract
Database EMBL [Online]; Jul. 19, 2007; "Sequence 25 from Patent EP1806410"; XP002675256; Retrieved from EBI Accession No. EMBL:CS642417; Database Accession No. CS642417; The Whole Document.
Database EMBL [Online]; Dec. 14, 2010; "Sequence 26 from Patent US 7812144"; XP00267527; Retrieved from EBI Accession No. EMBL:GX640151; Database Accession No. GX640151; The Whole Document.
Database Geneseq [Online]; Jan. 22, 2009; "HPV-16 E7/E6 Gene Target Sequence, Bases 752-744"; XP002675258, Retrieved from EBI Accession No. GSN:AT82292; Database Accession No. ATS82292; The Whole Document.
Database Geneseq [Online]; Jan. 22, 2009; "HPV-16 E71E6 Gene Target Sequence, Bases 698-720"; XP002675259 Retrieved from EBI Accession No. GSN:ATS82290; Database Accession No. ATS82290; The Whole Document.
Database Geneseq [Online]; Apr. 1, 2010; "HPV16 E7 Gene Forward RT-PCR Primer Seq ID 49"; XP002675260; Retrieved from EBI Accession No. GSN:AXU96631; Database Accession No. AXU96631; The Whole Document.
Database Geneseq [Online]; Apr. 21, 2005; "E7 Coding Region (1-87) Amplifying Sense PCR Primer, Seq ID No: 37"; XP002675261; Retrieved from EBI Accession No. GSN:ADX15568; Database Accession No. ADX15568; Sequence.
Supplementary European Search Report of PCT/US2006/060603, dated Jul. 7, 2010 (8 pages).

(56) References Cited

OTHER PUBLICATIONS

International Search Report and Written Opinion of PCT/US2010/022264 dated Jun. 7, 2010 (19 pages).
Cohenford et al., "C-195. Rapid Detection of Chlamydia trachomatis from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.
Gentech Diagnostics: "Chlamydia DNA Test Kit," (Jun. 6, 2008), XP002578832, Retrieved from the Internet: URL: http://www.gentechin.com/chlamydiatestkit.htm.
Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.
Darwin et al., "Comparison of Digene Hybrid Capture 2 and Conventional Culture for Detection of Chlamydia trachomatis and Neisseria gonorrhoeae in Cervical Specimens," Journal of Clinical Microbiology, (Feb. 2002), pp. 641-644, vol. 40, No. 2, XP002578833.
Nazarenko et al., "A novel method of HPV genotyping using Hybrid Capture sample preparation method combined with GP5+/6+ PCr and multiplex detection on Luminex XMAP," Journal of Clinical Virology, (Dec. 1, 2008), pp. 76-81, vol. 154, No. 1-2, XP025680302.
International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6. (Note that the page number of this literature listed on the ISR is incorrect).
Vernick et al., "The HPV DNA virus hybrid capture assay: What is it- and where do we go from here?" MLO Med. Lab. Obs., (Mar. 2003), pp. 8-10, 13, vol. 35, No. 3.
International Search Report for PCT/US20091062041, dated Mar. 31, 2010 (17 pages).
Partial International Search Report for PCT/US2009/062061, mail date Jan. 5, 2010.
Partial International Search Report for PCT/US2009/062041, mail date Jan. 5, 2010.
Bhan P, et al., "2', 5'-linked oligo-3'-deoxyribonucleoside phosphorothioate chimeras: thermal stability and antisense inhibition of gene expression," Nucleic Acids Research Aug. 15, 1997, vol. 25, No. 16, pp. 3310-3317, XP002560367, ISSN: 0305-1048, p. 3313.
Genetech Diagnostics Pvt. Ltd., "Digene HBV Test Hybrid Capture II," Jun. 6, 2008, XP-00256068, retrieved from internet: URL:http://www.gentechin.com/hbvdnatestkit.htm>.
Hantz S, et al., "[Evaluation of accuracy of three assays for human papillomavirus detection and typing: Hybrid Capture 2, HPV Consensus kit and Amplicor HPB.]," Pathologie-Biologie, Feb. 2008, vol. 56, No. 1, Feb. 2008, pp. 29-35, XP 002560369, ISSN: 0369-8114.
Sandri et al., "Comparison of the Digene HC2 Assay and the Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146, XP002560370, ISSN: 0095-1137.
Boston Bioproducts Inc., "Protein Extraction buffers," Sep. 2, 2007, XP002560371, Retrieved from the Internet: URL: http://www.bostonbioproducts.com/product_disply1.php?page=20&limit=10&id=4>.
Bart "General Principles of Immunoprecipitation," Jul. 31, 2008, XP002560372, URL:http://pingu.salk.edu/{sefton/Hyper_protocols/immunoprecip.html>.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly(dT) And Poly(I) Poly(dC) As Immunogens For The Induction Of Antibodies To RNA-DNA Hybrids," Molecular Immunology, vol. 19, No. 3, pp. 413-420, 1982.
Ishikawa et al., "Enzyme-Labeling of Antiboldies and Their Fragments for Enzyme Immunoassay and Immunohistochemical Staining," Journal of Immunoassay and Immunochemistry, 4: 3, 209-327.
Means et al., "Chemical Modifications of Proteins: History and Applications," Bioconjugate Chem. 1990, 1, 2-12.
Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.
Jakobovits et al., "Germ-line transmission and expression of a human-derived yeast artificial chromosome," pp. 255-258, Nature, vol. 362, Mar. 18, 1993.
U.S. Appl. No. 12/588,304, titled "Automated Assay and System," filed Oct. 9, 2009 (not yet published).
U.S. Appl. No. 12/588,306, titled "Open Platform Automated Sample Processing System," filed Oct. 9, 2009 (not yet published).
U.S. Appl. No. 12/622,131, titled "Multiple-Input Analytical System," filed Nov. 19, 2009 (not yet published).
U.S. Appl. No. 12/605,540, titled "Fast Results Hybrid Capture Assay and System," filed Oct. 26, 2009 (not yet published).
U.S. Appl. No. 12/605,605, titled "Fast Results Hybrid Capture Assay on an Automated Platform," filed Oct. 26, 2009 (not yet published).
International Search Report for PCT/US2009/041033, dated Deember 22, 2009.
Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al., "Classification of papillomarviruses," In: Virology, Jun. 2004, vol. 324(1), pp. 17-27—see table 3.
GenBank Accession No. K02718, "Human papillomavirus type 16 (HPV16), complete genome.", Mar. 18, 1994. See http://www.ncbi.nlm.nihgov/nuccore/333031.
GenBank Accession No. X74479, "human papillomavirus type 45 genomic DNA.", Apr. 18, 2005. See http://www.ncbi.nlm.nih.gov/nuccore/397022.
GenBank Accession No. X05015, "Human papillomavirus type 18 E6, E7, E1, E2, E4, E5, L1 & L2 genes.", Apr. 18, 2005. See http://www.ncbi.nlm.nih.gov/nuccore 60975.
GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002. See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999. See http://www.ncbi.nlm.nih.gov/nuccore/333087.
GenBank Accession No. X74481, "Human papillomavirus type 52 genomic DNA.", Apr. 18, 2005. See http://www.ncbi.nlm.nih.gov/nuccore/397038.
GenBank Accession No. X74483, "Human papillomavirus type 56 genomic DNA.", Apr. 18, 2005. See http://www.ncbi.nlm.nih.gov/nuccore/397053.
GenBank Accession No. D90400, "Human papillomavirus type 58, complete genome.", Dec. 7, 2007. See http://www.ncbi.nlm.nih.gov/nuccore/222386.
GenBank Accession No. X77858, "Human papillomavirus type 59, complete viral genome.", Apr. 18, 2005. See http://www.ncbi.nlm.nih.gov/nuccore/557236.
GenBank Accession No. U31794, "Human papillomavirus type 66, complete genome.", Oct. 18, 1995. See http://www.ncbi.nlm.nih.gov/nuccore/1020290.
GenBank Accession No. X67161, "Human papillomavirus type L1 gene for major capsid protein.", Apr. 18, 2005. See http://www.ncbi.nlm.nih.gov/nuccore/1197494.

(56) References Cited

OTHER PUBLICATIONS

GenBank Accession No. AB027021, "Human papillomavirus type 82 DNA, complete genome.", Jun. 22, 2000. See http://www.ncbi.nlm.nih.gov/nuccore/6970427.
Kleter et al., "Development and clinical evaluation of a highly sensitive PCT-reverse hybridization line probe assay for detection and identification of anogenital human papillomafirus," In: Journal of clinical Micorbiology, Aug. 1999, vol. 37(8), pp. 2508-2517.
Communication received from the European Patent Office pursuant to Application No. 01 944 578.2-2402.
Murakami et al. Fluorescent-labeled oligonucleotide probes: detection of hybrid formation in solution by fluorscence polarization spectroscopy. Nucleic Acids Res., vol. 19, Np. 15, pp. 4097-4102, 1991.
Casademont et al., 2000 "Rapid Detection of *Campylobacter* fetus by Polymerase Chain Reaction Combined With Non-Radioactive Hybridization Using an Oligonucleotide Covalently Bound to Microwells" Molecular and Cellular Probes 14:233-240.
Coutlee et al., "Nonisotopic Detection of RNA in an Enzyme Imunoassay using a Monoclonal Antibody Against DNA-RNA Hybrids" Analytical Biochemistry 181:153-162, 1989.
Chen et al., "DNA Optical Sensor: A Rapid Method For The Detection Of DNA Hytordization" Biosensors & Bioelectronics 13:451-458, 1998.
Chevrier et al., "Isolation of a Specific DNA fragment and Development of a PCR-Based Method for the Detection of *Mycobacterium genavense*" FEMS Immunology and Medical Microbiology 23:243-452, 1999.
Hakala et al., "Simultaneous Detection Of Several Oligonucleotides By Time-Resolved Fluorometry: The Use Of A Mixture Of Categorized Microparticles In A Sandwich Type Mixed-Phase Hybridization Assay" Nucleic Acids Research, 26:5581-5588, 1998.
Gelmetti et al., "Detection of Rabbit Haemorrhagic Disease Virus (RHDV) by In Situ Hybridisation With A Digoxigenin Labelled RNA Probe" Journal of Virological Methods 72:219-226, 1998.
Radtkey et al., "Rapid, High Fidelity Analysis of Simple Sequence Repeats On An Electronically Active DNA Microchip" Nucleic Acids Research 28:i-vi, 2000.
Namimatsu et al., "Detection of *Salmonella* by Using the Colorimetric DNA/rRNA Sandwich Hybridization in Microtiter Wells" J. Vet. Med. Sci. 62:615-619, 2000.
Lazar et al., 1999 "Hybrid Capture RTM.: a Sensitive Signal Amplification-based Chemiluminescent Test for the Detection and Quantitation of Human Viral and Bacterial Pathogens" J. Clin. Ligand Assay 22:139-151.
Newman et al., 1989 "Solution Hybridization and Enzyme Immunoassay for Biotinylated DNA:RNA Hybrids to Detect Enteroviral RNA in Cell Culture" Mol. Cell Probes 3:375-382.
Lamoureux et al., 1997 "Detection of *Campylobacter jejuni* in Food and Poultry Viscera Using Immunomagnetic Separation and Mictotitre Hybridization" J. Appl. Microbiol. 83:641-651.
Coutlee et al., 1990 "Quantitative Detection of Messenger RNA by Solution Hybridization and Enzyme Immunoassay" J. Biol. Chem. 265:11601-11604.
Stollar, B.D. and A. Rashtchian, 1987 "Immunochemical Approaches to Gene Probe Assays" Anal. Biochem. 161;387-394.
Blais, B.W., 1994 "Transcriptional Enhancement of the *Listeria monocytogenes* PCR and Simple Immunoenzymatic Assay of the Product Using Anti-RNA:DNA Antibodies" Appl. Environ. Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microblol. 27:120-125.
Boguslawski et al., 1986 "Characterization of Monoclonal Antibody to DNA:RNA and Its Application to Immunodetection of Hybrids" J. Immunol. Methods 89:123-130.
Coutlee et al., 1989 "Immunodetection of DNA with Biotinylated RNA Probes: A Study of Reactivity of a Monoclonal Antibody to DNA-RNA Hybrids" Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Colorimetric Fluorescent, and Enzymatic Amplification Substrate Systems in an Enzyme Immunoassay for Detection of DNA-RNA Hybrids" J. Clin. Microbiol. 27:1002-1007.
Zientara et al., 1998 "Use of reverse transcriptase-polymerase chain reaction (RT-PCR) and dot-blot hybridization for the detection and identification of African horse sickness virus nucleic acids" Arch Virol 14:317-327.
Mansy et al., 1999 "A PCR Based DNA Hybridisation Capture System for the Detection of Human Cytomegalovirus. A Comparative Study with Other Identification Methods" Journal of Virological Methods 80:113-122.
Poulsen et al., 1999 "Detection of Clinical Vancomycin-Resistant Enterococci in Denmark by Multiplex PCR and Sandwich Hybridization" APMIS 107:404-12.
Sjoroos et al., 1998 "Time-Resolved Fluorometry Based Sandwich Hybridisation Assay for HLA-DQA1 Typing" Disease Markers 14:9-19.
Edman et al., 2000 "Pathogen Analysis and Genetic Predisposition Testing Using Microelectronic Arrays and Isothermal Amplification" Journal of Investigative Medicine, 48:93-101.
Monteiro et al.,1997 Evaluation of Performances of Three DNA Enzyme Immunoassays for Detection of *Helicobacter pylori* PCR Products from Biopsy Specimens Journal of Clinical Microbiology, 35:2931-2936.
Chiu et al., 1998 "Sandwich-type Deoxyribonucleic Acid Hybridization Assays Based on Enzyme Amplified Time-Resolved Fluorometry" Analyst., 123:1315-1319.
White et al., 1999 "Signal Amplification System for DNA Hybridization Assays Based on in vitro Expression of a DNA Label Encoding Apoaequorin" Nucleic Acids Research 27:i-viii.
Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.
Zammatteo et al., 1997 "Comparison between Microwell and Bead Supports for the Detection of Human Cytomegalovirus Amplicons by Sandwich Hybridization" Analytical Biochemistry 253:180-189.
Fisher et al., 1997 "A System for the Quantitation of DNA Using a Microtiter Plate-Based Hybridization and Enzyme Amplification Technology" Analytical Biochemistry 251:280-287.
Wicks et al., 1998 "A Sandwich Hybridization Assay Employing Enzyme Amplification for Determination of Specific Ribosomal RNA from Unpunfied Cell Lysates" Analytical Biochemistry 259:258-264.
Bruckner-Lea et al., 2000 "Rotating Rod Renewable Microcolumns for Automated, Solid-Phase DNA Hybridization Studies" Anal. Chem. 72:4135-4141.
Allen et al., 1998 "High Resolution Genetic Typing of the Class II HLA-DRB1 Locus Using Group-Specific Amplification and SSO-Hybridisation in Microplates" Hereditas 129:161-167.
Chomvarin et al., 2000 "Development of EIA for Detection of *Chlamydia trachomatis* in Genital Speciments" The Southeast Asian Journal of Tropical Medicine and Public Health, 31:96-103.
Alexandre et al., 1998 "Quantitative Determination of CMV DNA Using a Combination of Competitive PCR Amplification and Sandwich Hybridization" BioTechniques, 25: 676-683.
McGeoch et al. "Structures of Herpes Simplex Virus Type 1 Genes Required for Replication of Virus DNA" J. Virol. vol. 62, No. 2, pp. 444-453.
Larder et al. "Related functional domains in virus DNA polymerases", The EMBO J., 1987, vol. 8, No. 1, pp. 169-175.
McGeoch et al. "The Complete DNA Sequence of the Long Unique Region in the Genome of Herpes Simplex Virus Type I", J. Gen. Virol., 1998, vol. 69, pp. 1531-1574.
Yamada et al "Human Papillomavirus Type 16 Variant Lineages in United States Populations Characterized by Nucleotide Sequence

(56) References Cited

OTHER PUBLICATIONS

Analysis of the E6, L2, and L1 Coding Segments", J. Virol. Dec. 1995, vol. 69, No. 12, pp. 7743-7753.

McGeoch et al. DNA Sequence and Genetic Content of the HindIII 1 Region in the Short Unique Component of the Herpes Simplex Virus Type 2 GenomeI Identification of the Gene Encoding Glycoprotein G, and Evolutionary Comparisons J. Gen. Virol. 1987, vol. 68, pp. 19-38.

McLauchlan et al. "DNA sequence homology between two co-linear loci on the HSV genome which have different transforming abilities" The EMBO Journal, 1983, vol. 2, No. 11, pp. 1953-1961.

Dalrymple et al. "DNA Sequence of the herpes simplex virus type 1 gene whose product is responsible for transcriptional activation of immediate early promoters", Nucleic Acids Research, 1985, vol. 13, No. 21, pp. 7865-7879.

EPO Form 1507.4 (Supplementary European Search Report)., Aug. 2004.

International Search Report of PCT/US06/60603 mailed Sep. 11, 2007.

Swain M.A. et al., "Nucleotide sequence of the herpes simplex virus type 2 thymidine kinase gene," J. Virol., vol. 46. No. 3:1045-1050m espically p. 1047, Jun. 1983.

Goldsborough et al., "Nucleotide sequence of human papillomavirus type 31: A cervical neoplasia-associated virus," Virology, Vo. 171, pp. 308-311, 1989.

Delius H. et al., "Primer-directed seuencing of human papillomavirus types," Curr. Top. Microbiol. Immunol., Vo. 186: pp. 13-31, especially p. 16, 1994.

Dunn et al., "A Novel Method to Map Transcnpts: Evidence for Homology between an Adenovirus mRNA and Discrete Mulitiple Regions of hte Viral Genome" Cell, vol. 12, pp. 23-38, Sep. 1977.

Blair et al., "Herpes Simplex Virus Viron Stimulatory Protein mRNA Leader Contains Sequence Elements Which Increase Both Virus-Induced Transcription and mRNA Stability", Journal of Virology, vol. 81, No. 8, pp. 2499-2508, Aug. 1987.

Broker et al., "A Molecular Portrait of Human Papillomavirus Carcinogenesis", Cancer Cells. vol. 7, pp. 197-208, 1989.

Higgins et al., "Transcription Patterns of Human Papillornavirus Type 16 in Genital Intraepithelial Neoplasla: Evidence for Promoter Usage within the E7 Open Reading Frame during Epithelial Differentiation", Journal of General Virology, vol. 73, pp. 2047-2057, 1992.

Karlsen et al., "Use of Multiple PCR Primer Sets forOptimal Detection of Human Papillomavirus", Journal of Clinical Microbiology, pp. 2095-2100, Sep. 1996.

Park et al., "Physical Status and Expression of HPV Genes in Cervical Cancers", Gnyecologic Oncology, vol. 65, pp. 121-129, 1997.

Stoler et al., "Human Papillomavirus Type 16 and 18 Gene Expression in Cervical Neoplasias", Human Pathology, vol. 23, No. 2, pp. 117-128, Feb. 1992.

De Villiers et al., "Classification of Papillomaviruses", Virology, vol. 324, pp. 17-27, 2004.

Howley et al., "A Rapid Method for Detecting and Mapping Homology between Heterologous DNAs", Journal of Biological Chemistry, vol. 254, No. 11, pp. 4879-1883, Jun. 10, 1979.

Law et al., "Conserved Polynucleotide Sequences Amonth the Genomics of Papillomaviruses", Journal of Virology, vol. 32, No. 1, pp. 199-207, Oct. 1979.

Heilman et al., "Clonging of Human Papilloma Virus Genomic DNAs and Analysis of Homologous Polynucleotide Sequences", Journal of Virology, vol. 36, No. 2, pp. 395-407, Nov. 1980.

Howard et al., "Optimizing the Hybrid Capture II Human Papillomavirus Test to Detect Cervical Intraepithelial Neoplasia", Obstetrics and Gynecology, No. 10, No. 5, Part 1, pp. 972-980, Nov. 2002.

Lorincz, A. T., Molecular Methods for the Detection of Human Papillomavirus Infection:, Obstetrics and Gynecology Clinics of North America, vol. 23, No. 3, pp. 707-730, Sep. 1996.

B.D. Hames, et al., "Nucleic Acid Hybridization. A Practical Approach." 1985.

Greg T. Hermanson, et al., "Immobilized Affinity Ligand Techniques." 1992.

Richard F. Taylor, "Protein Immobilization. Fundamentals and Applications." 1991.

Hara et al., "Small Sample Whole-Genome Amplification", Optics East 2005, UCRL-PROC-216415, Lawrence Livermore National Laboratory, Oct. 21, 2005.

Brigotti, et al., Necleic Acids Res., vol. 26, No. 18, pp. 4306-4307, 1998.

Blair et al., "Herpes Simplex Virus Viron Stimulatory Protein mRNA Leader Contains Sequence Elements Which Increase Both Virus-Induced Transcription and mRNA Stability", Journal of Virology, No. 61, No. 8, pp. 2499-2508, Aug. 1987.

Mazzulli et al., Multicenter comparison of the Digene hybrid capture CMV DNA assay (version 2.0), the pp65 antignenemia assay, and cell culture for detection of cytomegalovirus viremia. J Clin. Microbiol., vol. 37, No. 4, pp. 958-963, 1999.

Chandler et al., Detection of dengue-2 viral RNA by reversibletarget capture hybridization. J. Clin Microbiol., vol. 31, No. 10, pp. 2641-2647, 1993.

* cited by examiner

TSHC with "Fused" Capture Sequence Probes (CSP)

Capture with two separate CSPs

Capture with two separate fusion CSPs

Capture with a single fusion CSP

······ Unique Sequences
—— Signal Sequence Probe

DETECTION OF NUCLEIC ACIDS BY TARGET-SPECIFIC HYBRID CAPTURE METHOD

CROSS REFERENCE TO RELATED APPLICATIONS

This application is a divisional of U.S. Ser. No. 12/253,976 (filed Oct. 19, 2008), which is a divisional of U.S. Ser. No. 09/594,839 (filed Jun. 15, 2000; issued as U.S. Pat. No. 7,439,016), the contents of which are incorporated herein by reference in their entirety.

FIELD OF INVENTION

This invention relates to the field of nucleic acid detection methods in general and more particularly relates to the detection of nucleic acids by target-specific hybrid capture method.

BACKGROUND OF THE INVENTION

The detection of specific nucleic acid sequences present in a biological sample is important for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting and quantitating specific nucleic acid sequences is nucleic acid hybridization.

Various hybridization methods are available for the detection and study of nucleic acids. In a traditional hybridization method, the nucleic acids to be identified are either in a solution or affixed to a solid carrier. The nucleic acids are detected using labelled nucleic acid probes which are capable of hybridizing to the nucleic acids. Recently, new hybridization methods have been developed to increase the sensitivity and specificity of detection. One example is the hybrid capture method described in U.S. application Ser. No. 07/792,585. Although these new hybridization methods offer significant improvements over the traditional methods, they still lack the ability to fully discriminate between highly homologous nucleic acid sequences.

It is therefore an object of the present invention to provide a hybridization method which is not only rapid and sensitive, but is also highly specific and capable of discriminating highly homologous nucleic acid target sequences.

SUMMARY OF THE INVENTION

The present invention provides a novel nucleic acid detection method, referred to herein as target-specific hybrid capture ("TSHC"). TSHC is a highly specific and sensitive method which is capable of discriminating and detecting highly homologous nucleic acid target sequences.

In one embodiment, the method relates to detecting a target nucleic acid wherein the targeted nucleic acid is hybridized simultaneously, or sequentially, to a capture sequence probe and an unlabelled signal sequence probe. These probes hybridize to non-overlapping regions of the target nucleic acid and not to each other so that double-stranded hybrids are formed. The hybrids are captured onto a solid phase and detected. In a preferred embodiment, an DNA-RNA hybrid is formed between the target nucleic acid and the signal sequence probe. Using this method, detection may be accomplished, for example, by binding a labeled antibody capable of recognizing an DNA-RNA hybrid to the double-stranded hybrid, thereby detecting the hybrid.

In another embodiment, the signal sequence probe used in the detection method is a nucleic acid molecule which comprises a DNA-RNA duplex and a single stranded nucleic acid sequence which is capable of hybridizing to the target nucleic acid. Detection may be accomplished, for example, by binding a labeled antibody capable of recognizing the DNA-RNA duplex portion of the signal sequence probe, thereby detecting the hybrid formed between the target nucleic acid, the capture sequence probe and the signal sequence probe.

In yet another embodiment, the signal sequence probe used in the detection method is a molecule which does not contain sequences that are capable of hybridizing to the target nucleic acid. Bridge probes comprising sequences that are capable of hybridizing to the target nucleic acid as well as sequences that are capable of hybridizing to the signal sequence probe are used. In this embodiment, the signal sequence probe comprises a DNA-RNA duplex portion and a single stranded DNA sequence portion containing sequences complementary to sequences within the bridge probe. The bridge probe, which hybridizes to both the target nucleic acid and the signal sequence probe, therefore serves as an intermediate for connecting the signal sequence probe to the target nucleic acid and the capture sequence probe hybridized to the target nucleic acid.

In another embodiment of the TSHC method of the invention, blocker probes comprising oligonucleotides complementary to the capture sequence probes are used in the method to eliminate excess capture sequence probe, thereby reducing the background signal in detection and increasing specificity of the assay.

The present invention also relates to novel probes. These probes are nucleic acid sequences which can function in various hybridization assays, including, for example, the TSHC assay.

DETAILED DESCRIPTION OF THE INVENTION

Figure 1:
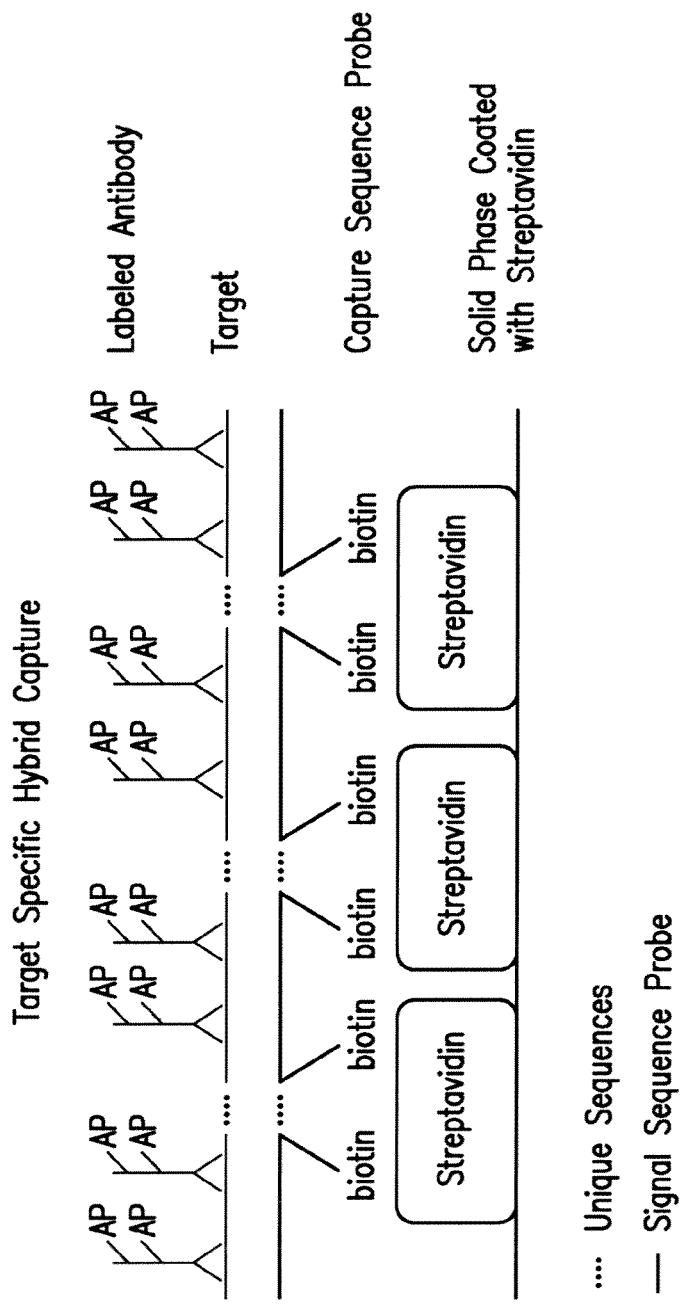
FIG. 1 is a schematic diagram illustrating one embodiment of the target-specific hybrid capture method.
Figure 2:
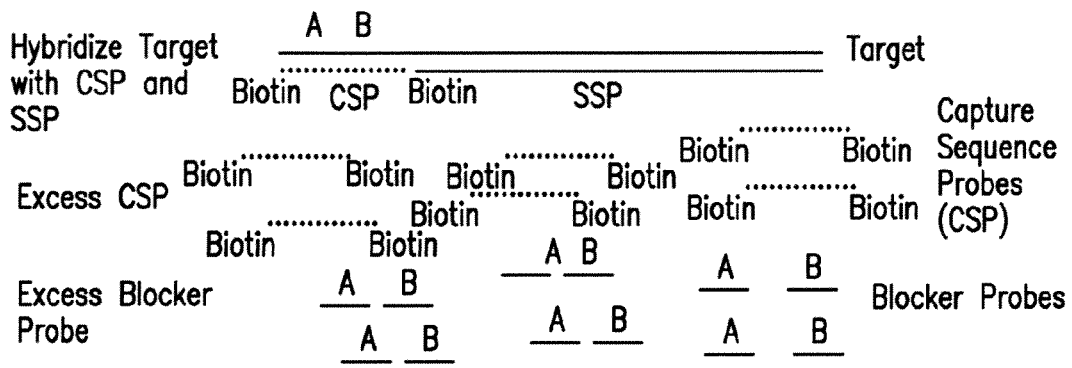
FIG. 2 is a schematic diagram illustrating one embodiment of the target-specific hybrid capture method.
Figure 2:
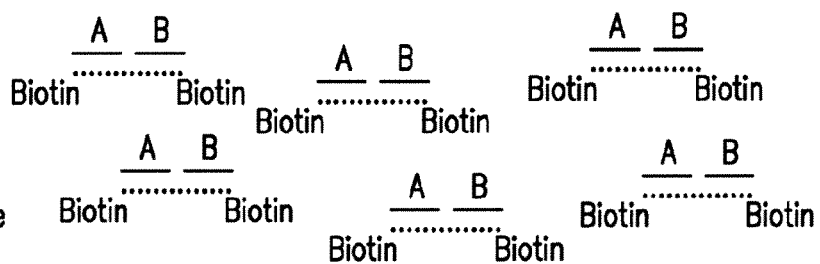
Figure 2:
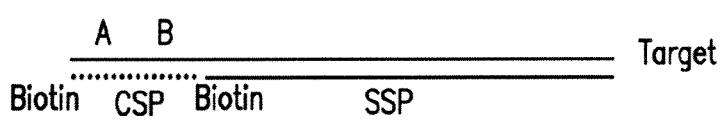
Figure 3:
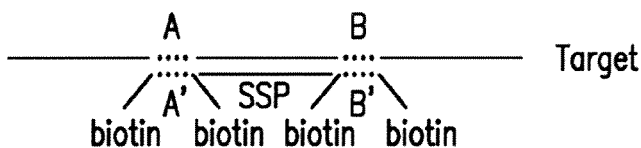
FIG. 3 is a schematic diagram illustrating possible mechanisms of action of an embodiment that employs fused capture sequence probes in target-specific hybrid capture detection.
Figure 3:
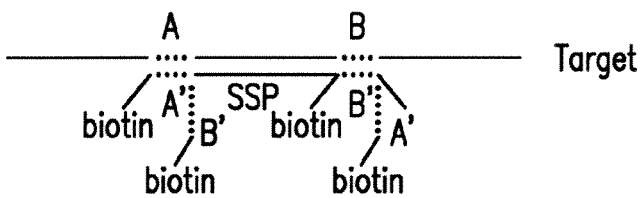
Figure 3:
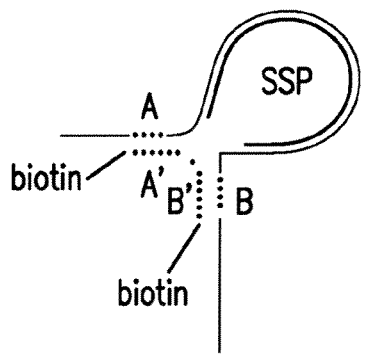

The present invention provides a method for detecting the presence of nucleic acids in test samples. More specifically, the invention provides a highly specific and sensitive method which is capable of discriminating and detecting highly homologous nucleic acid sequences.

Any source of nucleic acid, in purified or non-purified form, can be utilized as the test sample. For example, the test sample may be a food or agricultural product, or a human or veterinary clinical specimen. Typically, the test sample is a biological fluid such as urine, blood, plasma, serum, sputum or the like. Alternatively the test sample may be a tissue specimen suspected of carrying a nucleic acid of interest. The target nucleic acid in the test sample may be present initially as a discrete molecule so that the sequence to be detected constitutes the entire nucleic acid, or may only be a component of a larger molecule. It is not necessary that the nucleic acid sequence to be detected be present initially in a pure form. The test sample may contain a complex mixture of nucleic acids, of which the target nucleic acid may correspond to a gene of interest contained in total human genomic DNA or RNA or a portion of the nucleic acid sequence of a pathogenic organism which organism is a minor component of a clinical sample.

The target nucleic acid in a test sample can be DNA or RNA, such as messenger RNA, from any source, including bacteria, yeast, viruses, and the cells or tissues of higher organisms such as plants or animals. Methods for the extraction and/or purification of such nucleic acids are well known in the art. Target nucleic acids may be double-stranded or single-stranded. In the present method, it is preferred that the target nucleic acids are single-stranded or made single-stranded by conventional denaturation techniques prior to the hybridization steps of the method. In a preferred embodiment, base denaturation technique is used to denature the double-stranded target DNA.

The term "oligonucleotide" as the term is used herein refers to a nucleic acid molecule comprised of two or more deoxyribonucleotides or ribonucleotides. A desired oligonucleotide may be prepared by any suitable method, such as purification from a naturally occurring nucleic acid, by molecular biological means, or by de novo synthesis. Examples of oligonucleotides are nucleic acid probes described herein.

Nucleic acid probes are detectable nucleic acid sequences that hybridize to complementary RNA or DNA sequences in a test sample. Detection of the probe indicates the presence of a particular nucleic acid sequence in the test sample. In one embodiment, the target-specific hybrid capture method employs two types of nucleic acid probes: capture sequence probe (CSP) and signal sequence probe (SSP). A capture sequence probe comprises a nucleic acid sequence which is capable of hybridizing to unique region(s) within a target nucleic acid and being captured onto a solid phase. A signal sequence probe comprises a nucleic acid sequence which is capable of hybridizing to regions within a target nucleic acid that are adjacent to the unique regions recognized by the CSP. The sequences of CSP and SSP are selected so that they would not hybridize to the same region of a target nucleic acid or to each other.

In addition, the CSP and the SSP are selected to hybridize to regions of the target within 50,000 bases of each other. The distance between the sequence to which the CSP hybridizes within the target nucleic acid and the sequence to which the SSP hybridizes is preferably between 1 to 50,000 bases, more preferably, the distance is less than 3,000 bases. Most preferably, the distance is less than 1,000 bases.

The CSP used in the detection method can be DNA, RNA, peptide nucleic acids (PNAs) or other nucleic acid analogues. PNAs are oligonucleotides in which the sugar-phosphate backbone is replaced with a polyamide or "pseudopeptide" backbone. In a preferred embodiment, the CSP is DNA. The CSP has a minimum length of 8 bases, preferably between 15 to 100 bases long, and more preferably between 20 to 40 bases long. The CSP is substantially complementary to the sequence within a target nucleic acid to which it hybridizes. The sequence of a CSP is preferably at least 75% complementary to the target hybridization region, more preferably, 100% complementary to this sequence. It is also preferred that the CSP contains less than or equal to 75% sequence identity, more preferably less than 50% sequence identity, to non-desired sequences believed to be present in a test sample. The sequence within a target nucleic acid to which a CSP binds is preferably 12 bases long, more preferably 20-40 bases long. It may also be preferred that the sequences to which the CSP hybridizes are unique sequences or group-specific sequences. Groupspecific sequences are multiple related sequences that form discrete groups.

In one embodiment, the CSP used in the detection method may contain one or more modifications in the nucleic acid which allows specific capture of the probe onto a solid phase. For example, the CSP may be modified by tagging it with at least one ligand by methods well-known to those skilled in the art including, for example, nick-translation, chemical or photochemical incorporation. In addition, the CSP may be tagged at multiple positions with one or multiple types of labels. For example, the CSP may be tagged with biotin, which binds to streptavidin; or digoxigenin, which binds to anti-digoxigenin; or 2,4-dinitrophenol (DNP), which binds to anti-DNP. Fluorogens can also be used to modify the probes. Examples of fluorogens include fluorescein and derivatives, phycoerythrin, allo-phycocyanin, phycocyanin, rhodamine, Texas Red or other proprietary fluorogens. The fluorogens are generally attached by chemical modification and bind to a fluorogen-specific antibody, such as anti-fluorescein. It will be understood by those skilled in the art that the CSP can also be tagged by incorporation of a modified base containing any chemical group recognizable by specific antibodies. Other tags and methods of tagging nucleotide sequences for capture onto a solid phase coated with substrate are well known to those skilled in the art. A review of nucleic acid labels can be found in the article by Landegren, et al., "DNA Diagnostics-Molecular Techniques and Automation", Science, 242:229-237 (1988), which is incorporated herein by reference. In one preferred embodiment, the CSP is tagged with biotin on both the 5' and the 3' ends of the nucleotide sequence. In another embodiment, the CSP is not modified but is captured on a solid matrix by virtue of sequences contained in the CSP capable of hybridization to the matrix.

The SSP used in the detection method may be a DNA or RNA. In one particular embodiment of the invention, the SSP and target nucleic acid form a DNARNA hybrid. Therefore, in this embodiment, if the target nucleic acid is a DNA, then the preferred SSP is an RNA. Similarly, if the target nucleic acid is RNA, then the
preferred SSP is a DNA. The SSP is generally at least 15 bases long. However, the SSP may be up to or greater than 1000 bases long. Longer SSPs are preferred. The SSP may comprise a single nucleic acid fragment, or multiple smaller nucleic acid fragments each of which is preferably between 15 to 100 bases in length.

Figure 6A:
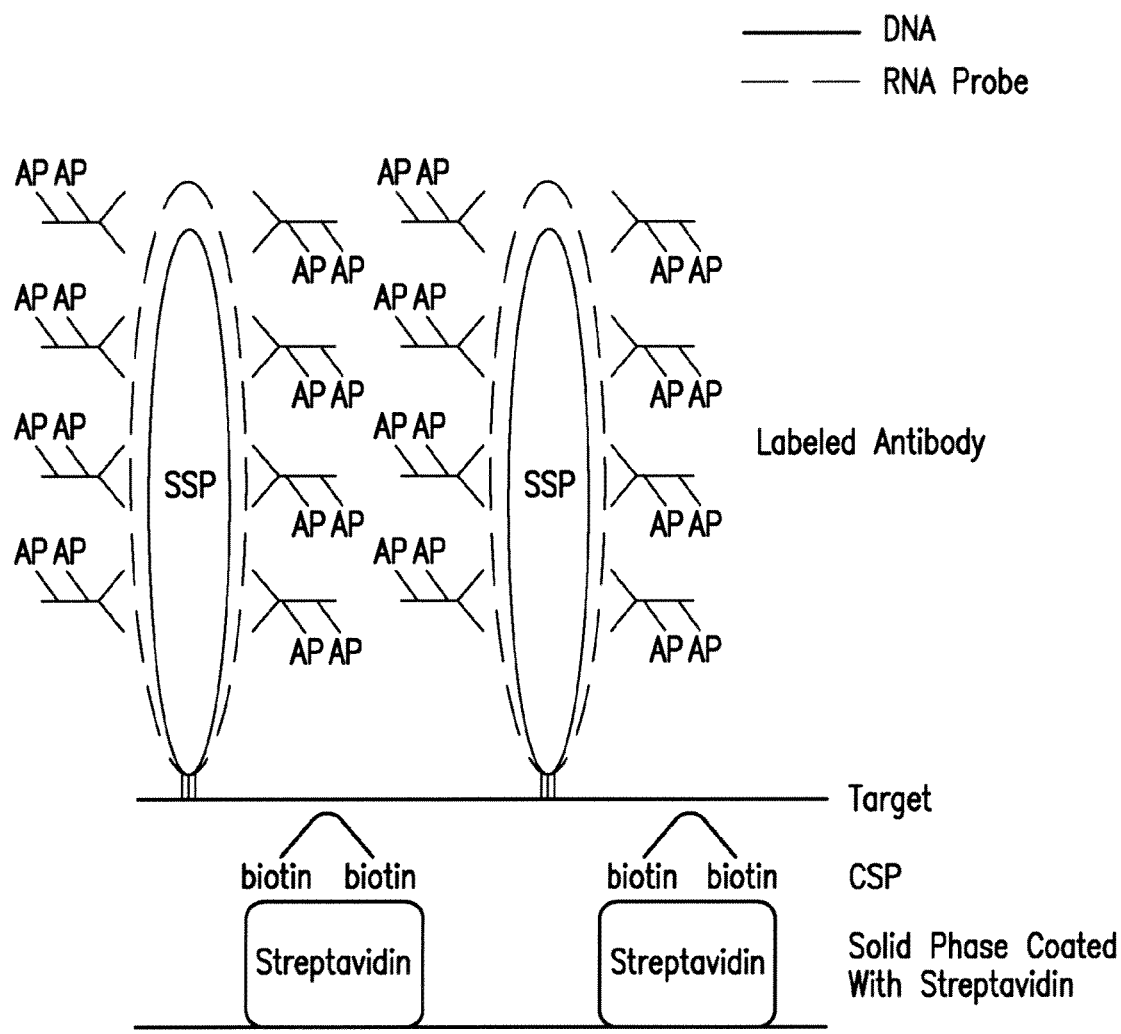
FIGS. 6A-6D show the various embodiments of the target-specific hybrid capture-plus method.

In another embodiment, the SSP used in the detection method comprises a DNA-RNA duplex and a single stranded nucleic acid sequence capable of hybridizing to the target nucleic acid (FIG. 6A). The SSP may be prepared by first cloning a single stranded DNA sequence complementary to sequences within the target nucleic acid into a single-stranded DNA vector, then hybridizing RNA complementary to the DNA vector sequence to generate a DNA-RNA duplex. For example, if M13 is used as the DNA vector, M13 RNA is hybridized to the M13 DNA sequence in the vector to generate a DNA-RNA duplex. The resulting SSP contains a DNA-RNA duplex portion as well as a single stranded portion capable of hybridizing to sequences within the target nucleic acid. The single stranded DNA should be at least 10 bases long, and may be up to or greater than 1000 bases long. Alternatively, the DNA-RNA duplex portion of the SSP may be formed during or after the reaction in which the single stranded portion of the SSP is hybridized to the target nucleic acid. The SSP can be linear, circular, or a combination of two or more forms. The DNARNA duplex portion of the SSP provides amplified signals for the detection of captured hybrids using anti-DNA-RNA antibodies as described herein.

Figure 6B:
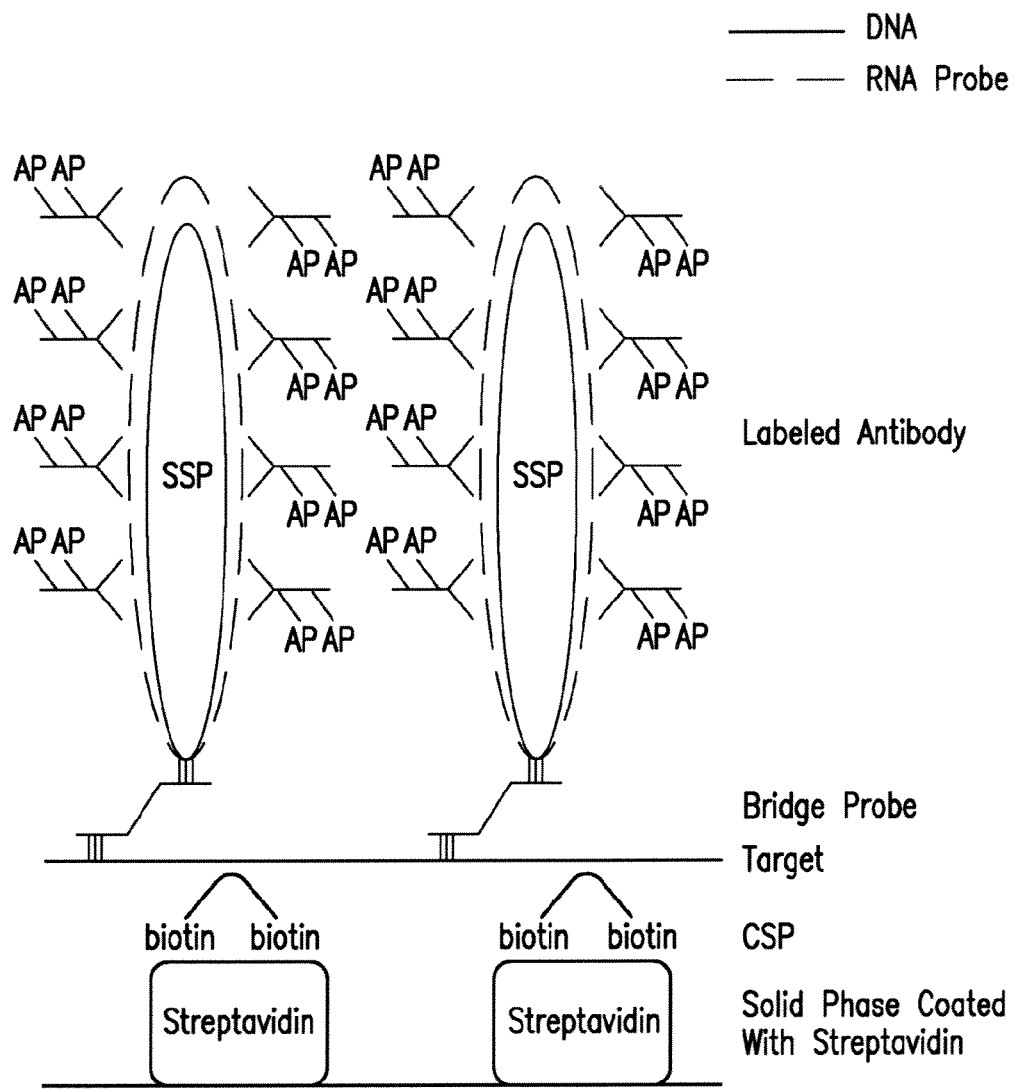
Figure 6C:
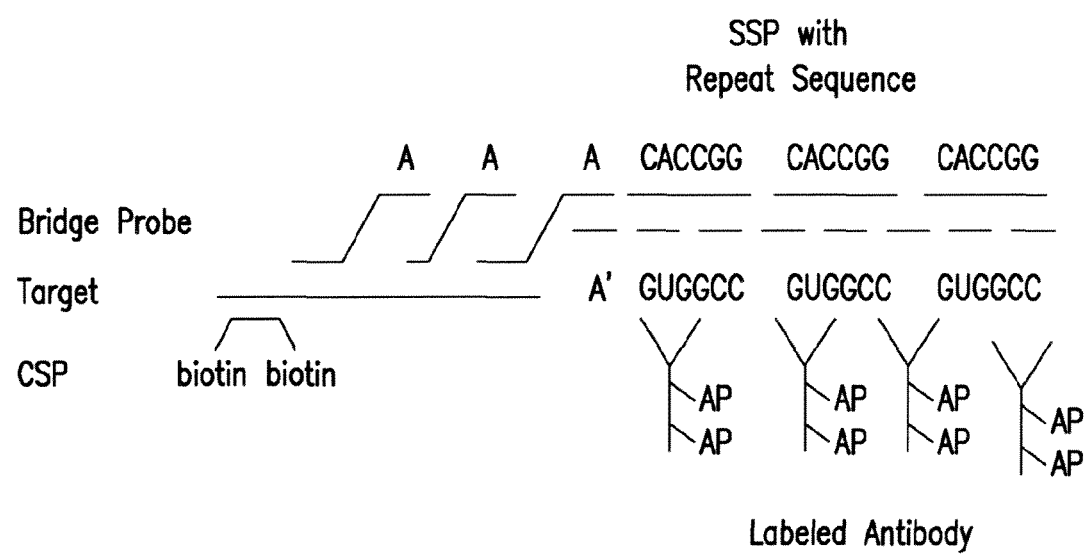
Figure 6D:
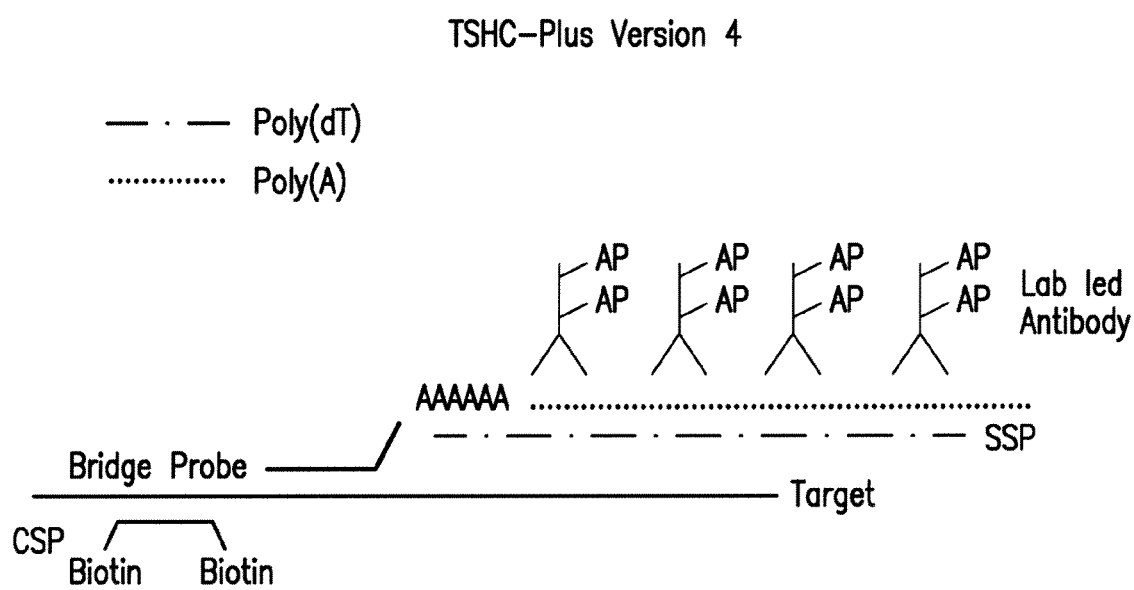

In yet another embodiment, the SSP used in the detection method is a molecule which does not contain sequences that are capable of hybridizing to the target nucleic acid. In this embodiment, bridge probes comprising sequences capable of hybridizing to the target nucleic acid as well as sequences capable of hybridizing to the SSP are used. The bridge probes can be DNA, RNA, peptide nucleic acids (PNAs) or other nucleic acid analogues. In one embodiment (FIG. 6B), the SSP comprises a DNA-RNA duplex portion and a single stranded portion containing sequences complementary to sequences within the bridge probe. The bridge probe, which is capable of hybridizing to both the target nucleic acid and the SSP, therefore serves as an intermediate for connecting the SSP to the target nucleic acid and the CSP hybridized to the target nucleic acid. The SSP may be prepared as described above. In another embodiment (FIG. 6C), the SSP used in the detection method comprises multiple sets of repeat sequences as well as a single stranded RNA sequence capable of hybridizing to the bridge probe. A DNA oligonucleotide probe containing sequences complementary to the repeat sequences may be used to hybridize to the SSP to generate the RNA-DNA duplex needed for signal amplification. In yet another embodiment (FIG. 6D), the bridge probe contains a poly(A) tail in addition to sequences which are capable of hybridizing to the target nucleic acid. The SSP used in this example comprises poly(dT) DNA sequences. The bridge probe therefore is capable of hybridizing to the SSP via its poly(A) tail. A RNA probe comprising poly(A) sequences may be used to hybridize to the remaining poly(dT) DNA sequences within SSP to form a RNA-DNA duplex. The SSP comprising poly(dT) sequences and the RNA probe comprising poly(A) sequences are preferably 100 to 5,000 bases long.

The SSP used in the detection method of the invention can be unmodified, or modified as with the CSP using methods described above and/or known in the art. In a preferred embodiment, the SSP is a covalently unmodified probe.

It is understood that multiple CSPs and/or SSPs can be employed in the detection method of the invention.

In another embodiment, an oligonucleotide probe comprising complementary sequences of two or more distinct regions of the target nucleic acid are fused together and used as the capture sequence probe in the method of the invention. Alternatively a single probe can be designed and produced which contains sequences complementary to single or multiple target nucleic acids. This type of probe is also referred to herein as a "fused" CSP. As shown in Example 5, the fused capture sequence probe works as effectively as the combination of two unfused CSPs when used at the same concentration.

The nucleic acid probes of the invention may be produced by any suitable method known in the art, including for example, by chemical synthesis, isolation from a naturally-occurring source, recombinant production and asymmetric PCR (McCabe, 1990 In: PCR Protocols: A guide to methods and applications. San Diego, Calif., Academic Press, 76-83). It may be preferred to chemically synthesize the probes in one or more segments and subsequently link the segments. Several chemical synthesis methods are described by Narang et al. (1979 Meth. Enzymol. 68:90), Brown et al. (1979 Meth. Enzymol. 68:109) and Caruthers et al. (1985 Meth. Enzymol. 154:287), which are incorporated herein by reference. Alternatively, cloning methods may provide a convenient nucleic acid fragment which can be isolated for use as a promoter primer. A double-stranded DNA probe is first rendered single-stranded using, for example, conventional denaturation methods prior to hybridization to the target nucleic acids.

Hybridization is conducted under standard hybridization conditions well-known to those skilled in the art. Reaction conditions for hybridization of a probe to a nucleic acid sequence vary from probe to probe, depending on factors such as probe length, the number of G and C nucleotides in the sequence, and the composition of the buffer utilized in the hybridization reaction. Moderately stringent hybridization conditions are generally understood by those skilled in the art as conditions approximately 25° C. below the melting temperature of a perfectly base-paired double stranded DNA. Higher specificity is generally achieved by employing incubation conditions having higher temperatures, in other words more stringent conditions. Chapter 11 of the well-known laboratory manual of Sambrook et al., MOLECULAR CLONING: A LABORATORY MANUAL, second edition, Cold Spring Harbor Laboratory Press, New York (1990) (which is incorporated by reference herein), describes hybridization conditions for oligonucleotide probes in great detail, including a description of the factors involved and the level of stringency necessary to guarantee hybridization with specificity. Hybridization is typically performed in a buffered aqueous solution, for which conditions such as temperature, salt concentration, and pH are selected to provide sufficient stringency such that the probes hybridize specifically to their respective target nucleic acid sequences but not any other sequence.

Generally, the efficiency of hybridization between probe and target improve under conditions where the amount of probe added is in molar excess to the template, preferably a 2 to $10^6$ molar excess, more preferably $10^3$ to $10^6$ molar excess. The concentration of each CSP provided for efficient capture is at least 25 fmoles/ml (25 pM) in the final hybridization solution, preferably between 25 fmoles to 104 fmoles/ml (10 nM). The concentration of each SSP is at least 15 ng/ml in the final hybridization solution, preferably 150 ng/ml. Table A shows the conversion of SSP concentrations expressed in ng/ml to molar basis.

TABLE A

Conversion of SSP Concentration From ng/ml to fmoles/ml

| SSP Concentration in ng/ml | SSP Concentration in fmoles/ml (pM) | |
| --- | --- | --- |
| | SSP is a 3 kb RNA | SSP is a 5 kb RNA |
| 15 ng/ml | 15.1 | 9 |
| 150 ng/ml | 151 | 90 |
| 600 ng/ml | 606 | 364 |

Hybridization of the CSP and the SSP to the target nucleic acid may be performed simultaneously or sequentially and in either order. In one embodiment, hybridization of the CSP and hybridization of the SSP to the target nucleic acid are performed simultaneously. The hybrid formed is then captured onto a solid phase coated with a substrate to which ligand attached to the CSP binds with specificity. In another embodiment, hybridization of the SSP to the target nucleic acid is performed after the hybridization of the CSP to the target nucleic acid. In this case, the CSP may be immobilized on a solid phase before or after hybridization. In this embodiment, both the CSP and the target may be bound to the solid phase during the SSP hybridization reaction.

It will be understood by those skilled in the art that a solid phase or matrix includes, for example, polystyrene, polyethylene, polypropylene, polycarbonate or any solid plastic material in the shape of plates, slides, dishes, beads, particles, cups, strands, chips and strips. A solid phase also includes glass beads, glass test tubes and any other appropriate glass product. A functionalized solid phase such as plastic or glass that has been modified so that the surface contains carboxyl, amino, hydrazide, aldehyde groups, nucleic acid or nucleotide derivatives can also be used. Any solid phase such as plastic or glass microparticles, beads, strips, test tubes, slides, strands, chips or microtiter plates can be used.

In one preferred embodiment, the CSP is labelled with biotin, and streptavidin-coated or avidin-coated solid phase is employed to capture the hybrid. More preferably, streptavidin-coated microtiter plates are used. These plates may be coated passively or covalently.

The captured hybrid may be detected by conventional means wellknown in the art, such as with a labelled polyclonal or monoclonal antibody specific for the hybrid, an antibody specific for one or more ligands attached to the SSP, a labelled antibody, or a detectable modification on the SSP itself.

One preferred method detects the captured hybrid by using an antiRNA-DNA antibody. In this embodiment, the anti-RNA-DNA antibody is preferably labelled with an enzyme, a fluorescent molecule or a biotin-avidin conjugate and is non-radioactive. The label can be detected directly or indirectly by conventional means known in the art such as a colorimeter, a luminometer, or a fluorescence detector. One preferred label is, for example, alkaline phosphatase. Other labels known to one skilled in the art can also be employed as a means of detecting the bound double-stranded hybrid.

Detection of captured hybrid is preferably achieved by binding the conjugated antibody to the hybrid during an incubation step. Surfaces are then washed to remove any excess conjugate. These techniques are known in the art. For example, manual washes may be performed using either an Eppendorf™ Repeat Pipettor with a 50 ml Combitip™ (Eppendorf, Hamburg, Germany), a Corning repeat syringe (Corning, Corning, N.Y.), a simple pump regulated by a variostat, or by gravity flow from a reservoir with attached tubing. Commercially available tube washing systems available from Source Scientific Systems (Garden Grove, Calif.) can also be used.

Bound conjugate is subsequently detected by a method conventionally used in the art, for example, colorimetry or chemiluminescence as described at Coutlee, et al., J. Clin. Microbiol. 27:1002-1007 (1989). Preferably, bound alkaline phosphatase conjugate is detected by chemiluminescence by adding a substrate which can be activated by alkaline phosphatase. Chemiluminescent substrates that are activated by alkaline phosphatase are well known in the art.

In another embodiment, the target specific hybrid capture method of the invention employs blocker probes in addition to the CSP and SSP. A blocker probe comprises sequences that are complementary to the sequences of the CSP. The sequence of a blocker probe is preferably at least 75% complementary to the sequence of the CSP, more preferably, 100% complementary to the CSP. The addition of the blocker probes to the hybridization reaction mixture prevents non-hybridized CSP from hybridizing to cross-reactive nucleic acid sequences present in the target and therefore increases the specificity of the detection.

The blocker probe is generally at least 5 bases long, preferably 12 bases long. The concentration of the blocker probe in the hybridization reaction is preferably in excess to that of the CSP and SSP. Preferably, the blocker probe is present in a 2-fold molar excess, although, it may be present in an up to 10,000-fold molar excess. The blocker probes can be DNA, RNA, peptide nucleic acids (PNAs) or other nucleic acid analogues.

In one embodiment, blocker probes complementary to the full-length or near full-length of the CSP are used. Following the reaction in which the hybrid between CSP, SSP and the target nucleic acid is formed, one or more blocker probes may be added to the reaction and the hybridization is continued for a desired time. The hybridization products are then detected as described above.

In another embodiment, blocker probes complementary to only a portion of the CSP and are shorter than the CSP are used. These blocker probes have a lower melting temperature than that of the CSP. Preferably, the melting temperature of the blocker probe is 10 degrees lower than that of the CSP. In this case, the blocker probe is preferably added to the target nucleic acids simultaneously with the CSP and the SSP. Since the blocker probe has a lower melting temperature than the CSP, the initial temperature for hybridization is chosen such that the blocker probe does not interfere with the hybridization of the CSP to its target sequences. However, when the temperature of the hybridization mixtures is adjusted below the temperature used for target hybridization, the blocker probe hybridizes to the CSP and effectively blocks the CSP from hybridizing to cross-reactive nucleic acid sequences. For example, when the hybridization products are incubated at room temperature on a streptavidin-coated microtiter plate during hybrid capture, the blocker probes may be added.

The following examples illustrate use of the present amplification method and detection assay and kit. These examples are offered by way of illustration, and are not intended to limit the scope of the invention in any manner. All references described herein are expressly incorporated in toto by reference.

Example 1

Target-Specific Hybrid Capture (TSHC) Assay Protocol

Herpes Simplex Virus 1 (HSV-1) and Herpes Simplex Virus 2 (HSV-2) viral particles of known concentration (Advanced Biotechnologies, Inc., Columbia, Md.) or clinical samples were diluted using either Negative Control Media (Digene Corp., Gaithersburg, Md.) or Negative Cervical Specimens (Digene). Various dilutions were made and aliquoted into individual microfuge tubes. A half volume of the Denaturation Reagent 5100-0431(Digene) was added. Test samples were incubated at 65° C. for 45 minutes for denaturation of nucleic acids in the samples.

Following denaturation, a hybridization solution containing signal sequence probes (SSPs) (600 ng/ml each) and capture sequence probes (CSPs) (2.5 pmoles/ml each) was added to the sample, and incubated at 74° C. for 1 hour. Blocker probes in a solution containing one volume of 4× Probe Diluent (Digene), one volume of Denaturation Reagent and two volumes of the Negative Control Media were then added to the hybridization mixture and incubated at 74° C. for 15 minutes.

In a second series of experiments, following denaturation of nucleic acids, a hybridization mixture containing SSPs (600 ng/ml each), CSPs (2.5 pmoles/ml each), and blocker probes (250 pmoles/ml each) was added to the samples and incubated for one hour at 74° C.

Tubes containing reaction mixtures were cooled at room temperature for 5 minutes, and aliquots were taken from each tube and transferred to individual wells of a 96-well streptavidin capture plate (Digene). The plates were shaken at 1100 rpms for 1 hour at room temperature. The supernatants were then decanted and the plates were washed twice with SNM wash buffer (Digene) and inverted briefly to remove residual wash buffer. The alkaline-phosphatase anti-RNA/DNA antibody DR1 (Digene) was then added to each well and incubated 30 minutes at room temperature. The wells were then subjected to multiple wash steps which include: 1) three washes with Sharp wash buffer (Digene) at room temperature; 2) incubation of the plate with the Sharp wash buffer for 10 minutes at 60° C. on a heat block; 3) two washes with the Sharp wash buffer at room temperature; and 4) one wash with the SNM wash buffer (Digene) at room temperature. Following removal of the residual liquid, luminescent substrate 5100-0350 (Digene) was added to each well and incubated for 15 minutes at room temperature. The individual wells were then read on a plate luminometer to obtain the relative light unit (RLU) signal.

Solutions containing Negative Control Media or known HSV Negative Cervical Specimens were used as negative controls for the test samples. The signal to noise ratio (S/N) was calculated as the ratio of the average RLU obtained from a test sample to the average RLU of the negative control. The signal to noise ratio was used as the basis for determining capture efficiency and the detection of target nucleic acids. A S/N value of 2 or greater was arbitrarily assigned as a positive signal while a S/N values less than 2 was considered negative. The coefficient of variation (CV) which is a determination of the variability of the experiment within one sample set was calculated by taking the standard deviation of the replicates, dividing them by the average and multiplying that value by 100 to give a percent value.

The capture sequence probes and the blocker probes used in experiments described in Examples 2-13 were synthesized using the method described by Cook et al. (1988 Nucl. Acid. Res., 16: 4077-95). Unless otherwise noted, the capture sequence probes used in the experiments described herein were labeled with biotins at their 5' and 3' ends.

The signal sequence probes used in experiments described in Examples 2-13 are RNA probes. These probes were prepared using the method described by Yisraeli et al. (1989, Methods in Enzymol., 180: 42-50).

Example 2

The following tables describe the various probes used in experiments described in Examples 3-13.

TABLE 1

HSV-1 Clones from which HSV-1 Probes are derived

| Clone Name | Host Vector | Cloning Site(s) | Insert Size (bp) | Sequence Location within HSV-1 |
|---|---|---|---|---|
| RH3 | Dgx3 | Hind III, Eco RI | 5720 | 39850-45570 |
| R10 | Blue Script SK+ | Eco RI | 4072 | 64134-68206 |
| RH5B | Blue Script SK+ | Eco RV, Eco RI | 4987 | 105108-110095 |
| H19 | Blue Script SK+ | Hind III | 4890 | 133467-138349 |

TABLE 2

HSV-2 Clones from which HSV-2 Probes are derived

| Clone Name | Host Vector | Cloning Site(s) | Insert Size (bp) | Sequence Location in HSV-2 |
|---|---|---|---|---|
| E4A | Blue Script SK+ | Ham HI | 3683 | 23230-26914 |
| E4B | Blue Script SK+ | Bam HI Eco RI | 5600 | 26914-32267 |
| 18 | Blue Script SK+ | Hind III | 2844 | 41624-44474 |
| EI8 | Dgx3 | Hind III, Eco RI | 3715 | 44474-48189 |
| 4L | Blue Script KS+ | Bam HI, Eco RI | 4313 | 86199-90512 |

TABLE 3

Capture Sequence Probes for HSV-1

| Probe | Sequence | Size (bp) | Location within HSC-I |
|---|---|---|---|
| TS-1 | (TTATTATTA) COTTCATOTCGOCAAACAGCT CGT (TTATTATTA) [SEQ ID NO: 1] | 24 | 105040-105063 |
| TS-2 | (TTATTATTA) CGTCCTGGATGGCGATACGGC (TTATTATTA) [SEQ ID NO: 2] | 21 | 110316-110336 |
| VH-3 | CGTCCTGGATGGCGATACGGC [SEQ ID NO: 3] | 21 | 110316-110336 |
| NC-1 | CGTTCATGTCGGCAAACAGCTCGT [SEQ ID NO: 4] | 24 | 105040-105063 |

TABLE 3-continued

Capture Sequence Probes for HSV-1

| Probe | Sequence | Size (bp) | Location within HSC-I |
|---|---|---|---|
| VH-4 (fusion of VH3, NC-1) | CGTTCATGTCGGCAAACAGCTCGT-CGTCCTGGATGGCGATACGGC [SEQ ID NO: 5] | 45 | 105040-105063; 110316-110336 |
| HZ-1 | GATGGGGTTATTTTTCCTAAGATGGGGC GGGTCC [SEQ ID NO: 6] | 34 | 133061-133094 |
| VH-2 | TACCCCGATCATCAGTTATCCTTAAGGT [SEQ ID NO: 7] | 28 | 138367-138394 |
| FD-1 | AAACCGTTCCATGACCGGA [SEQ ID NO: 8] | 19 | 39281-39299 |
| RA-2 | ATCGCGTGTTCCAGAGACAGGC [SEQ ID NO: 9] | 22 | 39156-39177 |
| NC-2 | CAACGCCCAAAATAATA [SEQ ID NO: 10] | 17 | 46337-46353 |
| FD-2 | GTCCCCGAaCCGATCTAGCG (note small cap a is mutated base) [SEQ ID NO: 11] | 20 | 45483-45502 |
| RA-4 | CGAACCATAAACCATTCCCCAT [SEQ ID NO: 12] | 22 | 46361-46382 |
| ON-3 | CACGCCCGTGGTTCTGGAATTCGAC [SEQ ID NO: 13] | 25 | 64105-64129 |
| HZ-2 | (TTTATTA)GATGGGGTTATTTTTCCTAAGAT GGGGCGGGTCC [SEQ ID NO: 14] | 34 | i3:',061-133094 |
| ZD-1 | GGTTATTTTTCCTAAG [SEQ ID NO: 15] | 16 | 133064-133079 |
| ZD-2 | (ATTATT)GGTTATTTTTCCTAAG(ATTATT) [SEQ ID NO: 16] | 16 | 133064-133079 |
| F6R | ACGACGCCCTTGACTCCGATTCGTCATCGGAT GACTCCCT [SEQ ID NO: 17] | 40 | 87111-87150 |
| BRH19 | ATGCGCCAGTGTATCAATCAGCTGTTTCGGGT [SEQ ID NO: 18] | 32 | 133223-133254 |
| F1 5R | CAAAACGTCCTGGAGACGGGTGAGTGTCGGC GAGGACG [SEQ ID NO: 19] | 38 | 141311-141348 |
| VH-1 | GTCCCCGACCCGATCTAGCG [SEQ ID NO: 20] | 20 | 45483-45502 |
| ON-4 | GCAGACTGCGCCAGGAACGAGTA [SEQ ID NO: 21] | 23 | 68404-68426 |
| PZ-1 | GTGCCCACGCCCGTGGTTCTGGAATTCGACAG CGA [SEQ ID NO: 22] | 35 | 64105-64139 |
| PZ-2 | GCAGACTGCGCCAGGAACGAGTAGTTGGAGT ACTG [SEQ ID NO: 23] | 35 | 68404-68438 |
| FG-2 | AAGAGGTCCATTGGGTGGGGTTGATACGGGA AAGAC [SEQ ID NO: 24] | 36 | 105069-105104 |
| FG-3 | CGTAATGCGGCGGTGCAGACTCCCCTG [SEQ ID NO: 25] | 27 | 110620-110646 |

TABLE 3-continued

Capture Sequence Probes for HSV-1

| Probe | Sequence | Size (bp) | Location within HSC-I |
|---|---|---|---|
| FG-4 | CCAACTACCCCGATCATCAGTTATCCTT AAGGTCTCTTG [SEQ ID NO: 6] | 39 | 138362-138400 |
| Hsv 1-LF15R (SH-3) | (AAAAAAAAA)CAAAACGTCCTGGAGACGGGT GAGTGTCGGCGAGGACG [SEQ ID NO: 27] | 38 | 141311-141348 |
| Hsv 1-F15-2B (GZ-1) | CAAAACGTCCTGGAGACGGGTGAGTGTCGGC GAGGACG [SEQ ID NO: 28] | 38 | 141311-141348 |
| Hsv 1-F15-3B (GZ-2) | CAAAACGTCC-bio-U-GGAGACGGGTGAG TG-bio-U-CGGCGAGGACG [SEQ ID NO: 29] | 38 | 141311-141348 |

*Sequences in parentheses are "tail" sequences not directed at HSV.

TABLE 4

Blocker Probes for HSV-1

| Probe | Sequence | Size (bp) | Capture Probe to Which it hybridizes |
|---|---|---|---|
| EA-1 | AOGAAAAATAACCCCATC [SEQ ID NO: 30] | 18 | HZ-1 |
| EA-2 | GACCCGCCCCATCTT [SEQ ID NO: 31] | 15 | HZ-1 |
| ZD-3 | GGACCCGCCCCATCTTAG GAAAAATAACCCCATC [SEQ ID NO: 32] | 34 | HZ-1 |
| NG-7 | AAAAATAACCCCA [SEQ ID NO: 33] | 13 | HZ-1 |
| NG-8 | CGCCCCATCTT [SEQ ID NO: 34] | 11 | HZ-1 |
| NG-4 | CCATCTTAGGAAAAA [SEQ ID NO: 35] | 15 | HZ-1 |
| GP-1 | ATAACTGATGATCGG [SEQ ID NO: 36] | 15 | VH-Z |
| EA-3 | CCACCCAATGGACCTC [SEQ ID NO: 37] | 16 | FG-2 |
| EA-4 | GTCTTTCCCGTATCAACC [SEQ ID NO: 38] | 18 | FG-2 |
| EB-7 | CGCCGCATTACG [SEQ ID NO: 39] | 12 | FG-3 |
| EB-8 | AGGGGAGTCTGC [SEQ ID NO: 40] | 12 | FG-3 |
| GP-3 | CTGTTTGCCGACA [SEQ ID NO: 41] | 13 | VH-4 |
| GP-4 | TATCGCCATCCAG [SEQ ID NO: 42] | 13 | VH-4 |
| EB-9 | ATGATCGGGGTAGT [SEQ ID NO: 43] | 14 | FG-4 |
| EB-10 | AGAGACCTTAAGGATA [SEQ ID NO: 44] | 16 | FG-4 |
| NG-1 | ATTCCAGAACCACGG [SEQ ID NO: 45] | 15 | ON-3 |
| NG-2 | TTCCAGAACCACG [SEQ ID NO: 46] | 13 | ON-3 |
| NG-3 | TCCAGAACCAC [SEQ ID NO: 47] | 11 | ON-4 |
| GP-5 | GTTCCTGGCGCAG [SEQ ID NO: 48] | 13 | ON-4 |
| GP-6 | TTCCTGGCGCAG [SEQ ID NO: 49] | 12 | ON-4 |

TABLE 5

Capture Sequence Probes for HSV-2

| Probe | Sequence | Size (bp) | Location within HSV-2 |
|---|---|---|---|
| N14-1 | OCCCOCCOCCOCCAOCACTACTTTC [SEQ ID NO: 50] | 24 | 41610-41587 |
| FG-1 | AAACGTTGGGAGGTGTGTGCGTCA TCCTGGAGCTA [SEQ ID NO: 51] | 35 | 48200-48234 |
| LE-3 | GACCAAAACCGAGTGAGGTTCTGTGT [SEQ ID NO: 52] | 26 | 48732-48757 |
| NF-2 | AAACGTTGGGAGGTGTGTGCGTCA [SEQ ID NO: 53] | 24 | 48200-48223 |
| RA-3 | TGCTCGTCACGAAGTCACTCATG [SEQ ID NO: 54] | 23 | 22756-22734 |
| ON-2 | CATTACTGCCCGCACCGGACC [SEQ ID NO: 55] | 21 | 23862-23842 |
| LE-1 | GCCGTGGTGTTCCTGAACACCAGG [SEQ ID NO: 56] | 24 | 27666-27643 |
| LE-4 | AGTCAGGGTTGCCCGACTTCGTCAC [SEQ ID NO: 57] | 25 | 22891-22867 |

TABLE 5-continued

Capture Sequence Probes for HSV-2

| Probe | Sequence | Size (bp) | Location within HSV-2 |
|---|---|---|---|
| NF-3 | CAGGCGTCCTCGGTCTCGGGCGGGGC [SEQ ID NO: 58] | 26 | 32847-32822 |
| NF-4 | CCCACGTCACCGGGGGCCCC [SEQ ID NO: 59] | 20 | 26743-26724 |
| LE-2 | GCCGGTCGCGTGCGACGCCCAAGGC [SEQ ID NO: 60] | 25 | 33130-33106 |
| SG-3 | CCGACGCGTGGGTATCTAGGGGGTCG [SEQ ID NO: 61] | 26 | 90559-90534 |
| SG-4 | CGGGACGGCGAGCGGAAAGTCAACGT [SEQ ID NO: 62] | 26 | 86194-86169 |

TABLE 6

Blocker Probes for HSV-2

| Probe Name | Sequence | Size (bp) | Capture Probe to which it hybridizes |
|---|---|---|---|
| HX-4 | GGCGCOGOC [SEQ ID NO: 63] | 9 | NF-1 |
| HX-5 | GAAAGTAGTGCTGGC [SEQ ID NO: 64] | 15 | NF-1 |
| GP-7 | TGCTGGCGGCG [SEQ ID NO: 65] | 11 | NF-1 |
| AZ-3 | ACACCTCCCAACG [SEQ ID NO: 66] | 13 | FG-1 |
| AZ-4 | CTCCAGGATGACG [SEQ ID NO: 67] | 13 | FG-1 |
| GR-1 | TCGGTTTTGGTC [SEQ ID NO: 68] | 12 | LE-3 |
| GR-2 | ACACAGAACCTCA [SEQ ID NO: 69] | 13 | LE-3 |
| GP-8 | CACACACCTCCCA [SEQ ID NO: 70] | 13 | NF-2 |
| BR-10 | CGACCCCCTAGATA [SEQ ID NO: 71] | 14 | SG-3 |
| BR-11 | CCACGCGTCGG [SEQ ID NO: 72] | 11 | SG-3 |
| HX-6 | ACGTTGACTTTCCGC [SEQ ID NO: 73] | 15 | SG-4 |
| BR-15 | CGCCGTCCCG [SEQ ID NO: 74] | 10 | SG-4 |

TABLE 7

Capture Sequence Probes for HPV

| Probe | Sequence | Size (bp) | HPV Type and Sequence Location |
|---|---|---|---|
| ZL-1 | GTACAGATGGTACCGGGGTTGTAGAAGTATCTG [SEQ ID NO: 75] | 33 | HPV16 5360-5392 |
| ZL-4 | CTGCAACAAGACATACATCGACCGGTCCACC [SEQ ID NO: 76] | 31 | HPV16 495-525 |
| DP-1 | GAAGTAGGTGAGGCTGCATGTGAAGTGGTAG [SEQ ID NO: 77] | 31 | HPV16 5285-5315 |
| DP-4 | CAGCTCTGTGCATAACTGTGGTAACTTTCTGGG [SEQ ID NO: 78] | 33 | HPV16 128-160 |
| SH-1 | GAGGTCTTCTCCAACATGCTATGCAACGTCCTG [SEQ ID NO: 79] | 33 | HPV31 505-537 |
| SH-4 | GTGTAGGTGCATGCTCTATAGGTACATCAGGCC [SEQ ID NO: 80] | 33 | HPV31 5387-5419 |
| VS-1 | CAATGCCGAGCTTAGTTCATGCAATTTCCGAGG [SEQ ID NO: 81] | 33 | HPV31 132-164 |
| VS-4 | GAAGTAGTAGTTGCAGACGCCCCTAAAGGTTGC [SEQ ID NO: 82] | 33 | HPV31 5175-5207 |
| AH-1 | GAACGCGATGGTACAGGCACTGCAGGGTCC [SEQ ID NO: 83] | 30 | HPV18 5308-5337 |
| AH-2 | GAACGCGATGGTACAGGCACTGCA [SEQ ID NO: 84] | 24 | HPV18 5314-5337 |
| AL-1 | ACGCCCACCCAATGGAATGTACCC [SEQ ID NO: 85] | 24 | HPV18 4451-4474 |

TABLE 7-continued

Capture Sequence Probes for HPV

| Probe | Sequence | Size (bp) | HPV Type and Sequence Location |
|---|---|---|---|
| PA-4 | TCTGCGTCGTTGGAGTCGTTCCTGTCGTGCTC [SEQ ID NO: 86] | 32 | HPV18 535-566 |
| 18-1AB | (TTATTATTA)CTACATACATTGCCGCCATGTTCGCCA [SEQ ID NO: 87] | 36 | HPV18 1369-1395 |
| 18-2AB | (TTATTATTA)TGTTGCCCTCTGTGCCCCCGTTGTCTATAGCCTCCGT [SEQ ID NO: 88] | 46 | HPV18 1406-1442 |
| 18-3AB | (TTATTATTA)GGAGCAGTGCCCAAAAGATTAAAGTTTGC [SEQ ID NO: 89] | 38 | HPV18 7524-7552 |
| 18-4AB | (TTATTATTA)CACGGTGCTGGAATACGGTGAGGGGGTG [SEQ ID NO: 90] | 37 | HPV18 3485-3512 |
| 18-5AB | (TTATTATTA)ACGCCCACCCAATGGAATGTACCC [SEQ ID NO: 91] | 33 | HPV18 4451-4474 |
| 18-6AB | (TTATTATTA)ATAGTATTGTGGTGTGTTTCTCACAT [SEQ ID NO: 92] | 35 | HPV18 81-106 |
| 18-7AB | (TTATTATTA)GTTGGAGTCGTTCCTGTCGTG [SEQ ID NO: 93] | 30 | HPV18 538-558 |
| 18-8AB | (TTATTATTA)CGGAATTTCATTTTGGGGCTCT [SEQ ID NO: 94] | 31 | HPV18 634-655 |
| PE-1 | GCTCGAAGGTCGTCTGCTGAGCTTTCTACTACT [SEQ ID NO: 95] | 33 | HIPV18 811-843 |
| PZ-2 | GCGCCATCCTGTAATGCACTTTTCCACAAAGC [SEQ ID NO: 96] | 32 | HPV45 77-108 |
| PZ-5 | TAGTGCTAGGTGTAGTGGACGCAGGAGGTGG [SEQ ID NO: 97] | 31 | HPV45 5295-5325 |
| CS-1 | GGTCACAACATGTATTACACTGCCCTCGGTAC [SEQ ID NO: 98] | 32 | HPV45 500-531 |
| CS-4 | CCTACGTCTGCGAAGTCTTTCTTGCCGTGCC [SEQ ID NO: 99] | 31 | HPV45 533-563 |
| PF-1 | CTGCATTGTCACTACTATCCCCACCACTACTTTG [SEQ ID NO: 100] | 34 | HPV45 1406-1439 |
| PF-4 | CCACAAGGCACATTCATACATACACGCACGCA [SEQ ID NO: 101] | 32 | HPV45 7243-7274 |
| PA-1 | GTTCTAAGGTCCTCTGCCGAGCTCTCTACTGTA [SEQ ID NO: 102] | 33 | HPV45 811-843 |
| 45-5AB | (TTATTATTA)TGCGGTTTTGGGGGTCGACGTGGAGGC [SEQ ID NO: 103] | 36 | HPV45 3444-3470 |
| 45-6AB | (TTATTATTA)AGACCTGCCCCCTAAGGGTACATAGCC [SEQ ID NO: 104] | 36 | HPV45 4443-4469 |
| 45-8AB | (TTATTATTA)CAGCATTGCAGCCTTTTTGTTACTTGCTTGTAATAGCTCC [SEQ ID NO: 105] | 49 | HPV45 1477-1516 |
| 45-9AB | (TTATTATTA)ATCCTGTAATGCACTTTTCCACAAA [SEQ ID NO: 106] | 34 | HPV45 79-103 |
| 45-10AB | (TTATTATTA)GCCTGGTCACAACATGTATTAC [SEQ ID NO: 107] | 31 | HPV45 514-535 |

TABLE 7-continued

Capture Sequence Probes for HPV

| Probe | Sequence | Size (bp) | HPV Type and Sequence Location |
|---|---|---|---|
| 45-11AB | (TTATTATTA)CAGGATCTAATTCATTCTGAGGTT [SEQ ID NO: 108] | 33 | HPV45 633-656 |
| ON-1 | TGCGGTTTTGGGGGTCGACGTGGAGGC [SEQ ID NO: 109] | 27 | HPV45 3444-3470 |

*Sequences in parentheses are "tail" sequences not directed at HSV.

TABLE 8

Blocker Probes For HPV

| Probe | Sequence | Size (bp) | Capture Probe to which it hybridizes |
|---|---|---|---|
| PV-FD-1 | GCCTCCACGTCGAC [SEQ ID NO: 110] | 14 | ON-1/45-5AB |
| PV-FD-2 | CCCCAAAACCG [SEQ ID NO: 111] | 11 | ON-1/45-5AB |
| PV-FD-3 | GGTACATTCCATTGGG [SEQ ID NO: 112] | 16 | 18-5AB/AL-1 |
| PV-FD-4 | TGGGCGTTAATAATAA [SEQ ID NO: 113] | 16 | 18-5AB |
| AH-3 | ACCATCGCGTTC [SEQ ID NO: 114] | 12 | AH-2 |
| AH-4 | GGACCCTGCAGTGC [SEQ ID NO: 115] | 14 | AH-1 |
| AH-5 | CTGTACCATCGCGTT 3' [SEQ ID NO: 116] | 15 | AH-1 |
| AH-6 | TGCAGTGCCTGT [SEQ ID NO: 117] | 12 | AH-2 |
| PZ-1 | CCACCTCCTGCGT [SEQ ID NO: 118] | 13 | PZ-5 |
| PZ-3 | ATTACAGGATGGCGC [SEQ ID NO: 119] | 15 | PZ-2 |
| PZ-4 | GCTTTGTGGAAAAGTG [SEQ ID NO: 120] | 16 | PZ-2 |
| PZ-6 | CCACTACACCTAGCACTA [SEQ ID NO: 121] | 18 | PZ-5 |
| ZL-2 | CAGATACTTCTACAACC [SEQ ID NO: 122] | 17 | ZL-1 |
| ZL-3 | CCGGTACCATCTGTAC [SEQ ID NO: 123] | 16 | ZL-1 |
| ZL-5 | GGTGGACCGGTCG [SEQ ID NO: 124] | 13 | ZL-4 |
| ZL-6 | ATGTATGTCTTGTTGCAG [SEQ ID NO: 125] | 18 | ZL-4 |
| DP-2 | CTACCACTTCACATGC [SEQ ID NO: 126] | 16 | DP-1 |
| DP-3 | AGCCTCACCTACTTC [SEQ ID NO: 127] | 15 | DP-1 |
| DP-5 | CCCAGAAAGTTACCAC [SEQ ID NO: 128] | 16 | DP-4 |
| DP-6 | AGTTATGCACAGAGCT [SEQ ID NO: 129] | 16 | DP-4 |
| SH-2 | CAGGACGTTGCATAGC [SEQ ID NO: 130] | 16 | SH-1 |
| SH-3 | ATGTTGGAGAAGACCTC [SEQ ID NO: 131] | 17 | SH-1 |
| SH-5 | GGCCTGATGTACCTATA [SEQ ID NO: 132] | 17 | SH-4 |
| SH-6 | GAGCATGCACCTACAC [SEQ ID NO: 133] | 16 | SH-4 |
| VS-2 | CTCGGAAATTGCATG [SEQ ID NO: 134] | 15 | VS-1 |
| VS-3 | AACTAAGCTCGGCATT [SEQ ID NO: 135] | 16 | VS-1 |
| VS-5 | GCAACCTTTAGGGG [SEQ ID NO: 136] | 14 | VS-4 |
| VS-6 | CGTCTGCAACTACTACTTC [SEQ ID NO: 137] | 19 | VS-4 |
| CS-2 | GTACCGAGGGCAGT [SEQ ID NO: 138] | 14 | CS-1 |
| CS-3 | GTAATACATGTTGTGACC [SEQ ID NO: 139] | 18 | CS-1 |
| CS-5 | GGCACGGCAAGAAA [SEQ ID NO: 140] | 14 | CS-4 |
| CS-6 | GACTTCGCAGACGTAGG [SEQ ID NO: 141] | 17 | CS-4 |
| PF-2 | CAAAGTAGTGGTGGG [SEQ ID NO: 142] | 15 | PF-1 |
| PF-3 | GATAGTAGTGACAATGCAG [SEQ ID NO: 143] | 19 | PF-1 |
| PF-5 | TGCGTGCGTGTATGTA [SEQ ID NO: 144] | 16 | PF-4 |
| PF-6 | TGAATGTGCCTTGTGG [SEQ ID NO: 145] | 16 | PF-4 |
| PE-2 | AGTAGTAGAAAGCTCAGC [SEQ ID NO: 146] | 18 | PE-1 |
| PE-3 | AGACGACCTTCGAGC [SEQ ID NO: 147] | 15 | PE-1 |

TABLE 8-continued

Blocker Probes For HPV

| Probe | Sequence | Size (bp) | Capture Probe to which it hybridizes |
|---|---|---|---|
| PA-2 | TACAGTAGAGAGCTCGG [SEQ ID NO: 148] | 17 | PA-1 |
| PA-3 | CAGAGGACCTTAGAAC [SEQ ID NO: 149] | 16 | PA-1 |
| PA-5 | GAGCACGACAGGAACG [SEQ ID NO: 150] | 16 | PA-4 |
| PA-6 | ACTCCAACGACGCAGA [SEQ ID NO: 151] | 16 | PA-4 |

Example 3

Effect of the Extent of Biotin Labeling on Capture Efficiency

Tests were conducted to determine the optimal number of biotin labels per capture sequence probe for TSHC detection. The general TSHC method described in Example 1 was employed. The capture efficiency of capture sequence probe F15R labelled with one, two, or three biotins, measured by signal to noise ratio (S/N), were tested. The signal sequence probe employed was H19. As shown in Table 9, two biotins per capture sequence probe were sufficient for optimal capture efficiency. Greater than a 50% increase in S/N was observed using capture sequence probe with two biotin labels compared to the single biotin labeled capture sequence probe. The addition of a third biotin label to the capture sequence probe resulted in a decrease in S/N relative to the two-biotin labeled capture sequence probe.

TABLE 9

Effect of the Extent of Biotin Labeling on Capture Efficiency

| # Biotins | HSV-1/well | RLU | CV | S/N |
|---|---|---|---|---|
| One | 0 | 54 | 3% | 1.0 |
| One | $4.5 \times 10^3$ | 236 | 2% | 4.4 |
| One | $4.5 \times 10^4$ | 1861 | 3% | 34.5 |
| One | $4.5 \times 10^5$ | 15633 | 7% | 289.5 |
| Two | 0 | 46 | 3% | 1.0 |
| Two | $4.5 \times 10^3$ | 296 | 10% | 6.4 |
| Two | $4.5 \times 10^4$ | 2558 | 1% | 55.6 |
| Two | $4.5 \times 10^5$ | 23369 | 4% | 508.0 |
| Three | 0 | 44 | 22% | 1.0 |
| Three | $4.5 \times 10^3$ | 243 | 6% | 5.5 |
| Three | $4.5 \times 10^4$ | 1820 | 2% | 51.4 |
| Three | $4.5 \times 10^5$ | 18581 | 8% | 422.3 |

Example 4

Effect of the Distance between the CSP and the SSP Target Sites on Capture Efficiency The effect of the distance between capture sequence probe (CSP) and signal sequence probe (SSP) hybridization sites on a HSV-1 target nucleic acid on capture efficiency was evaluated. CSPs that hybridize to HSV-1 nucleic acid sequences which are located 0.2 kb, 3 kb, 18 kb, 36 kb and 46 kb from the site of SSP hybridization were tested. The general TSHC method described in Example 1 was employed. The capture efficiencies were 100%, 50%, 30%, 19% and 7%, respectively (Table 10). A steady decline in relative capture efficiencies was observed as the distance increased from 0.2 Kb to 46 Kb.

TABLE 10

Effect of Distance between Target Sites on Capture Efficiency

| CSP | SSP | Distance Between Target Site | Relative Capture Efficiency |
|---|---|---|---|
| BRH19 | H19 | 0.2 Kb | 100% |
| F15R | H19 | 3 Kb | 50% |
| F6R | RH5B | 18 Kb | 30% |
| F15R | RH5B | 36 Kb | 19% |
| F6R | H19 | 46 Kb | 7% |

Example 5

Effect of Fused Capture Sequence Probe on TSHC Detection of HSV-1

The binding capacity of streptavidin plates was determined to be approximately 2 pmoles of doubly-biotinylated CSPs per well. Since the CSPs are doubly biotin-labeled, a maximum of 8 CSPs (2 CSPs per SSP) is preferred in order not to exceed the binding capacity of the wells. Any increase in biotin-labeled capture sequence probe above the stated capacity resulted in a decrease in signal, the so-called "hook effect." In order to avoid this "hook effect" and still permit the use of greater than four SSP-CSP combinations, the effect of synthesizing oligonucleotides that contained the sequences of two CSPs fused together (5' and 3' sites) was tested. The fused capture sequence probes may function independently to drive hybridization to the unique target sites. In another embodiment, the fused probes may bind to two target sites with the second hybridization favored, since it is essentially a unimolecular reaction with zero order kinetics once the probe has hybridized to the first site. The hybridization may be determined by one or both mechanisms. Previous experiments showed that two CSPs, VH3 and NC-1, when used together, gave approximately twice the S/N as the individual CSPs. Unfused capture sequence probes VH-3 and NC-1 were used at 2.5 pmoles/ml each for a total concentration of 5 pmoles/ml, fused probe VH-4 (fusion of VH-3 and NC-1) was used at 2.5 pmole/ml. As shown in Table 11, the fused probe was as effective as the combination of the two unfused probes. Therefore, TSHC detection using fused capture sequence probes permits the number of nucleic acid sequences targeted by the signal sequence probe to be at least doubled without exceeding the plate biotin-binding capacity. The experiment also demonstrates the lack of cross-reactivity of HSV-2 at $10^7$ genomes as shown by the S/N less than 2.0.

TABLE 11

Comparison of Fused v. Unfused Capture Sequence Probes in TSHC Detection of HSV-1

| SSP | CSP | Viral Particles/ml | RLU | CV | S/N |
|---|---|---|---|---|---|
| RH5B | VH-3, NC-1 | 0 | 94 | 14% | 1.0 |
| RH5B | VH-3, NC-1 | $10^4$ HSV-1 | 164 | 5% | 1.7 |
| RH5B | VH-3, NC-1 | $10^5$ HSV-1 | 1003 | 4% | 10.7 |
| RH5B | VH-3, NC-1 | $10^7$ HSV-2 | 125 | 6% | 1.3 |
| RH5B | VH-4 (fused) | 0 | 97 | 10% | 1.0 |

TABLE 11-continued

Comparison of Fused v. Unfused Capture Sequence Probes in TSHC Detection of HSV-1

| SSP | CSP | Viral Particles/ml | RLU | CV | S/N |
|---|---|---|---|---|---|
| RHSB | VH-4 (fused) | 10^4 HSV-1 | 181 | 3% | 1.9 |
| RHSB | VH-4 (fused) | 10^5 HSV-1 | 1070 | 2% | 11.0 |
| RHSB | VH-4 (fused) | 10^7 HSV-2 | 140 | 5% | 1.4 |

Example 6

Capture Efficiency of Various CSPs and SSPs in TSHC Detection of HSV-1

The capture efficiency of capture sequence probes (CSPs) for each of the four HSV-1 specific signal sequence probes (SSPs), H19, RH5B, RH3 and R10, in the detection of HSV-1 by TSHC were evaluated. The criteria used for designing the capture sequence probes were: 1) the CSP hybridization site is within 1 kb either 5' or 3' of the SSP hybridization site on the HSV-1 nucleic acid sequence, preferably within 0.5 kb; and 2) the CSPs contain sequences that are unique to HSV-1, with no stretches of sequence homology to HSV-2 greater than 10 bases. The CSPs were designed to target the 5' and 3' regions adjacent to the SSP hybridization site, preferably with a 5' CSP and a 3' CSP for each SSP. The Omiga software (Oxford Molecular Group, Campbell, Calif.) was instrumental in the identification of such sites. The melting temperature (Tm) of the CSPs was designed to be between 70° C. to 85° C., to conform to the 70° C. to 75° C. hybridization temperature used in Hybrid Capture II (HCII) assay for HSV (Digene). The general TSHC method described in Example 1 was employed. Eleven CSPs (which bind to 6 different sites) for H19, six CSPs (which bind to three unique sites) for RH5B, six CSPs (which bind to six unique sites) for RH3, and two CSPs for R10 were tested. As shown in Table 12, efficient capture sequence probes were found for signal sequence probes H19, RH5B and R10.

TABLE 12

CSPs and SSPs for TSHC Detection of HSV-1

| SSP | CSP | Cap % | SSP | CSP | Cap % | SSP | CSP | Cap % |
|---|---|---|---|---|---|---|---|---|
| R10 | ON-3 | 100% | RH5B | TS-1 | 50% | H19 | HZ-1 | 50% |
| R10 | ON-3 | 80% | RH5B | NC-1 | 75% | H19 | HZ-2 | 20% |
| | | | RH5B | VH-4 | 130% | H19 | ZD-1 | 40% |
| | | | RH5B | TS-2 | 25% | H19 | ZD-2 | 20% |
| | | | RH5B | VH-3 | 50% | H19 | BRH19 | 70% |
| | | | | | | H19 | VH-2 | 70% |
| | | | | | | H19 | Fl 5R | 25% |

Example 7

Capture Efficiency of Various CSPs and SSPs in TSHC Detection of HSV-2

The capture efficiency of capture sequence probes (CSPs) for each of the four HSV-2 specific signal sequence probes (SSPs), E4A, E4B, Ei8, and i8, in the detection of HSV-2 by TSHC were evaluated. HSV-2 specific capture sequence probes (CSPs) were designed based on the same criteria as the HSV-1 CSPs except for the requirement that they be HSV-2 specific. Four CSPs for E4A, three CSPs for E4B, and two CSPs each for Ei8 and i8 were tested. The general TSHC method described in Example 1 was employed. As shown in Table 13, efficient capture sequence probes were found for i8 and Ei8.

TABLE 13

CSPs and SSPs for TSHC Detection of HSV-2

| SSP | CSP | Cap % | SSP[†] | CSP | Cap % |
|---|---|---|---|---|---|
| 18 | NF-1 | 100% | Ei8 | NF-2 | 50% |
| | | | Ei8 | LE-3 | 45% |

Example 8

Effect of Blocker Probes on HSV-1 and HSV-2 Detection

In an attempt to reduce cross-reactivity of TSHC while allowing the capture step to take place at room temperature, methods using blocker probes were developed. Blocker probes comprise sequences that are complementary to the capture sequence probes (CSPs) used for detection. These experiments were designed to prevent non-specific hybridization of the CSPs to non-targeted nucleic acids present in the sample under the lower stringency conditions, a situation often encountered during the room temperature capture step.

In one method, blocker probes that are complementary to the full length or nearly the full length of the capture sequences probe were used. The blocker probes were added to the reaction mixture in 10-fold excess relative to the CSP after hybridization of the CSP and the SSP to the target DNA molecule has occurred. Since the blocker probes have similar melting temperature as the CSPs, the CSPs were hybridized to the target nucleic acids first to prevent hybridization of the blocker probes to the CSPs before the hybridization of the CSPs to the target nucleic acids occurred. As shown in Table 14, the addition of the blocker probes resulted in a dramatic reduction in cross-reactivity while these probes had no effect on the sensitivity of HSV-1 detection. The S/N for the detection of cross-reactive HSV-2 ($10^7$ viral particles/ml) decreased from 5.0 to 0.8 when the blocker probes were used.

In another method, blocker probes that are complementary to only a portion of the CSPs and are shorter than the CSPs were used. The blocker probes were designed to have melting temperatures above room temperature but at least 10° C. below the hybridization temperature of CSPs to the target nucleic acids. Since these blocker probes hybridize to the CSPs at temperature below the CSP hybridization temperature to the target nucleic acids, the blocker probes may be added to the reaction at the same time as the CSP and SSP without effecting the hybridization efficiency of the CSPs to the target nucleic acid. These shorter blocker probes function during the room temperature capture step by hybridizing to the CSPs at the lower temperatures that are encountered during the room temperature capture step. As shown in Table 15, the addition of either single or paired shorter blocker probes in 100-fold excess relative to the CSPs resulted in a dramatic reduction in cross-reactivity but had no effect on sensitivity of HSV-1 detection. The S/N for detecting crossreactive HSV-2 ($10^7$ viral particles/ml) without the blocker probes was 10.6, but was reduced to less than or equal to 1.5 with the addition of the blocker probes.

Therefore, both methods utilizing blocker probes provide a substantial reduction in cross-reactivity. The second method utilizing blocker probes with lower melting temperature may be preferred because the addition of blocker probes at the same time as the capture sequence probe eliminates the need for an extra step for the detection method.

TABLE 14

Effect of Blocker Probes Added Post Capture probe hybridization on TSHC

| SSP | CSP | 100x Blocker Probe | Viral Particles/ml | RlX | CV | S/N |
|---|---|---|---|---|---|---|
| H19 | HZ-1 | None | 0 | 66 | 7% | 1.0 |
| H19 | HZ-1 | None | $10^5$ HSV-1 | 246 | 5% | 3.7 |
| H19 | HZ-1 | None | $10^6$ HSV-1 | 1998 | 2% | 30.3 |
| H19 | HZ-1 | None | $10^7$ HSV-2 | 327 | 2% | 5.0 |
| H19 | HZ-1 | ZD-3 | 0 | 60 | 3% | 1.0 |
| H19 | HZ-1 | ZD-3 | $10^5$ HSV-1 | 267 | 4% | 4.5 |
| H19 | HZ-1 | ZD-3 | $10^6$ HSV-1 | 2316 | 6% | 38.6 |
| H19 | HZ-1 | ZD-3 | $10^7$ HSV-2 | 49 | 2% | 0.8 |

TABLE 15

Effect of Blocker Probes Added Simultaneously with the Capture Probes on TSHC Detection of HSV-1

| SSP | CSP | 10x Blocker Probe | Viral Particle/all | RLU | CV | S/N |
|---|---|---|---|---|---|---|
| H19 | HZ-1 | none | 0 | 38 | 15% | 1.0 |
| H19 | HZ-1 | none | $10^4$ HSV-1 | 71 | 2% | 1.9 |
| H19 | HZ-1 | none | $10^5$ HSV-1 | 389 | 12% | 10.2 |
| H19 | HZ-1 | none | $10^7$ HSV-2 | 401 | 18% | 10.6 |
| H19 | HZ-1 | NG-4 | 0 | 39 | 8% | 1.0 |
| H19 | HZ-1 | NG-4 | $10^4$ HSV-1 | 82 | 5% | 2.1 |
| H19 | HZ-1 | NG-4 | $10^5$ HSV-1 | 411 | 18% | 10.5 |
| H19 | HZ-1 | NG-4 | $10^7$ HSV-2 | 57 | 15% | 1.5 |
| H19 | HZ-1 | EA-1, EA-2 | 0 | 37 | 0% | 1.0 |
| H19 | HZ-1 | EA-1, EA-2 | $10^4$ HSV-1 | 75 | 8% | 2.0 |
| H19 | HZ-1 | EA-1, EA-2 | $10^5$ HSV-1 | 419 | 8% | 11.3 |
| H19 | HZ-1 | EA-1, EA-2 | $10^7$ HSV-2 | 49 | 5% | 1.3 |
| H19 | HZ-1 | NG-7, NG-8 | 0 | 42 | 10% | 1.0 |
| H19 | HZ-1 | NG-7, NG-8 | $10^4$ HSV-1 | 76 | 3% | 1.8 |
| H19 | HZ-1 | NG-7, NG-8 | $10^5$ HSV-1 | 471 | 5% | 11.2 |
| H19 | HZ-1 | NG-7, NG-8 | $10^7$ HSV-2 | 47 | 9% | 1.1 |

Example 9

TSHC Detection Reduces Vector Background

The TSHC assay eliminates the vector contamination problem often associated with the Hybrid Capture II (HC II) detection assay (Digene). As the RNA signal sequence probes used in HC II are generated from linearized vector templates, any remaining unlinearized plasmid DNA results in the production of additional RNA probe sequences specific for vector sequences. In the HC II assay, the RNA/DNA hybrids that form as a result of these read-through transcripts are captured on the antibody coated plates and generate signal. In contrast, in the TSHC method, only those RNA/DNA hybrids that also hybridize to the capture sequence probes are detected. Accordingly, any detection of vector-related sequences is eliminated. Plasmids SK+, pBR322, DgZ and 1066 which were known to be detectable in HSV HC II test (Digene) were tested in the TSHC assay using two RNA signal sequence probes (H19 and RH5b) and two capture sequence probes (VH-2 and VH-4). Identical set of RNA probes were then used in HC II method and the TSHC method for the detection of HSV-1. The general TSHC method described in Example 1 was employed. As shown in Table 16, while signal to noise ratio in standard HC II ranged from 14 to 48, the signal to noise ratio for the TSHC method was less than 2 for all plasmids tested.

TABLE 16

Vector Background in TSHC v. HCII Detection

| Method | SSP | CSP | Targets/ml | RLU | CV | S/N |
|---|---|---|---|---|---|---|
| TSHC | H19 + RHSB | VH-2 + VH-4 | 0 | 94 | 6% | 1.0 |
| TSHC | H19 + RH5B | VH-2 + VH-4 | 4 ng pBS SK+ | 137 | 7% | 1.5 |
| TSHC | H19 + RH5B | VH-2 + VH-4 | 2 ng pBR322 | 99 | 6% | 1.1 |
| TSHC | H19 + RH5B | VH-2 + VH-4 | 4 ng DgX | 135 | 7% | 1.4 |
| TSHC | H19 + RH5B | VH-2 + VH-4 | 4 ng 1066 | 107 | 7% | 1.1 |
| HC II | H19 + RH5B | None | 0 | 94 | 9% | 1.0 |
| HC II | H19 + RH5B | None | 4 ng pBS SK+ | 4498 | 3% | 48.1 |
| HC II | H19 + RH5B | None | 2 ng pBR322 | 1281 | 8% | 13.7 |
| HC II | H19 + RH5B | None | 4 ng DgX | 2003 | 5% | 21.4 |
| HC II | H19 + RH5B | None | 4 ng 1066 | 1536 | 2% | 16.4 |

Example 10

Sensitivity and Specificity of Detecting HSV-1 and HSV-2 by TSHC

Figure 4:
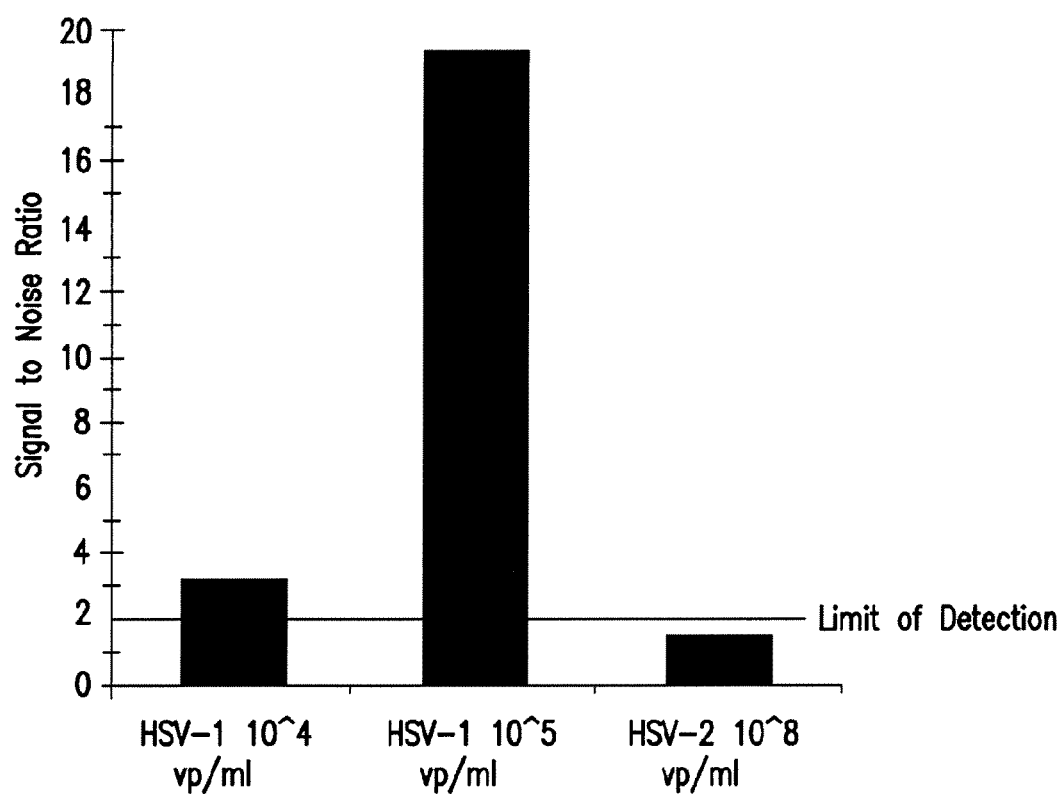
FIG. 4 shows the analytical sensitivity and specificity of targetspecific hybrid capture detection of HSV-1.
Figure 5:
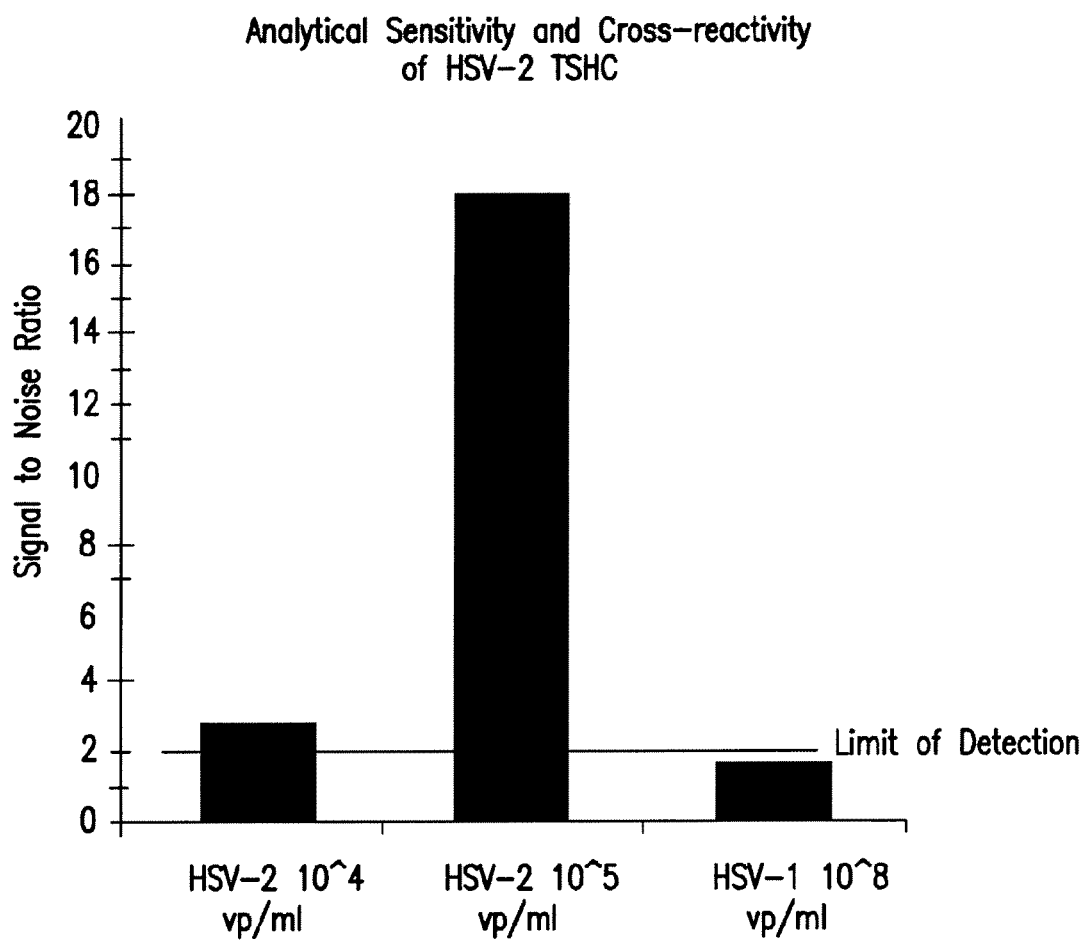
FIG. 5 shows the analytical sensitivity and specificity of targetspecific hybrid capture detection of HSV-2.

The sensitivity and typing discrimination for the TSHC detection of HSV-1 and HSV-2 were assessed using the TSHC described in Example 1. In the HSV-1 TSHC assay, signal sequence probes H19 and RH5B, capture sequence probes HZ-1, VH-2 and VH-4, and blocker probes NG-7, NG-8, GP-3, GP-4, and GP-1 were used. In the HSV-2 TSHC assay, signal sequence probes 18 and Ei8, capture sequence probes NF-1 and NF-2, and blocker probes HX-4, HX-5 and GP-8 were used. HSV-1 and HSV-2 viral particles were diluted to various concentrations using the Negative Control Solution. As shown in FIGS. 4 and 5, while $10^4$ copies of the either HSV-1 or HSV-2 (450 copies/well) were detected in the respective assays, there was virtually no detection of the cross-reactive type HSV at concentrations up to and including 108 copies/ml (4,500,000 copies/well). Thus, the HSV-1 and HSV-2 TSHC assays can distinguish the two HSV types at a greater than 10.000-fold range of discrimination while maintaining excellent sensitivity (450 VP/well).

The HSV-1 TSHC assay shows a linear range of detection ranging from at least $2 \times 10^3$ to $5 \times 10^3$ VP/ml (Table 17). The specificity of the assay is excellent as no cross-reactivity was detected (S/N is less than or equal to 2) in samples containing HSV-2 at a concentration as high as $2 \times 10^7$ to $5 \times 10^7$ viral particles/ml. Similarly, the HSV-2 TSHC assay also shows excellent specificity, wherein no crossreactivity was detected in samples containing HSV-1 at a concentration as high as $5 \times 10^7$ viral particles/ml (Table 18). Similar results were obtained from TSHC detection of HSV-2 using a dilution series of HSV-2 and HSV-1 viruses (Table 19).

TABLE 17

Analytical Sensitivity and Specificity of the HSV1 TSHC Assay

| Targets | RLU | S/N |
|---|---|---|
| Negative Control | 47 | 1.0 |
| HSV2 @ $5 \times 10^7$ VP/ml | 57 | 1.2 |
| HSV2 @ $2 \times 10^7$ VP/ml | 43 | 0.9 |
| HSV1 @ $5 \times 10^3$ VP/ml | 201 | 4.3 |
| HSV1 @ $2 \times 10^3$ VP/ml | 107 | 2.3 |

TABLE 18

Analytical Sensitivity and Specificity of the HSV2 TSHC Assay

| Targets | RLU | S/N |
|---|---|---|
| Negative Control | 40 | 1.0 |
| HSV1 @ 5 × 10^7 VP/ml | 78 | 2.0 |
| HSV1 @ 2 × 10^7 VP/ml | 55 | 1.4 |
| HSV2 @ 5 × 10^3 VP/ml | 218 | 5.5 |
| HSV2 @ 2 × 10^3 VP/ml | 106 | 2.7 |

TABLE 19

Detection with HSV-2 Probes using HSV-1 and HSV-2 of Different Dilution

| Targets | RLU | S/N |
|---|---|---|
| Negative Control | 43 | 1.0 |
| HSV1 @ 5 × 10^7 VP/ml | 112 | 2.6 |
| HSV1 @ 2 × 10^7 VP/ml | 57 | 1.3 |
| HSV1 @ 1 × 10^7 VP/ml | 38 | 0.9 |
| HSV1 @ 1 × 10^6 VP/ml | 38 | 0.9 |
| HSV1 @ 1 × 10^5 VP/ml | 33 | 0.8 |
| HSV1 @ 1 × 10^4 VP/ml | 52 | 1.2 |
| HSV1 @ 1 × 10^3 VP/ml | 43 | 1.0 |
| HSV1 @ 1 × 10^2 VP/ml | 39 | 0.9 |
| HSV2 @ 1 × 10^7 VP/ml | 257173 | 5980.8 |
| HSV2 @ 1 × 10^6 VP/ml | 28544 | 663.8 |
| HSV2 @ 1 × 10^5 VP/ml | 3200 | 74.4 |
| HSV2 @ 1 × 10^4 VP/ml | 266 | 6.2 |
| HSV2 @ 5 × 10^3 VP/ml | 181 | 4.2 |
| HSV2 @ 1 × 10^3 VP/ml | 62 | 1.4 |
| HSV2 @ 1 × 10^2 VP/ml | 44 | 1.0 |

Example 11

Clinical Specimen Testing

A 64-member clinical specimen panel was tested for HSV-1 and HSV2 using both TSHC and HCII methods. The panel included 15 samples containing known quantities of HSV-1 or HSV-2, and 49 samples known to be negative for HSV1 and HSV-2 by PCR testing. Accordingly, the 15 positive samples were "Expected" to test positive in both the HCII and TSHC assays, and the 49 negative samples were "Expected" to test negative in both the HCII and TSHC tests.

The general TSHC method described in Example 1 was employed. The results using the HCII method and the TSHC method are shown in Tables 20 and 21, respectively. Of the 49 samples "Expected" to yield negative result, 5 samples tested positive and 44 samples tested positive using the HCII method. In comparison, all 49 samples tested negative using the TSHC method. Therefore, the TSHC method is superior in specificity to the HCII method in the detection of HSV-1 and HSV-2.

TABLE 20

Observed vs. Expected Results for HCII Detection of HSV1 and HSV2

| | Expected Result | |
|---|---|---|
| HCII Result | Positive | Negative |
| Positive | 15 | 5 |
| Negative | 0 | 44 |
| Total | 15 | 49 |

TABLE 21

Observed vs. Expected Results for TSHC Detection of HSV1 and HSV2

| | Expected Result | |
|---|---|---|
| TSHC Result | Positive | Negative |
| Positive | 14 | 0 |
| Negative | 1 | 49 |
| Total | 15 | 49 |

Example 12

Effect of Combining Probes in TSHC Detection of HSV

The effect of combining HSV-1 specific signal sequence probe and capture sequence probe sets on HSV-1 detection was assessed. TSHC detection of HSV-1 and HSV-2 cross-reactivity was performed separately with two different sets of RNA signal sequence probe/biotinylated capture sequence probe combinations (Set #1: H19 plus HZ-1; and Set #2: RH5b plus the TS-1 and TS-2). TSHC was also performed with both RNA signal sequence probe/biotinylated capture sequence probe sets combined to assess the effect of combining the two probe sets on sensitivity and cross-reactivity. The general TSHC method described in Example 1 was employed. The results shown in Table 22 clearly demonstrate an additive effect of combining the two probe sets for HSV-1 detection with no apparent increase in HSV-2 cross-reactivity.

TABLE 22

Sensitivity is Improved by Combining HSV-1 Specific CSPs and SSPs

| Capture Sequence Probes | Signal Sequence Probes | VP/ml | RLU | CV | S/N |
|---|---|---|---|---|---|
| HZ-1 | H19 | 0 | 60 | 3% | 1.0 |
| HZ-1 | H19 | 10^5 HSV-1 | 267 | 4% | 4.5 |
| HZ-1 | H19 | 10^6 HSV-1 | 2316 | 6% | 38.9 |
| HZ-1 | H19 | 10^7 HSV2 | 49 | 2% | 0.8 |
| TS-1, TS-2 | RH5B | 0 | 78 | 6% | 1.0 |
| TS-1, TS-2 | RH5B | 10^5 HSV-1 | 291 | 6% | 3.8 |
| TS-1, TS-2 | RH5B | 10^6 HSV-1 | 2368 | 11% | 30.6 |
| TS-1, TS-2 | RH5B | 10^7 HSV2 | 75 | 11% | 1.0 |
| HZ-1, TS-1, TS-2 | H19, RH5B | 0 | 70 | 12% | 1.0 |
| HZ-1, TS-1, TS-2 | H19, RH5B | 10^5 HSV-1 | 457 | 10% | 6.5 |
| HZ-1, TS-1, TS-2 | H19, RH5B | 10^6 HSV-1 | 4263 | 1% | 60.9 |
| HZ-1, TS-1, TS-2 | H19, RH5B | 10^7 HSV2 | 67 | 6% | 1.0 |

Example 13

TSHC Detection of HPV18 and HPV45

The relative sensitivity and specificity of TSHC and HCII detection of Human Papillomavirus 18 (HPV18) and Human Papillomavirus 45 (HPV45) was compared. Previous studies have established HPV45 as the most cross-reactive HPV type to HPV18, and conversely, HPV18 as the most cross-reactive HPV type to HPV45. In this study, the ability of the two methods to detect HPV18 and HPV45 was assessed using HPV18 and HPV45 plasmid DNA.

Capture sequence probes (CSPs) for each of the four Human Papillomavirus types: HPV16, HPV18, HPV31, and HPV45, were designed. The criteria used for designing the capture sequence probes were: 1) the CSP hybridization sites do not overlap with the SSP sites; 2) the CSPs contain sequences unique to one HPV type with no stretches of sequence homology to other HPV types greater than 12 bases; and 3) the CSPs are of sufficient length so as to be capable of hybridizing efficiently at 70° C.

The blocker probes for each CSP were designed such that they could be added simultaneously with the CSP during hybridization to the target nucleic acid. The blocker probes have a melting temperature of at least 37° C. but no higher than 60° C., as calculated by the Oligo 5.0 program (National Biosciences, Inc., Plymouth, Minn.). Two blocker probes were used for each capture oligonucleotide to maximize the blocker effect during the room temperature plate capture step. It was also desired that the blocker probes for each CSP have similar melting temperatures.

CSPs for each of the HPV types were tested for relative capture efficiency and cross-reactivity to other HPV types. CSPs that provided the best combination of sensitivity and low cross-reactivity were used for the detection of HPV using TSHC.

In TSHC and HCII detection of HPV18, HPV18 DNA was used at a concentration of 10 pg/ml. HPV45, used for cross-reactivity testing, was used at 4 ng/ml. The general TSHC method described in Example 1 was employed. As shown in Table 23, a signal to noise ratio of 16.9 was obtained for TSHC detection of HPV18 compared to a ratio of 7.6 obtained for HCII detection of HPV18. On the other hand, cross-reactivity with HPV45 was significantly reduced using the TSHC method (S/N of 1.3 for TSHC compared to S/N of 393.3 for HCII). The results clearly show that compared to the HCII method, the TSHC method for the detection of HPV18 was superior in both sensitivity and specificity. Results obtained in experiments comparing TSHC and HCII detection of HPV45 demonstrate that the TSHC method for the detection of HPV45 is superior in both sensitivity and specificity (Table 24).

TABLE 23

TSHC Detection of HPV 18

| Method | Target | SSP | CSP | S/N |
|---|---|---|---|---|
| TSHC | 0 | 18L1 | 18-7L | 1.0 |
| | HPV18 (10 pg/nal) | 18L1 | 18-7L | 16.9 |
| | HPV45 (4 ng/nal) | 18L1 | 18-7L | 1.3 |
| HC II | 0 | 18L1 | none | 1.0 |
| | HPV18 (10 pg/nal) | 18L1 | none | 7.6 |
| | HPV45 (4 ng/nal) | 18L1 | none | 393.3 |

TABLE 24

TSHC Detection of HPV 45

| Method | Target | SSP | CSP | S/N |
|---|---|---|---|---|
| TSHC | 0 | 45L1 | ON-1 | 1.0 |
| | HPV45 (10 pg/nal) | 45L1 | ON-1 | 8.4 |
| | HPV18 (4 ng/nal) | 45L1 | ON-1 | 1.6 |
| HC II | 0 | 45L1 | none | 1.0 |
| | HPV45 (10 pg/nal) | 45L1 | none | 8.2 |
| | HPV18 (4 ng/nal) | 45L1 | none | 494.0 |

Example 14

Target-Specific Hybrid Capture-Plus Assay Protocol

Hepatitis B Virus (HBV) was used as the model system for the development of the target-specific hybrid capture-plus (TSHC-plus) assay for the detection of target nucleic acids.

The hybridization in the TSHC-plus method (FIG. 6A-6D) may be performed in a single step. In the one-step method, CSPs, SSPs containing prehybridized DNA-RNA duplex, bridge probes (FIG. 6B-6D), and blocker probes are added simultaneously to the target nucleic acids. If hybridization is performed in two steps, CSPs, SSPs without pre-hybridized DNA-RNA duplex, bridge probes and blocker probes are first hybridized to the target nucleic acid. Oligonucleotide probes complementary to the single stranded nucleic acid sequence in the SSP are then added to the reaction to form the DNA-RNA duplexes. The hybrids are then detected using anti-RNA/DNA antibody as described in Example 1.

Experiments were carried out to detect HBV using TSHC-plus (Examples 15-18). The method shown in FIG. 6A was used. Human hepatitis B virus (HBV adw2) plasmid DNA of known concentration (Digene Corp) was diluted using HBV negative Sample Diluent (Digene). Various dilutions were made and aliquoted into individual tubes. The negative Sample Diluent was used as a negative control. A half volume of the Denaturation Reagent 5100-0431 (Digene) was added to the test samples. Test samples were incubated at 65° C. for 45 minutes to denature the nucleic acids in the samples.

Following denaturation of the HBV sample, a hybridization solution containing capture sequence probes (CSPs), blocker probes, signal sequence probe comprising a M13 DNA/M13 RNA duplex and a single-stranded DNA sequence capable of hybridizing to HBV sequences was added to the samples, and incubated at 65° C. for 1-2 hours. Alternatively, the denatured samples were incubated for 1 hour with a hybridization solution containing capture sequence probes (CSPs), blocker probes and M13 DNA plasmid containing HBV complementary sequences for 1 hour. Following the incubation, M13 RNA was added to the reaction and the incubation was continued for an additional hour at 65° C.

Tubes containing reaction mixtures were cooled at room temperature for 5 minutes and aliquots were taken from each tube and transferred to individual wells of a 96-well streptavidin plate (Digene). The plates were shaken at 1100 rpms for 1 hour at room temperature. The solution was then decanted and the plates were washed four times with SNM wash buffer (Digene). The alkaline-phosphatase antiRNA/DNA antibody DR-I (Digene) was added to each well and incubated for 30 minutes at room temperature. The DR-1 (Digene) was then decanted and the plates were washed four times with SNM wash buffer (Digene). Following removal of the residual wash buffer, luminescent substrate (CDP-Star, Tropix Inc.) was added to each well and incubated for 15 minutes at room temperature. Individual wells were read on a plate luminometer to obtain relative light unit (RLU) signals.

Example 15

The Following Tables Describe the Various Probes Tested in the Experiments Described in Examples 16-18

TABLE 25

| Probe | Sequence | Size (bp) | Location within HBV | Strand |
|---|---|---|---|---|
| HBV C1 | GCTGGATGTGTCTGCGGCGTTTTATCAT (SEQ ID NO: 152) | 28 | 374-401 | Sense |

TABLE 25-continued

| Probe | Sequence | Size (bp) | Location within HBV | Strand |
|---|---|---|---|---|
| HBV C2 | ACTGTTCAAGCCTCCAAGCTG CGCCTT (SEQ ID NO: 153) | 27 | 1861-1877 | Sense |
| HBV C3 | ATGATAAAACGCCGCAGACAC ATCCAGCGATA (SEQ ID NO: 154) | 32 | 370-401 | Anti-sense |

TABLE 26

HBV/M13 Clones from which SSPs are Prepared

| Clone name | Vector | Cloning site | Insert Size (bp) | Location within HBV |
|---|---|---|---|---|
| SA1 | M13 mp 18 | Eco RI, Hind III | 35 | 194-228 |
| SA2 | M13 mp 18 | Eco RI, Hind III | 34 | 249-282 |
| SA1a | M13 mp 19 | Eco RI, Hind III | 35 | 194-228 |
| SA2a | M13 mp 19 | Eco RI, Hind III | 34 | 249-282 |
| SA4 | M13 mp 19 | Eco RI, Hind III | 87 | 1521-1607 |

TABLE 27

HBV Blocker probes

| Probe | Sequence | Size (bp) | CSP to which it hybridizes |
|---|---|---|---|
| B1 | ATGATAAAACGCCG (SEQ ID NO:155) | 14 | HBV C1 |
| B2 | CAGACACATCCAGC (SEQ ID NO: 156) | 14 | HBV C1 |
| B3 | AAGGCACAGCTTG (SEQ ID NO: 157) | 13 | HBV C2 |
| B4 | GAGGCTTGAACAGT (SEQ ID NO: 158) | 14 | HBV C2 |
| B5 | TATCGCTGGATGTGTC (SEQ ID NO: 159) | 16 | HBV C3 |
| B6 | TCGGCGTTTTATCATG (SEQ ID NO: 160) | 16 | HBV C3 |

Example 16

Effect of Blocker Probes on TSHC-Plus Detection of HBV

During room temperature capture step, excess SSP (M13 RNA/HBVM13 DNA duplex) non-specifically hybridizing to the CSP are immobilized onto the plate which results in high background signals. In an attempt to reduce background signal, blocker probes were employed in TSHC-Plus detection of HBV. The blocker probes were designed to be much shorter than the CSPs so that they are only capable of hybridizing to the capture probes at temperatures well below the hybridization temperatures used in the assay.

Blocker probe sets consisting of two separate oligonucleotides that are complementary to the CSPs were used. The blocker probes were added to the hybridization mixture in 10-fold excess relative to the CSPs. Since the blocker probes are much shorter than the CSPs, they do not hybridize with CSPs at the target hybridization temperature and therefore do not interfere with the hybridization of the CSPs to the target nucleic acids. Following the hybridization of CSP and target nucleic acids, the samples were subjected to a room temperature capture step during which the blocker probes hybridize with excess CSPs, thus preventing them from hybridizing to the SSPs. As shown in Table 28, the use of the blocker probes in the hybridization reaction greatly reduced the background signals of the assay.

TABLE 28

Effect of Blocker Probes on HBV Detection

| Capture Probe | Blocker probe | Background Signal (RLU) |
|---|---|---|
| HBV C1 | no | 17892 |
| HBV C1 | B1, B2 | 424 |
| HBV C2 | no | 9244 |
| HBV C2 | B3, B4 | 398 |

Example 17

Effect of the Length of SSP on TSHC-Plus Detection of HBV

The effect of the length of the DNA sequence inserted into the M13 vector for generating the SSP on TSCH-Plus detection of HBV was studied. A positive control containing 20 pg/ml of HBV plasmid DNA was used. As shown in Table 29, the use of a longer HBV complementary sequence in the SSP (87 base pairs) resulted in a substantial increase in signal of detection. The effect is unlikely due to sub-optimal hybridization temperature condition since the Tm of the shorter probes is 15 degree above the hybridization temperature. As the M13 RNA-DNA duplex formed in the SSP may act to partially block the complementary DNA sequence in the probe from hybridizing to the HBV sequences in the target nucleic acids, longer complementary sequences in the SSP may overcome this block.

TABLE 30

TSHC-Plus and HC II Detection of HBV*

| | | Target HBV Concentration | | |
|---|---|---|---|---|
| Method | Control | 10 pg/ml | 20 pg/ml | 100 pg/ml |
| HC II | 48 | 2355 | 4225 | 21438 |
| TSHC Plus | 285 | 4856 | 7978 | 37689 |

*Signal measured as relative light unit (RLU)

Example 18

TSHC-Plus and HC II Detection of HBV

The relative sensitivity of TSHC-Plus and HC II (Hybrid Capture II, Digene) detection of HBV was compared. HBV positive standards of three different concentrations were tested in the experiments. As shown in Table 30, the signals obtained using the TSHC-Plus detection method were approximately two-fold higher than those obtained using the HC II detection method.

TABLE 29

Effect of the Length of the Complementary sequence in the SSP on TSHC-Plus Detection of HBV

| SSP | Size of the HBV Target DNA Sequence in SSP (bp) | Tm of the HBV Target DNA Sequence in SSP | Hybridization temperature | Signal (RLU) |
|---|---|---|---|---|
| SA1 | 35 | 83° C. | 65° C. | 1741 |
| SA2 | 34 | 80° C. | 65° C. | 1857 |
| SA4 | 87 | 108° C. | 65° C. | 7978 |

The above description of various preferred embodiments has been presented for purposes of illustration and description. It is not intended to be exhaustive or limiting to the precise forms disclosed. Obvious modifications or variations are possible in light of the above teachings. The embodiments discussed were chosen and described to provide illustrations and its practical application to thereby enable one of ordinary skill in the art to utilize the various embodiments and with various modifications as are suited to the particular use contemplated. All such modifications and variations are within the system as determined by the appended claims when interpreted in accordance with the breadth to which they are fairly, legally and equitably entitled.

We claim:

1. An isolated nucleic acid probe:
   (a) having an overall length of 100 nucleotides or less;
   (b) comprising a first nucleotide sequence selected from the group consisting of SEQ ID NO: 75 to SEQ ID NO: 78, a full length complement thereof, and an RNA equivalent thereof; and
   (c) capable of hybridizing to a Human papillomavirus type 16 (HPV 16) nucleic acid under moderately stringent hybridization conditions.

2. The nucleic acid probe of claim 1 having an overall length of 40 nucleotides or less.

3. The nucleic acid probe of claim 1 consisting of a nucleotide sequence selected from the group consisting of SEQ ID NO: 75 to SEQ ID NO: 78, a full-length complement thereof, and an RNA equivalent thereof.

4. The nucleic acid probe of claim 1, wherein the nucleic acid probe is modified with at least one ligand.

5. The nucleic acid probe of claim 4, wherein the ligand is selected from the group consisting of biotin, digoxigenin, and 2,4-dinitrophenol.

6. The nucleic acid probe of claim 4, wherein the nucleic acid probe is linear having a 5' and 3' end, wherein both the 5' and the 3' ends are modified with a ligand.

7. The nucleic acid probe of claim 6, wherein the ligand at the 5' and the 3' ends is biotin.

8. The nucleic acid probe of claim 1, wherein the nucleic acid probe is modified with at least one fluorogen.

9. The nucleic acid probe of claim 8, wherein the fluorogen is selected from the group consisting of fluorescein and derivatives thereof, phycoerythrin, allo-phycocyanin, phycocyanin, rhodamine, and Texas Red.

10. The nucleic acid probe of claim 1 further comprising:
    (d) a second nucleotide sequence at least 75% identical to a sequence selected from the group consisting of SEQ ID NO:1 through SEQ ID:29, SEQ ID NO:50 through SEQ ID NO:62, SEQ ID NO:75 through SEQ ID NO:109, and SEQ ID NO:152 through SEQ ID NO:154, a full length complement thereof, and an RNA equivalent thereof,
    wherein the first and second nucleotide sequences are capable of hybridizing either to different regions of the same HPV 16 nucleic acid or to different viral nucleic acids.

11. The nucleic acid probe of claim 10, wherein the first and second nucleotide sequences are capable of hybridizing to different regions of the same HPV 16 nucleic acid and wherein said different regions are 3 kilobases or less apart.

12. The nucleic acid probe of claim 10, wherein the first and second nucleotide sequences are capable of hybridizing to different regions of the same HPV 16 nucleic acid and wherein said different regions are 500 bases or less apart.

13. The nucleic acid probe of claim 1 comprising: a single stranded region comprising the first nucleotide sequence; and a region comprising a DNA-RNA duplex.

14. The nucleic acid probe of claim 13, wherein the DNA-RNA duplex is an M13 DNA-M13 RNA duplex.

15. The nucleic acid probe of claim 1 further comprising a region capable of hybridizing to a poly(A) tail or a poly(dT) tail under moderately stringent hybridization conditions.

16. The nucleic acid probe of claim 1 further comprising a region capable of hybridizing to a second nucleic acid probe under moderately stringent hybridization conditions.

17. The nucleic acid probe of claim 1, wherein said nucleic acid probe is DNA, RNA, or PNA.

18. A blocker probe capable of hybridizing to a nucleic acid probe of claim 1 under moderate stringency conditions, wherein said blocker probe comprises a first sequence at least 5 nucleotides in length, said first sequence sharing at least 75% identity over its entire length with a sequence selected from the group consisting of SEQ ID NO: 122 through SEQ ID NO: 129, or a full length complement thereof, and wherein said blocker probe is at least 75% complementary to the full length of the nucleic acid probe.

19. The blocker probe of claim 18 wherein said blocker probe has a predicted melting temperature at least 10° C. lower than the predicted melting temperature of the nucleic acid probe.

20. The blocker probe of claim 18 wherein said blocker probe comprises a nucleotide sequence selected from the group consisting of SEQ ID NO: 122 through SEQ ID NO: 129, or a full length complement thereof.

21. The blocker probe of claim 18 wherein said blocker probe consists of a nucleotide sequence selected from the group consisting of SEQ ID NO: 122 through SEQ ID NO: 129 or a full length complement thereof.

22. The blocker probe of claim 18 wherein said blocker probe is at least 12 nucleotides in length.

23. The blocker probe of claim 18 wherein said blocker probe is 100% complementary to the full length of the nucleic acid probe.

24. A kit for detecting HPV 16, said kit comprising:
    (a) at least one capture sequence probe, capable of hybridizing to a first region of an HPV 16 nucleic acid, wherein said capture sequence probe is bound to a solid phase or adapted to be bound to a solid phase;
(b) at least one blocker sequence probe capable of hybridizing to the capture sequence probe; and
(c) at least one signal sequence probe capable of hybridizing to a second region of the HPV 16 nucleic acid, wherein the signal sequence probe does not hybridize to the capture sequence probe and wherein the second region of the HPV 16 nucleic acid does not overlap with the first region of the HPV 16 nucleic acid and wherein the distance between the second region of the HPV 16 nucleic acid and the first region of the HPV 16 nucleic acid is 1000 bases or less;

wherein the capture sequence probe and/or the signal sequence probe is a nucleic acid probe of claim 1.

25. The kit of claim 24 further comprising a solid phase.

26. The kit of claim 24 wherein said signal sequence probe is detectably labeled.

27. A kit for detecting an HPV 16 nucleic acid, said kit comprising:
(a) at least one capture sequence probe capable of hybridizing to an HPV 16 nucleic acid, wherein said capture sequence probe is bound to a solid phase or adapted to be bound to a solid phase;
(b) at least one blocker sequence probe capable of hybridizing to the capture sequence probe;
(c) at least one bridge probe comprising a first sequence capable of hybridizing to a second region of the HPV 16 nucleic acid; and
(d) at least one signal sequence probe capable of hybridizing to the bridge probe and not capable of hybridizing to the HPV 16 nucleic acid;

wherein the capture sequence probe and/or the bridge probe is a nucleic acid probe of claim 1.

28. The kit of claim 27 further comprising a solid phase.

29. The kit of claim 27 wherein said signal sequence probe is detectably labeled.

30. The nucleic acid probe of claim 1, with the proviso that the nucleic acid probe does not contain any stretches of sequence homology to other HPV types greater than 12 bases.

31. The kit of claim 24, with the proviso that the capture sequence probe does not contain any stretches of sequence homology to other HPV types greater than 12 bases and is of sufficient length so as to be capable of hybridizing efficiently at 70° C.

\* \* \* \* \*

SEQUENCE LISTING

```
<160> NUMBER OF SEQ ID NOS: 160

<210> SEQ ID NO 1
<211> LENGTH: 42
<212> TYPE: DNA
<213> ORGANISM: Artificial Sequence
<220> FEATURE:
<223> OTHER INFORMATION: TS-1
<220> FEATURE:
<223> OTHER INFORMATION: Description of Artificial Sequence:nucleic acid
      probe

<400> SEQUENCE: 1
ttattattac gttcatgtcg gcaaacagct cgtttattat ta                         42

<210> SEQ ID NO 2
<211> LENGTH: 39
<212> TYPE: DNA
<213> ORGANISM: Artificial Sequence
<220> FEATURE:
<223> OTHER INFORMATION: TS-2
<220> FEATURE:
<223> OTHER INFORMATION: Description of Artificial Sequence:nucleic acid
      probe

<400> SEQUENCE: 2
ttattattac gtcctggatg gcgatacggc ttattatta                             39

<210> SEQ ID NO 3
<211> LENGTH: 21
<212> TYPE: DNA
<213> ORGANISM: Artificial Sequence
<220> FEATURE:
<223> OTHER INFORMATION: VH-3
<220> FEATURE:
<223> OTHER INFORMATION: Description of Artificial Sequence:nucleic acid
      probe

<400> SEQUENCE: 3
cgtcctggat ggcgatacgg c                                                21

<210> SEQ ID NO 4
<211> LENGTH: 24
<212> TYPE: DNA
<213> ORGANISM: Artificial Sequence
<220> FEATURE:
<223> OTHER INFORMATION: NC-1
<220> FEATURE:
<223> OTHER INFORMATION: Description of Artificial Sequence:nucleic acid
      probe

<400> SEQUENCE: 4
cgttcatgtc ggcaaacagc tcgt                                             24
```

```
<210> SEQ ID NO 5
<211> LENGTH: 45
<212> TYPE: DNA
<213> ORGANISM: Artificial Sequence
<220> FEATURE:
<223> OTHER INFORMATION: VH-4
<220> FEATURE:
<223> OTHER INFORMATION: Description of Artificial Sequence:nucleic acid
      probe

<400> SEQUENCE: 5
cgttcatgtc ggcaaacagc tcgtcgtcct ggatggcgat acggc            45

<210> SEQ ID NO 6
<211> LENGTH: 34
<212> TYPE: DNA
<213> ORGANISM: Artificial Sequence
<220> FEATURE:
<223> OTHER INFORMATION: HZ-1
<220> FEATURE:
<223> OTHER INFORMATION: Description of Artificial Sequence:nucleic acid
      probe

<400> SEQUENCE: 6
gatggggtta tttttcctaa gatggggcgg gtcc                        34

<210> SEQ ID NO 7
<211> LENGTH: 28
<212> TYPE: DNA
<213> ORGANISM: Artificial Sequence
<220> FEATURE:
<223> OTHER INFORMATION: VH-2
<220> FEATURE:
<223> OTHER INFORMATION: Description of Artificial Sequence:nucleic acid
      probe

<400> SEQUENCE: 7
taccccgatc atcagttatc cttaaggt                               28

<210> SEQ ID NO 8
<211> LENGTH: 19
<212> TYPE: DNA
<213> ORGANISM: Artificial Sequence
<220> FEATURE:
<223> OTHER INFORMATION: FD-1
<220> FEATURE:
<223> OTHER INFORMATION: Description of Artificial Sequence:nucleic acid
      probe

<400> SEQUENCE: 8
aaaccgttcc atgaccgga                                         19

<210> SEQ ID NO 9
<211> LENGTH: 22
<212> TYPE: DNA
<213> ORGANISM: Artificial Sequence
<220> FEATURE:
<223> OTHER INFORMATION: RA-2
<220> FEATURE:
<223> OTHER INFORMATION: Description of Artificial Sequence:nucleic acid
      probe

<400> SEQUENCE: 9
atcgcgtgtt ccagagacag gc                                     22

<210> SEQ ID NO 10
<211> LENGTH: 17
<212> TYPE: DNA
<213> ORGANISM: Artificial Sequence
```

```
<220> FEATURE:
<223> OTHER INFORMATION: NC-2
<220> FEATURE:
<223> OTHER INFORMATION: Description of Artificial Sequence:nucleic acid
      probe

<400> SEQUENCE: 10
caacgcccaa aataata                                                        17

<210> SEQ ID NO 11
<211> LENGTH: 20
<212> TYPE: DNA
<213> ORGANISM: Artificial Sequence
<220> FEATURE:
<223> OTHER INFORMATION: FD-2
<220> FEATURE:
<223> OTHER INFORMATION: Description of Artificial Sequence:nucleic acid
      probe

<400> SEQUENCE: 11
gtccccgaac cgatctagcg                                                     20

<210> SEQ ID NO 12
<211> LENGTH: 22
<212> TYPE: DNA
<213> ORGANISM: Artificial Sequence
<220> FEATURE:
<223> OTHER INFORMATION: RA-4
<220> FEATURE:
<223> OTHER INFORMATION: Description of Artificial Sequence:nucleic acid
      probe

<400> SEQUENCE: 12
cgaaccataa accattcccc at                                                  22

<210> SEQ ID NO 13
<211> LENGTH: 25
<212> TYPE: DNA
<213> ORGANISM: Artificial Sequence
<220> FEATURE:
<223> OTHER INFORMATION: ON-3
<220> FEATURE:
<223> OTHER INFORMATION: Description of Artificial Sequence:nucleic acid
      probe

<400> SEQUENCE: 13
cacgcccgtg gttctggaat tcgac                                               25

<210> SEQ ID NO 14
<211> LENGTH: 41
<212> TYPE: DNA
<213> ORGANISM: Artificial Sequence
<220> FEATURE:
<223> OTHER INFORMATION: HZ-2
<220> FEATURE:
<223> OTHER INFORMATION: Description of Artificial Sequence:nucleic acid
      probe

<400> SEQUENCE: 14
tttattagat ggggttattt ttcctaagat ggggcgggtc c                             41

<210> SEQ ID NO 15
<211> LENGTH: 16
<212> TYPE: DNA
<213> ORGANISM: Artificial Sequence
<220> FEATURE:
<223> OTHER INFORMATION: ZD-1
<220> FEATURE:
<223> OTHER INFORMATION: Description of Artificial Sequence:nucleic acid
      probe
```

```
<400> SEQUENCE: 15
ggttattttt cctaag                                                        16

<210> SEQ ID NO 16
<211> LENGTH: 28
<212> TYPE: DNA
<213> ORGANISM: Artificial Sequence
<220> FEATURE:
<223> OTHER INFORMATION: ZD-2
<220> FEATURE:
<223> OTHER INFORMATION: Description of Artificial Sequence:nucleic acid
      probe

<400> SEQUENCE: 16
attattggtt attttttccta agattatt                                          28

<210> SEQ ID NO 17
<211> LENGTH: 40
<212> TYPE: DNA
<213> ORGANISM: Artificial Sequence
<220> FEATURE:
<223> OTHER INFORMATION: F6R
<220> FEATURE:
<223> OTHER INFORMATION: Description of Artificial Sequence:nucleic acid
      probe

<400> SEQUENCE: 17
acgacgccct tgactccgat tcgtcatcgg atgactccct                              40

<210> SEQ ID NO 18
<211> LENGTH: 32
<212> TYPE: DNA
<213> ORGANISM: Artificial Sequence
<220> FEATURE:
<223> OTHER INFORMATION: BRH19
<220> FEATURE:
<223> OTHER INFORMATION: Description of Artificial Sequence:nucleic acid
      probe

<400> SEQUENCE: 18
atgcgccagt gtatcaatca gctgtttcgg gt                                      32

<210> SEQ ID NO 19
<211> LENGTH: 38
<212> TYPE: DNA
<213> ORGANISM: Artificial Sequence
<220> FEATURE:
<223> OTHER INFORMATION: F15R
<220> FEATURE:
<223> OTHER INFORMATION: Description of Artificial Sequence:nucleic acid
      probe

<400> SEQUENCE: 19
caaaacgtcc tggagacggg tgagtgtcgg cgaggacg                                38

<210> SEQ ID NO 20
<211> LENGTH: 20
<212> TYPE: DNA
<213> ORGANISM: Artificial Sequence
<220> FEATURE:
<223> OTHER INFORMATION: VH-1
<220> FEATURE:
<223> OTHER INFORMATION: Description of Artificial Sequence:nucleic acid
      probe

<400> SEQUENCE: 20
gtccccgacc cgatctagcg                                                    20
```

```
<210> SEQ ID NO 21
<211> LENGTH: 23
<212> TYPE: DNA
<213> ORGANISM: Artificial Sequence
<220> FEATURE:
<223> OTHER INFORMATION: ON-4
<220> FEATURE:
<223> OTHER INFORMATION: Description of Artificial Sequence:nucleic acid
      probe

<400> SEQUENCE: 21
gcagactgcg ccaggaacga gta                                           23

<210> SEQ ID NO 22
<211> LENGTH: 35
<212> TYPE: DNA
<213> ORGANISM: Artificial Sequence
<220> FEATURE:
<223> OTHER INFORMATION: PZ-1
<220> FEATURE:
<223> OTHER INFORMATION: Description of Artificial Sequence:nucleic acid
      probe

<400> SEQUENCE: 22
gtgcccacgc ccgtggttct ggaattcgac agcga                              35

<210> SEQ ID NO 23
<211> LENGTH: 35
<212> TYPE: DNA
<213> ORGANISM: Artificial Sequence
<220> FEATURE:
<223> OTHER INFORMATION: PZ-2
<220> FEATURE:
<223> OTHER INFORMATION: Description of Artificial Sequence:nucleic acid
      probe

<400> SEQUENCE: 23
gcagactgcg ccaggaacga gtagttggag tactg                              35

<210> SEQ ID NO 24
<211> LENGTH: 36
<212> TYPE: DNA
<213> ORGANISM: Artificial Sequence
<220> FEATURE:
<223> OTHER INFORMATION: FG-2
<220> FEATURE:
<223> OTHER INFORMATION: Description of Artificial Sequence:nucleic acid
      probe

<400> SEQUENCE: 24
aagaggtcca ttgggtgggg ttgatacggg aaagac                             36

<210> SEQ ID NO 25
<211> LENGTH: 27
<212> TYPE: DNA
<213> ORGANISM: Artificial Sequence
<220> FEATURE:
<223> OTHER INFORMATION: FG-3
<220> FEATURE:
<223> OTHER INFORMATION: Description of Artificial Sequence:nucleic acid
      probe

<400> SEQUENCE: 25
cgtaatgcgg cggtgcagac tccctg                                        27

<210> SEQ ID NO 26
<211> LENGTH: 39
<212> TYPE: DNA
<213> ORGANISM: Artificial Sequence
```

```
<220> FEATURE:
<223> OTHER INFORMATION: FG-4
<220> FEATURE:
<223> OTHER INFORMATION: Description of Artificial Sequence:nucleic acid
      probe

<400> SEQUENCE: 26
ccaactaccc cgatcatcag ttatccttaa ggtctcttg                              39

<210> SEQ ID NO 27
<211> LENGTH: 47
<212> TYPE: DNA
<213> ORGANISM: Artificial Sequence
<220> FEATURE:
<223> OTHER INFORMATION: Hsv1-LF15R
<220> FEATURE:
<223> OTHER INFORMATION: Description of Artificial Sequence:nucleic acid
      probe

<400> SEQUENCE: 27
aaaaaaaaac aaaacgtcct ggagacgggt gagtgtcggc gaggacg                    47

<210> SEQ ID NO 28
<211> LENGTH: 38
<212> TYPE: DNA
<213> ORGANISM: Artificial Sequence
<220> FEATURE:
<223> OTHER INFORMATION: Hsv1-f15-2B
<220> FEATURE:
<223> OTHER INFORMATION: Description of Artificial Sequence:nucleic acid
      probe

<400> SEQUENCE: 28
caaaacgtcc tggagacggg tgagtgtcgg cgaggacg                              38

<210> SEQ ID NO 29
<211> LENGTH: 36
<212> TYPE: DNA
<213> ORGANISM: Artificial Sequence
<220> FEATURE:
<223> OTHER INFORMATION: Hsv1-F15-3B
<220> FEATURE:
<223> OTHER INFORMATION: Description of Artificial Sequence:nucleic acid
      probe

<400> SEQUENCE: 29
caaaacgtcc ggagacgggt gagtgcggcg aggacg                                36

<210> SEQ ID NO 30
<211> LENGTH: 18
<212> TYPE: DNA
<213> ORGANISM: Artificial Sequence
<220> FEATURE:
<223> OTHER INFORMATION: EA-1
<220> FEATURE:
<223> OTHER INFORMATION: Description of Artificial Sequence:nucleic acid
      probe

<400> SEQUENCE: 30
aggaaaaata accccatc                                                    18

<210> SEQ ID NO 31
<211> LENGTH: 15
<212> TYPE: DNA
<213> ORGANISM: Artificial Sequence
<220> FEATURE:
<223> OTHER INFORMATION: EA-2
<220> FEATURE:
<223> OTHER INFORMATION: Description of Artificial Sequence:nucleic acid
      probe
```

```
<400> SEQUENCE: 31
gacccgcccc atctt                                               15

<210> SEQ ID NO 32
<211> LENGTH: 34
<212> TYPE: DNA
<213> ORGANISM: Artificial Sequence
<220> FEATURE:
<223> OTHER INFORMATION: ZD-3
<220> FEATURE:
<223> OTHER INFORMATION: Description of Artificial Sequence:nucleic acid
      probe

<400> SEQUENCE: 32
ggacccgccc catcttagga aaataaccc catc                           34

<210> SEQ ID NO 33
<211> LENGTH: 13
<212> TYPE: DNA
<213> ORGANISM: Artificial Sequence
<220> FEATURE:
<223> OTHER INFORMATION: NG-7
<220> FEATURE:
<223> OTHER INFORMATION: Description of Artificial Sequence:nucleic acid
      probe

<400> SEQUENCE: 33
aaaaataacc cca                                                 13

<210> SEQ ID NO 34
<211> LENGTH: 11
<212> TYPE: DNA
<213> ORGANISM: Artificial Sequence
<220> FEATURE:
<223> OTHER INFORMATION: NG-8
<220> FEATURE:
<223> OTHER INFORMATION: Description of Artificial Sequence:nucleic acid
      probe

<400> SEQUENCE: 34
cgccccatct t                                                   11

<210> SEQ ID NO 35
<211> LENGTH: 15
<212> TYPE: DNA
<213> ORGANISM: Artificial Sequence
<220> FEATURE:
<223> OTHER INFORMATION: NG-4
<220> FEATURE:
<223> OTHER INFORMATION: Description of Artificial Sequence:nucleic acid
      probe

<400> SEQUENCE: 35
ccatcttagg aaaaa                                               15

<210> SEQ ID NO 36
<211> LENGTH: 15
<212> TYPE: DNA
<213> ORGANISM: Artificial Sequence
<220> FEATURE:
<223> OTHER INFORMATION: GP-1
<220> FEATURE:
<223> OTHER INFORMATION: Description of Artificial Sequence:nucleic acid
      probe

<400> SEQUENCE: 36
ataactgatg atcgg                                               15
```

```
<210> SEQ ID NO 37
<211> LENGTH: 16
<212> TYPE: DNA
<213> ORGANISM: Artificial Sequence
<220> FEATURE:
<223> OTHER INFORMATION: EA-3
<220> FEATURE:
<223> OTHER INFORMATION: Description of Artificial Sequence:nucleic acid
      probe

<400> SEQUENCE: 37
ccacccaatg gacctc                                                         16

<210> SEQ ID NO 38
<211> LENGTH: 18
<212> TYPE: DNA
<213> ORGANISM: Artificial Sequence
<220> FEATURE:
<223> OTHER INFORMATION: EA-4
<220> FEATURE:
<223> OTHER INFORMATION: Description of Artificial Sequence:nucleic acid
      probe

<400> SEQUENCE: 38
gtctttcccg tatcaacc                                                       18

<210> SEQ ID NO 39
<211> LENGTH: 12
<212> TYPE: DNA
<213> ORGANISM: Artificial Sequence
<220> FEATURE:
<223> OTHER INFORMATION: EB-7
<220> FEATURE:
<223> OTHER INFORMATION: Description of Artificial Sequence:nucleic acid
      probe

<400> SEQUENCE: 39
cgccgcatta cg                                                             12

<210> SEQ ID NO 40
<211> LENGTH: 12
<212> TYPE: DNA
<213> ORGANISM: Artificial Sequence
<220> FEATURE:
<223> OTHER INFORMATION: EB-8
<220> FEATURE:
<223> OTHER INFORMATION: Description of Artificial Sequence:nucleic acid
      probe

<400> SEQUENCE: 40
aggggagtct gc                                                             12

<210> SEQ ID NO 41
<211> LENGTH: 13
<212> TYPE: DNA
<213> ORGANISM: Artificial Sequence
<220> FEATURE:
<223> OTHER INFORMATION: GP-3
<220> FEATURE:
<223> OTHER INFORMATION: Description of Artificial Sequence:nucleic acid
      probe

<400> SEQUENCE: 41
ctgtttgccg aca                                                            13

<210> SEQ ID NO 42
<211> LENGTH: 13
<212> TYPE: DNA
<213> ORGANISM: Artificial Sequence
```

```
<220> FEATURE:
<223> OTHER INFORMATION: GP-4
<220> FEATURE:
<223> OTHER INFORMATION: Description of Artificial Sequence:nucleic acid
      probe

<400> SEQUENCE: 42
tatcgccatc cag                                                              13

<210> SEQ ID NO 43
<211> LENGTH: 14
<212> TYPE: DNA
<213> ORGANISM: Artificial Sequence
<220> FEATURE:
<223> OTHER INFORMATION: EB-9
<220> FEATURE:
<223> OTHER INFORMATION: Description of Artificial Sequence:nucleic acid
      probe

<400> SEQUENCE: 43
atgatcgggg tagt                                                             14

<210> SEQ ID NO 44
<211> LENGTH: 16
<212> TYPE: DNA
<213> ORGANISM: Artificial Sequence
<220> FEATURE:
<223> OTHER INFORMATION: EB-10
<220> FEATURE:
<223> OTHER INFORMATION: Description of Artificial Sequence:nucleic acid
      probe

<400> SEQUENCE: 44
agagacctta aggata                                                           16

<210> SEQ ID NO 45
<211> LENGTH: 15
<212> TYPE: DNA
<213> ORGANISM: Artificial Sequence
<220> FEATURE:
<223> OTHER INFORMATION: NG-1
<220> FEATURE:
<223> OTHER INFORMATION: Description of Artificial Sequence:nucleic acid
      probe

<400> SEQUENCE: 45
attccagaac cacgg                                                            15

<210> SEQ ID NO 46
<211> LENGTH: 13
<212> TYPE: DNA
<213> ORGANISM: Artificial Sequence
<220> FEATURE:
<223> OTHER INFORMATION: NG-2
<220> FEATURE:
<223> OTHER INFORMATION: Description of Artificial Sequence:nucleic acid
      probe

<400> SEQUENCE: 46
ttccagaacc acg                                                              13

<210> SEQ ID NO 47
<211> LENGTH: 11
<212> TYPE: DNA
<213> ORGANISM: Artificial Sequence
<220> FEATURE:
<223> OTHER INFORMATION: NG-3
<220> FEATURE:
<223> OTHER INFORMATION: Description of Artificial Sequence:nucleic acid
      probe
```

-continued

```
<400> SEQUENCE: 47
tccagaacca c                                                              11

<210> SEQ ID NO 48
<211> LENGTH: 13
<212> TYPE: DNA
<213> ORGANISM: Artificial Sequence
<220> FEATURE:
<223> OTHER INFORMATION: GP-5
<220> FEATURE:
<223> OTHER INFORMATION: Description of Artificial Sequence:nucleic acid
      probe

<400> SEQUENCE: 48
gttcctggcg cag                                                            13

<210> SEQ ID NO 49
<211> LENGTH: 12
<212> TYPE: DNA
<213> ORGANISM: Artificial Sequence
<220> FEATURE:
<223> OTHER INFORMATION: GP-6
<220> FEATURE:
<223> OTHER INFORMATION: Description of Artificial Sequence:nucleic acid
      probe

<400> SEQUENCE: 49
ttcctggcgc ag                                                             12

<210> SEQ ID NO 50
<211> LENGTH: 24
<212> TYPE: DNA
<213> ORGANISM: Artificial Sequence
<220> FEATURE:
<223> OTHER INFORMATION: NF-1
<220> FEATURE:
<223> OTHER INFORMATION: Description of Artificial Sequence:nucleic acid
      probe

<400> SEQUENCE: 50
gcccgcgccg ccagcactac tttc                                                24

<210> SEQ ID NO 51
<211> LENGTH: 35
<212> TYPE: DNA
<213> ORGANISM: Artificial Sequence
<220> FEATURE:
<223> OTHER INFORMATION: FG-1
<220> FEATURE:
<223> OTHER INFORMATION: Description of Artificial Sequence:nucleic acid
      probe

<400> SEQUENCE: 51
aaacgttggg aggtgtgtgc gtcatcctgg agcta                                    35

<210> SEQ ID NO 52
<211> LENGTH: 25
<212> TYPE: DNA
<213> ORGANISM: Artificial Sequence
<220> FEATURE:
<223> OTHER INFORMATION: LE-3
<220> FEATURE:
<223> OTHER INFORMATION: Description of Artificial Sequence:nucleic acid
      probe

<400> SEQUENCE: 52
gccaaaaccg agtgaggttc tgtgt                                               25
```

```
<210> SEQ ID NO 53
<211> LENGTH: 24
<212> TYPE: DNA
<213> ORGANISM: Artificial Sequence
<220> FEATURE:
<223> OTHER INFORMATION: NF-2
<220> FEATURE:
<223> OTHER INFORMATION: Description of Artificial Sequence:nucleic acid
      probe

<400> SEQUENCE: 53
aaacgttggg aggtgtgtgc gtca                                              24

<210> SEQ ID NO 54
<211> LENGTH: 23
<212> TYPE: DNA
<213> ORGANISM: Artificial Sequence
<220> FEATURE:
<223> OTHER INFORMATION: RA-3
<220> FEATURE:
<223> OTHER INFORMATION: Description of Artificial Sequence:nucleic acid
      probe

<400> SEQUENCE: 54
tgctcgtcac gaagtcactc atg                                               23

<210> SEQ ID NO 55
<211> LENGTH: 21
<212> TYPE: DNA
<213> ORGANISM: Artificial Sequence
<220> FEATURE:
<223> OTHER INFORMATION: ON-2
<220> FEATURE:
<223> OTHER INFORMATION: Description of Artificial Sequence:nucleic acid
      probe

<400> SEQUENCE: 55
cattactgcc cgcaccggac c                                                 21

<210> SEQ ID NO 56
<211> LENGTH: 24
<212> TYPE: DNA
<213> ORGANISM: Artificial Sequence
<220> FEATURE:
<223> OTHER INFORMATION: LE-1
<220> FEATURE:
<223> OTHER INFORMATION: Description of Artificial Sequence:nucleic acid
      probe

<400> SEQUENCE: 56
gccgtggtgt tcctgaacac cagg                                              24

<210> SEQ ID NO 57
<211> LENGTH: 25
<212> TYPE: DNA
<213> ORGANISM: Artificial Sequence
<220> FEATURE:
<223> OTHER INFORMATION: LE-4
<220> FEATURE:
<223> OTHER INFORMATION: Description of Artificial Sequence:nucleic acid
      probe

<400> SEQUENCE: 57
agtcagggtt gcccgacttc gtcac                                             25

<210> SEQ ID NO 58
<211> LENGTH: 26
<212> TYPE: DNA
<213> ORGANISM: Artificial Sequence
```

```
<220> FEATURE:
<223> OTHER INFORMATION: NF-3
<220> FEATURE:
<223> OTHER INFORMATION: Description of Artificial Sequence:nucleic acid
      probe

<400> SEQUENCE: 58
caggcgtcct cggtctcggg cggggc                                          26

<210> SEQ ID NO 59
<211> LENGTH: 20
<212> TYPE: DNA
<213> ORGANISM: Artificial Sequence
<220> FEATURE:
<223> OTHER INFORMATION: LE-2
<220> FEATURE:
<223> OTHER INFORMATION: Description of Artificial Sequence:nucleic acid
      probe

<400> SEQUENCE: 59
cccacgtcac cgggggcccc                                                 20

<210> SEQ ID NO 60
<211> LENGTH: 25
<212> TYPE: DNA
<213> ORGANISM: Artificial Sequence
<220> FEATURE:
<223> OTHER INFORMATION: LE-2
<220> FEATURE:
<223> OTHER INFORMATION: Description of Artificial Sequence:nucleic acid
      probe

<400> SEQUENCE: 60
gccggtcgcg tgcgacgccc aaggc                                           25

<210> SEQ ID NO 61
<211> LENGTH: 26
<212> TYPE: DNA
<213> ORGANISM: Artificial Sequence
<220> FEATURE:
<223> OTHER INFORMATION: SG-3
<220> FEATURE:
<223> OTHER INFORMATION: Description of Artificial Sequence:nucleic acid
      probe

<400> SEQUENCE: 61
ccgacgcgtg ggtatctagg gggtcg                                          26

<210> SEQ ID NO 62
<211> LENGTH: 26
<212> TYPE: DNA
<213> ORGANISM: Artificial Sequence
<220> FEATURE:
<223> OTHER INFORMATION: SG-4
<220> FEATURE:
<223> OTHER INFORMATION: Description of Artificial Sequence:nucleic acid
      probe

<400> SEQUENCE: 62
cgggacggcg agcggaaagt caacgt                                          26

<210> SEQ ID NO 63
<211> LENGTH: 9
<212> TYPE: DNA
<213> ORGANISM: Artificial Sequence
<220> FEATURE:
<223> OTHER INFORMATION: HX-4
<220> FEATURE:
<223> OTHER INFORMATION: Description of Artificial Sequence:nucleic acid
      probe
```

-continued

```
<400> SEQUENCE: 63 ggcgcgggc                                                                  9

<210> SEQ ID NO 64
<211> LENGTH: 15
<212> TYPE: DNA
<213> ORGANISM: Artificial Sequence
<220> FEATURE:
<223> OTHER INFORMATION: HX-5
<220> FEATURE:
<223> OTHER INFORMATION: Description of Artificial Sequence:nucleic acid
      probe

<400> SEQUENCE: 64
gaaagtagtg ctggc                                                          15

<210> SEQ ID NO 65
<211> LENGTH: 11
<212> TYPE: DNA
<213> ORGANISM: Artificial Sequence
<220> FEATURE:
<223> OTHER INFORMATION: GP-7
<220> FEATURE:
<223> OTHER INFORMATION: Description of Artificial Sequence:nucleic acid
      probe

<400> SEQUENCE: 65
tgctggcggc g                                                              11

<210> SEQ ID NO 66
<211> LENGTH: 13
<212> TYPE: DNA
<213> ORGANISM: Artificial Sequence
<220> FEATURE:
<223> OTHER INFORMATION: AZ-3
<220> FEATURE:
<223> OTHER INFORMATION: Description of Artificial Sequence:nucleic acid
      probe

<400> SEQUENCE: 66
acacctccca acg                                                            13

<210> SEQ ID NO 67
<211> LENGTH: 13
<212> TYPE: DNA
<213> ORGANISM: Artificial Sequence
<220> FEATURE:
<223> OTHER INFORMATION: AZ-4
<220> FEATURE:
<223> OTHER INFORMATION: Description of Artificial Sequence:nucleic acid
      probe

<400> SEQUENCE: 67
ctccaggatg acg                                                            13

<210> SEQ ID NO 68
<211> LENGTH: 12
<212> TYPE: DNA
<213> ORGANISM: Artificial Sequence
<220> FEATURE:
<223> OTHER INFORMATION: GR-1
<220> FEATURE:
<223> OTHER INFORMATION: Description of Artificial Sequence:nucleic acid
      probe

<400> SEQUENCE: 68
tcggttttgg tc                                                             12
```

```
<210> SEQ ID NO 69
<211> LENGTH: 13
<212> TYPE: DNA
<213> ORGANISM: Artificial Sequence
<220> FEATURE:
<223> OTHER INFORMATION: GR-2
<220> FEATURE:
<223> OTHER INFORMATION: Description of Artificial Sequence:nucleic acid
      probe

<400> SEQUENCE: 69
acacagaacc tca                                                          13

<210> SEQ ID NO 70
<211> LENGTH: 13
<212> TYPE: DNA
<213> ORGANISM: Artificial Sequence
<220> FEATURE:
<223> OTHER INFORMATION: GP-8
<220> FEATURE:
<223> OTHER INFORMATION: Description of Artificial Sequence:nucleic acid
      probe

<400> SEQUENCE: 70
cacacacctc cca                                                          13

<210> SEQ ID NO 71
<211> LENGTH: 14
<212> TYPE: DNA
<213> ORGANISM: Artificial Sequence
<220> FEATURE:
<223> OTHER INFORMATION: BR-10
<220> FEATURE:
<223> OTHER INFORMATION: Description of Artificial Sequence:nucleic acid
      probe

<400> SEQUENCE: 71
cgacccccta gata                                                         14

<210> SEQ ID NO 72
<211> LENGTH: 11
<212> TYPE: DNA
<213> ORGANISM: Artificial Sequence
<220> FEATURE:
<223> OTHER INFORMATION: BR-11
<220> FEATURE:
<223> OTHER INFORMATION: Description of Artificial Sequence:nucleic acid
      probe

<400> SEQUENCE: 72
ccacgcgtcg g                                                            11

<210> SEQ ID NO 73
<211> LENGTH: 15
<212> TYPE: DNA
<213> ORGANISM: Artificial Sequence
<220> FEATURE:
<223> OTHER INFORMATION: HX-6
<220> FEATURE:
<223> OTHER INFORMATION: Description of Artificial Sequence:nucleic acid
      probe

<400> SEQUENCE: 73
acgttgactt tccgc                                                        15

<210> SEQ ID NO 74
<211> LENGTH: 10
<212> TYPE: DNA
<213> ORGANISM: Artificial Sequence
```

```
<220> FEATURE:
<223> OTHER INFORMATION: BR-15
<220> FEATURE:
<223> OTHER INFORMATION: Description of Artificial Sequence:nucleic acid
      probe

<400> SEQUENCE: 74
cgccgtcccg                                                              10

<210> SEQ ID NO 75
<211> LENGTH: 33
<212> TYPE: DNA
<213> ORGANISM: Artificial Sequence
<220> FEATURE:
<223> OTHER INFORMATION: ZL-1
<220> FEATURE:
<223> OTHER INFORMATION: Description of Artificial Sequence:nucleic acid
      probe

<400> SEQUENCE: 75
gtacagatgg taccggggtt gtagaagtat ctg                                    33

<210> SEQ ID NO 76
<211> LENGTH: 31
<212> TYPE: DNA
<213> ORGANISM: Artificial Sequence
<220> FEATURE:
<223> OTHER INFORMATION: ZL-4
<220> FEATURE:
<223> OTHER INFORMATION: Description of Artificial Sequence:nucleic acid
      probe

<400> SEQUENCE: 76
ctgcaacaag acatacatcg accggtccac c                                      31

<210> SEQ ID NO 77
<211> LENGTH: 31
<212> TYPE: DNA
<213> ORGANISM: Artificial Sequence
<220> FEATURE:
<223> OTHER INFORMATION: DP-1
<220> FEATURE:
<223> OTHER INFORMATION: Description of Artificial Sequence:nucleic acid
      probe

<400> SEQUENCE: 77
gaagtaggtg aggctgcatg tgaagtggta g                                      31

<210> SEQ ID NO 78
<211> LENGTH: 33
<212> TYPE: DNA
<213> ORGANISM: Artificial Sequence
<220> FEATURE:
<223> OTHER INFORMATION: DP-4
<220> FEATURE:
<223> OTHER INFORMATION: Description of Artificial Sequence:nucleic acid
      probe

<400> SEQUENCE: 78
cagctctgtg cataactgtg gtaactttct ggg                                    33

<210> SEQ ID NO 79
<211> LENGTH: 33
<212> TYPE: DNA
<213> ORGANISM: Artificial Sequence
<220> FEATURE:
<223> OTHER INFORMATION: SH-1
<220> FEATURE:
<223> OTHER INFORMATION: Description of Artificial Sequence:nucleic acid
      probe
```

<400> SEQUENCE: 79
gaggtcttct ccaacatgct atgcaacgtc ctg                33

<210> SEQ ID NO 80
<211> LENGTH: 33
<212> TYPE: DNA
<213> ORGANISM: Artificial Sequence
<220> FEATURE:
<223> OTHER INFORMATION: SH-4
<220> FEATURE:
<223> OTHER INFORMATION: Description of Artificial Sequence:nucleic acid
      probe

<400> SEQUENCE: 80
gtgtaggtgc atgctctata ggtacatcag gcc                33

<210> SEQ ID NO 81
<211> LENGTH: 33
<212> TYPE: DNA
<213> ORGANISM: Artificial Sequence
<220> FEATURE:
<223> OTHER INFORMATION: VS-1
<220> FEATURE:
<223> OTHER INFORMATION: Description of Artificial Sequence:nucleic acid
      probe

<400> SEQUENCE: 81
caatgccgag cttagttcat gcaatttccg agg                33

<210> SEQ ID NO 82
<211> LENGTH: 33
<212> TYPE: DNA
<213> ORGANISM: Artificial Sequence
<220> FEATURE:
<223> OTHER INFORMATION: VS-4
<220> FEATURE:
<223> OTHER INFORMATION: Description of Artificial Sequence:nucleic acid
      probe

<400> SEQUENCE: 82
gaagtagtag ttgcagacgc ccctaaaggt tgc                33

<210> SEQ ID NO 83
<211> LENGTH: 30
<212> TYPE: DNA
<213> ORGANISM: Artificial Sequence
<220> FEATURE:
<223> OTHER INFORMATION: AH-1
<220> FEATURE:
<223> OTHER INFORMATION: Description of Artificial Sequence:nucleic acid
      probe

<400> SEQUENCE: 83
gaacgcgatg gtacaggcac tgcagggtcc                30

<210> SEQ ID NO 84
<211> LENGTH: 24
<212> TYPE: DNA
<213> ORGANISM: Artificial Sequence
<220> FEATURE:
<223> OTHER INFORMATION: AG-2
<220> FEATURE:
<223> OTHER INFORMATION: Description of Artificial Sequence:nucleic acid
      probe

<400> SEQUENCE: 84
gaacgcgatg gtacaggcac tgca                24

```
<210> SEQ ID NO 85
<211> LENGTH: 24
<212> TYPE: DNA
<213> ORGANISM: Artificial Sequence
<220> FEATURE:
<223> OTHER INFORMATION: AL-1
<220> FEATURE:
<223> OTHER INFORMATION: Description of Artificial Sequence:nucleic acid
      probe

<400> SEQUENCE: 85
acgcccaccc aatggaatgt accc                                            24

<210> SEQ ID NO 86
<211> LENGTH: 32
<212> TYPE: DNA
<213> ORGANISM: Artificial Sequence
<220> FEATURE:
<223> OTHER INFORMATION: PA-4
<220> FEATURE:
<223> OTHER INFORMATION: Description of Artificial Sequence:nucleic acid
      probe

<400> SEQUENCE: 86
tctgcgtcgt tggagtcgtt cctgtcgtgc tc                                   32

<210> SEQ ID NO 87
<211> LENGTH: 36
<212> TYPE: DNA
<213> ORGANISM: Artificial Sequence
<220> FEATURE:
<223> OTHER INFORMATION: 18-1AB
<220> FEATURE:
<223> OTHER INFORMATION: Description of Artificial Sequence:nucleic acid
      probe

<400> SEQUENCE: 87
ttattattac tacatacatt gccgccatgt tcgcca                               36

<210> SEQ ID NO 88
<211> LENGTH: 46
<212> TYPE: DNA
<213> ORGANISM: Artificial Sequence
<220> FEATURE:
<223> OTHER INFORMATION: 18-2AB
<220> FEATURE:
<223> OTHER INFORMATION: Description of Artificial Sequence:nucleic acid
      probe

<400> SEQUENCE: 88
ttattattat gttgccctct gtgccccgt tgtctatagc ctccgt                     46

<210> SEQ ID NO 89
<211> LENGTH: 38
<212> TYPE: DNA
<213> ORGANISM: Artificial Sequence
<220> FEATURE:
<223> OTHER INFORMATION: 18-3AB
<220> FEATURE:
<223> OTHER INFORMATION: Description of Artificial Sequence:nucleic acid
      probe

<400> SEQUENCE: 89
ttattattag gagcagtgcc caaaagatta aagtttgc                             38

<210> SEQ ID NO 90
<211> LENGTH: 37
<212> TYPE: DNA
<213> ORGANISM: Artificial Sequence
```

```
<220> FEATURE:
<223> OTHER INFORMATION: 18-4AB
<220> FEATURE:
<223> OTHER INFORMATION: Description of Artificial Sequence:nucleic acid
      probe

<400> SEQUENCE: 90
ttattattac acggtgctgg aatacggtga gggggtg                                37

<210> SEQ ID NO 91
<211> LENGTH: 33
<212> TYPE: DNA
<213> ORGANISM: Artificial Sequence
<220> FEATURE:
<223> OTHER INFORMATION: 18-5AB
<220> FEATURE:
<223> OTHER INFORMATION: Description of Artificial Sequence:nucleic acid
      probe

<400> SEQUENCE: 91
ttattattaa cgcccaccca atggaatgta ccc                                   33

<210> SEQ ID NO 92
<211> LENGTH: 35
<212> TYPE: DNA
<213> ORGANISM: Artificial Sequence
<220> FEATURE:
<223> OTHER INFORMATION: 18-6AB
<220> FEATURE:
<223> OTHER INFORMATION: Description of Artificial Sequence:nucleic acid
      probe

<400> SEQUENCE: 92
ttattattaa tagtattgtg gtgtgtttct cacat                                 35

<210> SEQ ID NO 93
<211> LENGTH: 30
<212> TYPE: DNA
<213> ORGANISM: Artificial Sequence
<220> FEATURE:
<223> OTHER INFORMATION: 18-7AB
<220> FEATURE:
<223> OTHER INFORMATION: Description of Artificial Sequence:nucleic acid
      probe

<400> SEQUENCE: 93
ttattattag ttggagtcgt tcctgtcgtg                                       30

<210> SEQ ID NO 94
<211> LENGTH: 31
<212> TYPE: DNA
<213> ORGANISM: Artificial Sequence
<220> FEATURE:
<223> OTHER INFORMATION: 18-8AB
<220> FEATURE:
<223> OTHER INFORMATION: Description of Artificial Sequence:nucleic acid
      probe

<400> SEQUENCE: 94
ttattattac ggaatttcat tttggggctc t                                     31

<210> SEQ ID NO 95
<211> LENGTH: 33
<212> TYPE: DNA
<213> ORGANISM: Artificial Sequence
<220> FEATURE:
<223> OTHER INFORMATION: PE-1
<220> FEATURE:
<223> OTHER INFORMATION: Description of Artificial Sequence:nucleic acid
      probe
```

```
<400> SEQUENCE: 95
gctcgaaggt cgtctgctga gctttctact act                                    33

<210> SEQ ID NO 96
<211> LENGTH: 32
<212> TYPE: DNA
<213> ORGANISM: Artificial Sequence
<220> FEATURE:
<223> OTHER INFORMATION: PZ-2
<220> FEATURE:
<223> OTHER INFORMATION: Description of Artificial Sequence:nucleic acid
      probe

<400> SEQUENCE: 96
gcgccatcct gtaatgcact tttccacaaa gc                                     32

<210> SEQ ID NO 97
<211> LENGTH: 31
<212> TYPE: DNA
<213> ORGANISM: Artificial Sequence
<220> FEATURE:
<223> OTHER INFORMATION: PZ-5
<220> FEATURE:
<223> OTHER INFORMATION: Description of Artificial Sequence:nucleic acid
      probe

<400> SEQUENCE: 97
tagtgctagg tgtagtggac gcaggaggtg g                                      31

<210> SEQ ID NO 98
<211> LENGTH: 32
<212> TYPE: DNA
<213> ORGANISM: Artificial Sequence
<220> FEATURE:
<223> OTHER INFORMATION: CS-1
<220> FEATURE:
<223> OTHER INFORMATION: Description of Artificial Sequence:nucleic acid
      probe

<400> SEQUENCE: 98
ggtcacaaca tgtattacac tgccctcggt ac                                     32

<210> SEQ ID NO 99
<211> LENGTH: 31
<212> TYPE: DNA
<213> ORGANISM: Artificial Sequence
<220> FEATURE:
<223> OTHER INFORMATION: CS-4
<220> FEATURE:
<223> OTHER INFORMATION: Description of Artificial Sequence:nucleic acid
      probe

<400> SEQUENCE: 99
cctacgtctg cgaagtcttt cttgccgtgc c                                      31

<210> SEQ ID NO 100
<211> LENGTH: 34
<212> TYPE: DNA
<213> ORGANISM: Artificial Sequence
<220> FEATURE:
<223> OTHER INFORMATION: PF-1
<220> FEATURE:
<223> OTHER INFORMATION: Description of Artificial Sequence:nucleic acid
      probe

<400> SEQUENCE: 100
ctgcattgtc actactatcc ccaccactac tttg                                   34
```

```
<210> SEQ ID NO 101
<211> LENGTH: 32
<212> TYPE: DNA
<213> ORGANISM: Artificial Sequence
<220> FEATURE:
<223> OTHER INFORMATION: PF-4
<220> FEATURE:
<223> OTHER INFORMATION: Description of Artificial Sequence:nucleic acid
      probe

<400> SEQUENCE: 101
ccacaaggca cattcataca tacacgcacg ca                                     32

<210> SEQ ID NO 102
<211> LENGTH: 33
<212> TYPE: DNA
<213> ORGANISM: Artificial Sequence
<220> FEATURE:
<223> OTHER INFORMATION: PA-1
<220> FEATURE:
<223> OTHER INFORMATION: Description of Artificial Sequence:nucleic acid
      probe

<400> SEQUENCE: 102
gttctaaggt cctctgccga gctctctact gta                                    33

<210> SEQ ID NO 103
<211> LENGTH: 36
<212> TYPE: DNA
<213> ORGANISM: Artificial Sequence
<220> FEATURE:
<223> OTHER INFORMATION: 45-5AB
<220> FEATURE:
<223> OTHER INFORMATION: Description of Artificial Sequence:nucleic acid
      probe

<400> SEQUENCE: 103
ttattattat gcggttttgg gggtcgacgt ggaggc                                 36

<210> SEQ ID NO 104
<211> LENGTH: 36
<212> TYPE: DNA
<213> ORGANISM: Artificial Sequence
<220> FEATURE:
<223> OTHER INFORMATION: 45-6AB
<220> FEATURE:
<223> OTHER INFORMATION: Description of Artificial Sequence:nucleic acid
      probe

<400> SEQUENCE: 104
ttattattaa gacctgcccc ctaagggtac atagcc                                 36

<210> SEQ ID NO 105
<211> LENGTH: 49
<212> TYPE: DNA
<213> ORGANISM: Artificial Sequence
<220> FEATURE:
<223> OTHER INFORMATION: 45-8AB
<220> FEATURE:
<223> OTHER INFORMATION: Description of Artificial Sequence:nucleic acid
      probe

<400> SEQUENCE: 105
ttattattac agcattgcag ccttttttgtt acttgcttgt aatagctcc                  49

<210> SEQ ID NO 106
<211> LENGTH: 34
<212> TYPE: DNA
<213> ORGANISM: Artificial Sequence
```

```
<220> FEATURE:
<223> OTHER INFORMATION: 45-9AB
<220> FEATURE:
<223> OTHER INFORMATION: Description of Artificial Sequence:nucleic acid
      probe

<400> SEQUENCE: 106
ttattattaa tcctgtaatg cacttttcca caaa                              34

<210> SEQ ID NO 107
<211> LENGTH: 31
<212> TYPE: DNA
<213> ORGANISM: Artificial Sequence
<220> FEATURE:
<223> OTHER INFORMATION: 45-10AB
<220> FEATURE:
<223> OTHER INFORMATION: Description of Artificial Sequence:nucleic acid
      probe

<400> SEQUENCE: 107
ttattattag cctggtcaca acatgtatta c                                 31

<210> SEQ ID NO 108
<211> LENGTH: 33
<212> TYPE: DNA
<213> ORGANISM: Artificial Sequence
<220> FEATURE:
<223> OTHER INFORMATION: 45-11AB
<220> FEATURE:
<223> OTHER INFORMATION: Description of Artificial Sequence:nucleic acid
      probe

<400> SEQUENCE: 108
ttattattac aggatctaat tcattctgag gtt                               33

<210> SEQ ID NO 109
<211> LENGTH: 27
<212> TYPE: DNA
<213> ORGANISM: Artificial Sequence
<220> FEATURE:
<223> OTHER INFORMATION: ON-1
<220> FEATURE:
<223> OTHER INFORMATION: Description of Artificial Sequence:nucleic acid
      probe

<400> SEQUENCE: 109
tgcggttttg ggggtcgacg tggaggc                                      27

<210> SEQ ID NO 110
<211> LENGTH: 14
<212> TYPE: DNA
<213> ORGANISM: Artificial Sequence
<220> FEATURE:
<223> OTHER INFORMATION: PV-FD-1
<220> FEATURE:
<223> OTHER INFORMATION: Description of Artificial Sequence:nucleic acid
      probe

<400> SEQUENCE: 110
gcctccacgt cgac                                                    14

<210> SEQ ID NO 111
<211> LENGTH: 11
<212> TYPE: DNA
<213> ORGANISM: Artificial Sequence
<220> FEATURE:
<223> OTHER INFORMATION: PV-FD-2
<220> FEATURE:
<223> OTHER INFORMATION: Description of Artificial Sequence:nucleic acid
      probe
```

-continued

```
<400> SEQUENCE: 111
ccccaaaacc g                                                               11

<210> SEQ ID NO 112
<211> LENGTH: 16
<212> TYPE: DNA
<213> ORGANISM: Artificial Sequence
<220> FEATURE:
<223> OTHER INFORMATION: PV-FD-3
<220> FEATURE:
<223> OTHER INFORMATION: Description of Artificial Sequence:nucleic acid
      probe

<400> SEQUENCE: 112
ggtacattcc attggg                                                          16

<210> SEQ ID NO 113
<211> LENGTH: 16
<212> TYPE: DNA
<213> ORGANISM: Artificial Sequence
<220> FEATURE:
<223> OTHER INFORMATION: PV-FD-4
<220> FEATURE:
<223> OTHER INFORMATION: Description of Artificial Sequence:nucleic acid
      probe

<400> SEQUENCE: 113
tgggcgttaa taataa                                                          16

<210> SEQ ID NO 114
<211> LENGTH: 12
<212> TYPE: DNA
<213> ORGANISM: Artificial Sequence
<220> FEATURE:
<223> OTHER INFORMATION: AH-3
<220> FEATURE:
<223> OTHER INFORMATION: Description of Artificial Sequence:nucleic acid
      probe

<400> SEQUENCE: 114
accatcgcgt tc                                                              12

<210> SEQ ID NO 115
<211> LENGTH: 14
<212> TYPE: DNA
<213> ORGANISM: Artificial Sequence
<220> FEATURE:
<223> OTHER INFORMATION: AH-4
<220> FEATURE:
<223> OTHER INFORMATION: Description of Artificial Sequence:nucleic acid
      probe

<400> SEQUENCE: 115
ggaccctgca gtgc                                                            14

<210> SEQ ID NO 116
<211> LENGTH: 15
<212> TYPE: DNA
<213> ORGANISM: Artificial Sequence
<220> FEATURE:
<223> OTHER INFORMATION: AH-5
<220> FEATURE:
<223> OTHER INFORMATION: Description of Artificial Sequence:nucleic acid
      probe

<400> SEQUENCE: 116
ctgtaccatc gcgtt                                                           15
```

```
<210> SEQ ID NO 117
<211> LENGTH: 12
<212> TYPE: DNA
<213> ORGANISM: Artificial Sequence
<220> FEATURE:
<223> OTHER INFORMATION: AH-6
<220> FEATURE:
<223> OTHER INFORMATION: Description of Artificial Sequence:nucleic acid
      probe

<400> SEQUENCE: 117
tgcagtgcct gt                                                          12

<210> SEQ ID NO 118
<211> LENGTH: 13
<212> TYPE: DNA
<213> ORGANISM: Artificial Sequence
<220> FEATURE:
<223> OTHER INFORMATION: PZ-1
<220> FEATURE:
<223> OTHER INFORMATION: Description of Artificial Sequence:nucleic acid
      probe

<400> SEQUENCE: 118
ccacctcctg cgt                                                         13

<210> SEQ ID NO 119
<211> LENGTH: 15
<212> TYPE: DNA
<213> ORGANISM: Artificial Sequence
<220> FEATURE:
<223> OTHER INFORMATION: PZ-3
<220> FEATURE:
<223> OTHER INFORMATION: Description of Artificial Sequence:nucleic acid
      probe

<400> SEQUENCE: 119
attacaggat ggcgc                                                       15

<210> SEQ ID NO 120
<211> LENGTH: 16
<212> TYPE: DNA
<213> ORGANISM: Artificial Sequence
<220> FEATURE:
<223> OTHER INFORMATION: PZ-4
<220> FEATURE:
<223> OTHER INFORMATION: Description of Artificial Sequence:nucleic acid
      probe

<400> SEQUENCE: 120
gctttctgga aaagtg                                                      16

<210> SEQ ID NO 121
<211> LENGTH: 18
<212> TYPE: DNA
<213> ORGANISM: Artificial Sequence
<220> FEATURE:
<223> OTHER INFORMATION: PZ-6
<220> FEATURE:
<223> OTHER INFORMATION: Description of Artificial Sequence:nucleic acid
      probe

<400> SEQUENCE: 121
ccactacacc tagcacta                                                    18

<210> SEQ ID NO 122
<211> LENGTH: 17
<212> TYPE: DNA
<213> ORGANISM: Artificial Sequence
```

```
-continued

<220> FEATURE:
<223> OTHER INFORMATION: ZL-2
<220> FEATURE:
<223> OTHER INFORMATION: Description of Artificial Sequence:nucleic acid
      probe

<400> SEQUENCE: 122
cagatacttc tacaacc                                                     17

<210> SEQ ID NO 123
<211> LENGTH: 16
<212> TYPE: DNA
<213> ORGANISM: Artificial Sequence
<220> FEATURE:
<223> OTHER INFORMATION: ZL-3
<220> FEATURE:
<223> OTHER INFORMATION: Description of Artificial Sequence:nucleic acid
      probe

<400> SEQUENCE: 123
ccggtaccat ctgtac                                                      16

<210> SEQ ID NO 124
<211> LENGTH: 13
<212> TYPE: DNA
<213> ORGANISM: Artificial Sequence
<220> FEATURE:
<223> OTHER INFORMATION: ZL-5
<220> FEATURE:
<223> OTHER INFORMATION: Description of Artificial Sequence:nucleic acid
      probe

<400> SEQUENCE: 124
ggtggaccgg tcg                                                         13

<210> SEQ ID NO 125
<211> LENGTH: 18
<212> TYPE: DNA
<213> ORGANISM: Artificial Sequence
<220> FEATURE:
<223> OTHER INFORMATION: ZL-6
<220> FEATURE:
<223> OTHER INFORMATION: Description of Artificial Sequence:nucleic acid
      probe

<400> SEQUENCE: 125
atgtatgtct tgttgcag                                                    18

<210> SEQ ID NO 126
<211> LENGTH: 16
<212> TYPE: DNA
<213> ORGANISM: Artificial Sequence
<220> FEATURE:
<223> OTHER INFORMATION: DP-2
<220> FEATURE:
<223> OTHER INFORMATION: Description of Artificial Sequence:nucleic acid
      probe

<400> SEQUENCE: 126
ctaccacttc acatgc                                                      16

<210> SEQ ID NO 127
<211> LENGTH: 15
<212> TYPE: DNA
<213> ORGANISM: Artificial Sequence
<220> FEATURE:
<223> OTHER INFORMATION: DP-3
<220> FEATURE:
<223> OTHER INFORMATION: Description of Artificial Sequence:nucleic acid
      probe
```

```
<400> SEQUENCE: 127
agcctcacct acttc                                                    15

<210> SEQ ID NO 128
<211> LENGTH: 16
<212> TYPE: DNA
<213> ORGANISM: Artificial Sequence
<220> FEATURE:
<223> OTHER INFORMATION: DP-5
<220> FEATURE:
<223> OTHER INFORMATION: Description of Artificial Sequence:nucleic acid
      probe

<400> SEQUENCE: 128
cccagaaagt taccac                                                   16

<210> SEQ ID NO 129
<211> LENGTH: 16
<212> TYPE: DNA
<213> ORGANISM: Artificial Sequence
<220> FEATURE:
<223> OTHER INFORMATION: DP-6
<220> FEATURE:
<223> OTHER INFORMATION: Description of Artificial Sequence:nucleic acid
      probe

<400> SEQUENCE: 129
agttatgcac agagct                                                   16

<210> SEQ ID NO 130
<211> LENGTH: 16
<212> TYPE: DNA
<213> ORGANISM: Artificial Sequence
<220> FEATURE:
<223> OTHER INFORMATION: SH-2
<220> FEATURE:
<223> OTHER INFORMATION: Description of Artificial Sequence:nucleic acid
      probe

<400> SEQUENCE: 130
caggacgttg catagc                                                   16

<210> SEQ ID NO 131
<211> LENGTH: 17
<212> TYPE: DNA
<213> ORGANISM: Artificial Sequence
<220> FEATURE:
<223> OTHER INFORMATION: SH-3
<220> FEATURE:
<223> OTHER INFORMATION: Description of Artificial Sequence:nucleic acid
      probe

<400> SEQUENCE: 131
atgttggaga agacctc                                                  17

<210> SEQ ID NO 132
<211> LENGTH: 17
<212> TYPE: DNA
<213> ORGANISM: Artificial Sequence
<220> FEATURE:
<223> OTHER INFORMATION: SH-5
<220> FEATURE:
<223> OTHER INFORMATION: Description of Artificial Sequence:nucleic acid
      probe

<400> SEQUENCE: 132
ggcctgatgt acctata                                                  17
```

```
<210> SEQ ID NO 133
<211> LENGTH: 16
<212> TYPE: DNA
<213> ORGANISM: Artificial Sequence
<220> FEATURE:
<223> OTHER INFORMATION: SH-6
<220> FEATURE:
<223> OTHER INFORMATION: Description of Artificial Sequence:nucleic acid
      probe

<400> SEQUENCE: 133
gagcatgcac ctacac                                                    16

<210> SEQ ID NO 134
<211> LENGTH: 15
<212> TYPE: DNA
<213> ORGANISM: Artificial Sequence
<220> FEATURE:
<223> OTHER INFORMATION: VS-2
<220> FEATURE:
<223> OTHER INFORMATION: Description of Artificial Sequence:nucleic acid
      probe

<400> SEQUENCE: 134
ctcggaaatt gcatg                                                     15

<210> SEQ ID NO 135
<211> LENGTH: 16
<212> TYPE: DNA
<213> ORGANISM: Artificial Sequence
<220> FEATURE:
<223> OTHER INFORMATION: VS-3
<220> FEATURE:
<223> OTHER INFORMATION: Description of Artificial Sequence:nucleic acid
      probe

<400> SEQUENCE: 135
aactaagctc ggcatt                                                    16

<210> SEQ ID NO 136
<211> LENGTH: 14
<212> TYPE: DNA
<213> ORGANISM: Artificial Sequence
<220> FEATURE:
<223> OTHER INFORMATION: VS-5
<220> FEATURE:
<223> OTHER INFORMATION: Description of Artificial Sequence:nucleic acid
      probe

<400> SEQUENCE: 136
gcaaccttta gggg                                                      14

<210> SEQ ID NO 137
<211> LENGTH: 19
<212> TYPE: DNA
<213> ORGANISM: Artificial Sequence
<220> FEATURE:
<223> OTHER INFORMATION: VS-6
<220> FEATURE:
<223> OTHER INFORMATION: Description of Artificial Sequence:nucleic acid
      probe

<400> SEQUENCE: 137
cgtctgcaac tactacttc                                                 19

<210> SEQ ID NO 138
<211> LENGTH: 14
<212> TYPE: DNA
<213> ORGANISM: Artificial Sequence
```

```
<220> FEATURE:
<223> OTHER INFORMATION: CS-2
<220> FEATURE:
<223> OTHER INFORMATION: Description of Artificial Sequence:nucleic acid
      probe

<400> SEQUENCE: 138
gtaccgaggg cagt                                                       14

<210> SEQ ID NO 139
<211> LENGTH: 18
<212> TYPE: DNA
<213> ORGANISM: Artificial Sequence
<220> FEATURE:
<223> OTHER INFORMATION: CS-3
<220> FEATURE:
<223> OTHER INFORMATION: Description of Artificial Sequence:nucleic acid
      probe

<400> SEQUENCE: 139
gtaatacatg ttgtgacc                                                   18

<210> SEQ ID NO 140
<211> LENGTH: 14
<212> TYPE: DNA
<213> ORGANISM: Artificial Sequence
<220> FEATURE:
<223> OTHER INFORMATION: CS-5
<220> FEATURE:
<223> OTHER INFORMATION: Description of Artificial Sequence:nucleic acid
      probe

<400> SEQUENCE: 140
ggcacggcaa gaaa                                                       14

<210> SEQ ID NO 141
<211> LENGTH: 17
<212> TYPE: DNA
<213> ORGANISM: Artificial Sequence
<220> FEATURE:
<223> OTHER INFORMATION: CS-6
<220> FEATURE:
<223> OTHER INFORMATION: Description of Artificial Sequence:nucleic acid
      probe

<400> SEQUENCE: 141
gacttcgcag acgtagg                                                    17

<210> SEQ ID NO 142
<211> LENGTH: 15
<212> TYPE: DNA
<213> ORGANISM: Artificial Sequence
<220> FEATURE:
<223> OTHER INFORMATION: PF-2
<220> FEATURE:
<223> OTHER INFORMATION: Description of Artificial Sequence:nucleic acid
      probe

<400> SEQUENCE: 142
caaagtagtg gtggg                                                      15

<210> SEQ ID NO 143
<211> LENGTH: 19
<212> TYPE: DNA
<213> ORGANISM: Artificial Sequence
<220> FEATURE:
<223> OTHER INFORMATION: PF-3
<220> FEATURE:
<223> OTHER INFORMATION: Description of Artificial Sequence:nucleic acid
      probe
```

-continued

<400> SEQUENCE: 143
gatagtagtg acaatgcag                                                    19

<210> SEQ ID NO 144
<211> LENGTH: 16
<212> TYPE: DNA
<213> ORGANISM: Artificial Sequence
<220> FEATURE:
<223> OTHER INFORMATION: PF-5
<220> FEATURE:
<223> OTHER INFORMATION: Description of Artificial Sequence:nucleic acid
      probe

<400> SEQUENCE: 144
tgcgtgcgtg tatgta                                                       16

<210> SEQ ID NO 145
<211> LENGTH: 16
<212> TYPE: DNA
<213> ORGANISM: Artificial Sequence
<220> FEATURE:
<223> OTHER INFORMATION: PF-6
<220> FEATURE:
<223> OTHER INFORMATION: Description of Artificial Sequence:nucleic acid
      probe

<400> SEQUENCE: 145
tgaatgtgcc ttgtgg                                                       16

<210> SEQ ID NO 146
<211> LENGTH: 18
<212> TYPE: DNA
<213> ORGANISM: Artificial Sequence
<220> FEATURE:
<223> OTHER INFORMATION: PE-2
<220> FEATURE:
<223> OTHER INFORMATION: Description of Artificial Sequence:nucleic acid
      probe

<400> SEQUENCE: 146
agtagtagaa agctcagc                                                     18

<210> SEQ ID NO 147
<211> LENGTH: 15
<212> TYPE: DNA
<213> ORGANISM: Artificial Sequence
<220> FEATURE:
<223> OTHER INFORMATION: PE-3
<220> FEATURE:
<223> OTHER INFORMATION: Description of Artificial Sequence:nucleic acid
      probe

<400> SEQUENCE: 147
agacgacctt cgagc                                                        15

<210> SEQ ID NO 148
<211> LENGTH: 17
<212> TYPE: DNA
<213> ORGANISM: Artificial Sequence
<220> FEATURE:
<223> OTHER INFORMATION: PA-2
<220> FEATURE:
<223> OTHER INFORMATION: Description of Artificial Sequence:nucleic acid
      probe

<400> SEQUENCE: 148
tacagtagag agctcgg                                                      17

```
<210> SEQ ID NO 149
<211> LENGTH: 16
<212> TYPE: DNA
<213> ORGANISM: Artificial Sequence
<220> FEATURE:
<223> OTHER INFORMATION: PA-3
<220> FEATURE:
<223> OTHER INFORMATION: Description of Artificial Sequence:nucleic acid
      probe

<400> SEQUENCE: 149
cagaggacct tagaac                                                       16

<210> SEQ ID NO 150
<211> LENGTH: 16
<212> TYPE: DNA
<213> ORGANISM: Artificial Sequence
<220> FEATURE:
<223> OTHER INFORMATION: PA-5
<220> FEATURE:
<223> OTHER INFORMATION: Description of Artificial Sequence:nucleic acid
      probe

<400> SEQUENCE: 150
gagcacgaca ggaacg                                                       16

<210> SEQ ID NO 151
<211> LENGTH: 16
<212> TYPE: DNA
<213> ORGANISM: Artificial Sequence
<220> FEATURE:
<223> OTHER INFORMATION: PA-6
<220> FEATURE:
<223> OTHER INFORMATION: Description of Artificial Sequence:nucleic acid
      probe

<400> SEQUENCE: 151
actccaacga cgcaga                                                       16

<210> SEQ ID NO 152
<211> LENGTH: 28
<212> TYPE: DNA
<213> ORGANISM: Artificial Sequence
<220> FEATURE:
<223> OTHER INFORMATION: HBV C1
<220> FEATURE:
<223> OTHER INFORMATION: Description of Artificial Sequence:nucleic acid
      probe

<400> SEQUENCE: 152
gctggatgtg tctgcggcgt tttatcat                                          28

<210> SEQ ID NO 153
<211> LENGTH: 27
<212> TYPE: DNA
<213> ORGANISM: Artificial Sequence
<220> FEATURE:
<223> OTHER INFORMATION: HBV C2
<220> FEATURE:
<223> OTHER INFORMATION: Description of Artificial Sequence:nucleic acid
      probe

<400> SEQUENCE: 153
actgttcaag cctccaagct gcgcctt                                           27

<210> SEQ ID NO 154
<211> LENGTH: 32
<212> TYPE: DNA
<213> ORGANISM: Artificial Sequence
```

```
<220> FEATURE:
<223> OTHER INFORMATION: HBV C3
<220> FEATURE:
<223> OTHER INFORMATION: Description of Artificial Sequence:nucleic acid
      probe

<400> SEQUENCE: 154
atgataaaac gccgcagaca catccagcga ta                                    32

<210> SEQ ID NO 155
<211> LENGTH: 14
<212> TYPE: DNA
<213> ORGANISM: Artificial Sequence
<220> FEATURE:
<223> OTHER INFORMATION: B1
<220> FEATURE:
<223> OTHER INFORMATION: Description of Artificial Sequence:nucleic acid
      probe

<400> SEQUENCE: 155
atgataaaac gccg                                                        14

<210> SEQ ID NO 156
<211> LENGTH: 14
<212> TYPE: DNA
<213> ORGANISM: Artificial Sequence
<220> FEATURE:
<223> OTHER INFORMATION: B2
<220> FEATURE:
<223> OTHER INFORMATION: Description of Artificial Sequence:nucleic acid
      probe

<400> SEQUENCE: 156
cagacacatc cagc                                                        14

<210> SEQ ID NO 157
<211> LENGTH: 13
<212> TYPE: DNA
<213> ORGANISM: Artificial Sequence
<220> FEATURE:
<223> OTHER INFORMATION: B3
<220> FEATURE:
<223> OTHER INFORMATION: Description of Artificial Sequence:nucleic acid
      probe

<400> SEQUENCE: 157
aaggcacagc ttg                                                         13

<210> SEQ ID NO 158
<211> LENGTH: 14
<212> TYPE: DNA
<213> ORGANISM: Artificial Sequence
<220> FEATURE:
<223> OTHER INFORMATION: B4
<220> FEATURE:
<223> OTHER INFORMATION: Description of Artificial Sequence:nucleic acid
      probe

<400> SEQUENCE: 158
gaggcttgaa cagt                                                        14

<210> SEQ ID NO 159
<211> LENGTH: 16
<212> TYPE: DNA
<213> ORGANISM: Artificial Sequence
<220> FEATURE:
<223> OTHER INFORMATION: B5
<220> FEATURE:
<223> OTHER INFORMATION: Description of Artificial Sequence:nucleic acid
      probe
```

```
<400> SEQUENCE: 159
tatcgctgga tgtgtc                                                        16

<210> SEQ ID NO 160
<211> LENGTH: 16
<212> TYPE: DNA
<213> ORGANISM: Artificial Sequence
<220> FEATURE:
<223> OTHER INFORMATION: B6
<220> FEATURE:
<223> OTHER INFORMATION: Description of Artificial Sequence:nucleic acid
      probe

<400> SEQUENCE: 160
tcggcgtttt atcatg                                                        16
```